(12) United States Patent
Thess et al.

(10) Patent No.: US 10,610,605 B2
(45) Date of Patent: *Apr. 7, 2020

(54) NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED THERAPEUTIC PROTEIN

(71) Applicant: CureVac AG, Tübingen (DE)

(72) Inventors: Andreas Thess, Kusterdingen (DE); Thomas Schlake, Gundelfingen (DE); Jochen Probst, Wolfschlugen (DE)

(73) Assignee: CureVac AG, Tübingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/899,326

(22) Filed: Feb. 19, 2018

(65) Prior Publication Data

US 2018/0185517 A1 Jul. 5, 2018

Related U.S. Application Data

(63) Continuation of application No. 15/233,933, filed on Aug. 10, 2016, now Pat. No. 10,111,968, which is a continuation of application No. 14/378,606, filed as application No. PCT/EP2013/000461 on Feb. 15, 2013, now Pat. No. 9,447,431, which is a continuation of application No. PCT/EP2012/000671, filed on Feb. 15, 2012.

(51) Int. Cl.
| | |
|---|---|
| *A61K 48/00* | (2006.01) |
| *C12N 15/63* | (2006.01) |
| *C12N 15/67* | (2006.01) |
| *A61K 39/00* | (2006.01) |
| *C12N 15/85* | (2006.01) |
| *C07K 14/505* | (2006.01) |
| *C07K 16/32* | (2006.01) |

(52) U.S. Cl.
CPC .......... *A61K 48/0066* (2013.01); *A61K 39/00* (2013.01); *C07K 14/505* (2013.01); *C07K 16/32* (2013.01); *C12N 15/63* (2013.01); *C12N 15/67* (2013.01); *C12N 15/85* (2013.01); *A61K 48/00* (2013.01); *C07K 2317/14* (2013.01); *C07K 2317/24* (2013.01); *C12N 2830/50* (2013.01); *C12N 2840/105* (2013.01)

(58) Field of Classification Search
None
See application file for complete search history.

(56) References Cited

U.S. PATENT DOCUMENTS

| | | | |
|---|---|---|---|
| 5,908,779 A | 6/1999 | Carmichael et al. | |
| 8,217,016 B2 | 7/2012 | Hoerr et al. | |
| 8,383,340 B2 | 2/2013 | Ketterer et al. | |
| 8,703,906 B2 | 4/2014 | Baumhof et al. | |
| 8,968,746 B2 | 3/2015 | Baumhof et al. | |
| 9,155,788 B2 | 10/2015 | Hoerr et al. | |
| 9,234,013 B2 | 1/2016 | Thess et al. | |
| 9,447,431 B2 | 9/2016 | Thess et al. | |
| 9,669,089 B2 | 6/2017 | Thess et al. | |
| 9,839,697 B2 | 12/2017 | Thess et al. | |
| 2004/0038405 A1 | 2/2004 | Liu | |
| 2005/0009028 A1 | 1/2005 | Heintz et al. | |
| 2005/0032730 A1 | 2/2005 | Von Der Mülbe et al. | |
| 2005/0048549 A1 | 3/2005 | Cao et al. | |
| 2005/0059624 A1 | 3/2005 | Hoerr et al. | |
| 2005/0250723 A1 | 11/2005 | Hoerr et al. | |
| 2006/0188490 A1 | 8/2006 | Hoerr et al. | |
| 2007/0111203 A1 | 5/2007 | Cao et al. | |
| 2007/0172949 A9 | 7/2007 | Liu et al. | |
| 2008/0025944 A1 | 1/2008 | Hoerr et al. | |
| 2008/0267873 A1 | 10/2008 | Hoerr et al. | |
| 2009/0324584 A1 | 12/2009 | Hoerr et al. | |
| 2010/0048883 A1 | 2/2010 | Ketterer et al. | |
| 2010/0120152 A1 | 5/2010 | Wooddell et al. | |
| 2010/0129392 A1 | 5/2010 | Shi et al. | |
| 2010/0189729 A1 | 7/2010 | Hoerr et al. | |
| 2010/0203076 A1 | 8/2010 | Fotin-Mleczek et al. | |
| 2010/0239608 A1 | 9/2010 | Von Der Mülbe et al. | |
| 2010/0291156 A1 | 11/2010 | Barner et al. | |
| 2010/0303851 A1 | 12/2010 | Hoerr et al. | |
| 2010/0305196 A1 | 12/2010 | Probst et al. | |
| 2011/0053829 A1 | 3/2011 | Baumhof et al. | |
| 2011/0077287 A1 | 3/2011 | Von Der Mülbe et al. | |
| 2011/0250225 A1 | 10/2011 | Fotin-Mleczek et al. | |
| 2011/0269950 A1 | 11/2011 | Von Der Mülbe et al. | |
| 2011/0311472 A1 | 12/2011 | Hoerr et al. | |
| 2012/0009221 A1 | 1/2012 | Hoerr et al. | |
| 2012/0021043 A1 | 1/2012 | Kramps et al. | |
| 2012/0213818 A1 | 8/2012 | Hoerr et al. | |
| 2012/0258046 A1 | 10/2012 | Mutzke | |

(Continued)

FOREIGN PATENT DOCUMENTS

| | | |
|---|---|---|
| WO | WO 2016407877 | 7/1916 |
| WO | WO 2016465825 | 10/1916 |

(Continued)

OTHER PUBLICATIONS

Shuptrine et al., "Moncclonal antibodies for the treatment of cancer" 22 Seminars in Cancer Biology 3-13 (2012).*

(Continued)

*Primary Examiner* — Nancy J Leith
(74) *Attorney, Agent, or Firm* — Parker Highlander PLLC

(57) ABSTRACT

Provided herein are nucleic acid sequences, comprising or coding for a coding region, encoding at least one peptide or protein comprising a therapeutic protein or a fragment, variant or derivative thereof. Furthermore the use of the nucleic acid for increasing the expression of an encoded peptide or protein is provided. Methods are provided for increasing the expression of a peptide or protein comprising a therapeutic protein or a fragment, variant or derivative thereof.

17 Claims, 25 Drawing Sheets

Specification includes a Sequence Listing.

(56) References Cited

U.S. PATENT DOCUMENTS

| | | |
|---|---|---|
| 2013/0121988 A1 | 5/2013 | Hoerr et al. |
| 2013/0129754 A1 | 5/2013 | Thess et al. |
| 2013/0142818 A1 | 6/2013 | Baumhof et al. |
| 2013/0195867 A1 | 8/2013 | Hoerr et al. |
| 2013/0202645 A1 | 8/2013 | Barner et al. |
| 2013/0251742 A1 | 9/2013 | Probst et al. |
| 2013/0259879 A1 | 10/2013 | Baumhof et al. |
| 2013/0273001 A1 | 10/2013 | Hoerr et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2014/0037660 A1 | 2/2014 | Fotin-Mleczek et al. |
| 2014/0147454 A1 | 5/2014 | Chakraborty et al. |
| 2014/0294877 A1 | 10/2014 | Baumhof et al. |
| 2015/0037326 A1 | 2/2015 | Butler-Ransohoff et al. |
| 2015/0050302 A1 | 2/2015 | Thess |
| 2015/0093413 A1 | 4/2015 | Thess |
| 2015/0104476 A1 | 4/2015 | Von Der Mülbe et al. |
| 2015/0118183 A1 | 4/2015 | Baumhof |
| 2015/0118264 A1 | 4/2015 | Baumhof et al. |
| 2015/0141498 A1 | 5/2015 | Mutzke |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |

FOREIGN PATENT DOCUMENTS

| | | |
|---|---|---|
| WO | WO 2016465831 | 10/1916 |
| WO | WO 2016474227 | 11/1916 |
| WO | WO 2016474271 | 11/1916 |
| WO | WO 2016484575 | 11/1916 |
| WO | WO 2016484576 | 11/1916 |
| WO | WO 2016484822 | 11/1916 |
| WO | WO 2016-203025 | 12/1916 |
| WO | WO 2016493206 | 12/1916 |
| WO | WO 2016493226 | 12/1916 |
| WO | WO 2017-001058 | 1/1917 |
| WO | WO 2017-009376 | 1/1917 |
| WO | WO 2017-021546 | 2/1917 |
| WO | WO 2017-025120 | 2/1917 |
| WO | WO 2017-025447 | 2/1917 |
| WO | WO 2017-036580 | 3/1917 |
| WO | WO 1995-015394 | 6/1995 |
| WO | WO 1998-042856 | 10/1998 |
| WO | WO 2001-012824 | 2/2001 |
| WO | WO 2002-098443 | 12/2002 |
| WO | WO 2005/035771 | 4/2005 |
| WO | WO 2005-040377 | 5/2005 |
| WO | WO 2006-008154 | 1/2006 |
| WO | WO 2006-024518 | 3/2006 |
| WO | WO 2007-024708 | 3/2007 |
| WO | WO 2009-030481 | 3/2009 |
| WO | WO 2009-095226 | 8/2009 |
| WO | WO 2010-023260 | 3/2010 |
| WO | WO 2010-132867 | 11/2010 |
| WO | WO 2011-069529 | 6/2011 |
| WO | WO 2012-013326 | 2/2012 |
| WO | WO 2012-019630 | 2/2012 |
| WO | WO 2012-019780 | 2/2012 |
| WO | WO 2012416714 | 9/2012 |
| WO | WO 2013-120628 | 8/2013 |
| WO | WO 2013420626 | 8/2013 |
| WO | WO 2013420627 | 8/2013 |
| WO | WO 2015-024665 | 2/2015 |
| WO | WO 2015-024668 | 2/2015 |

OTHER PUBLICATIONS

Andries et al., "N1-nnethylpseudouridine-incorporated mRNA outperforms pseudouridine-incorporated mRNA by providing enhanced protein expression and reduced immunogenicity in mammalian cell lines and mice" 217 Journal of Controlled Release 337-344 (2015).*

Seidel et al., "Anti-PD-1 and Anti-CTLA-4 Therapies in Cancer: Mechanisms of Action, Efficacy, and Limitations" 8 Frontiers in Oncology Article 86 1-14 (Mar. 28, 2018).*

Attwood, "The babel of bioinformatics," *Science*, 290(5491):471-473, 2000.

Avni et al., "The 5' terminal oligopyrimidine tract confers translational control on TOP mRNAs in a cell type-and sequence context-dependent manner," *Nucleic Acids Research*, 25(5):995-1001, 1997.

Avni et al., "Vertebrate mRNAs with a 5'-terminal pyrimidine tract are candidates for translational repression in quiescent cells: characterization of the translational cis-regulatory element," *Mol. Cell. Biol.*, 14(6):3822-3833, 1994.

Battle and Doudna, "The stem-loop binding protein forms a highly stable and specific complex with the 3' stem-loop of histone mRNAs," *RNA*, 7:123-132, 2001.

Blumenthal et al., "Definition of an allergen (immunobiology)," *Allergens and Allergen Immunotherapy*, Ed. R. Lockey, S. Bukantz and J. Bousquet, pp. 37-50, 2004.

Caldarola et al., "Translational regulation of terminal oligopyrimidine mRNAs induced by serum and amino acids involves distinct signaling events," *The Journal of Biological Chemistry*, 279(14):13522-135531, 2004.

Cameron et al., "Recent advances in transgenic technology," *Molecular Biotechnology*, 7:253-265, 1997.

Chakrabarti et al., "The mammalian target of rapamycin complex 1 regulates leptin biosynthesis in adipocytes at the level of translation: the role of the 5'-untranslated region in the expression of leptin messenger ribonucleic acid," *Molecular Endocrinology*, 22(10):2260-2267, 2008.

Cheung et al., "Specific interaction of HeLa cell proteins with coxsackievirus B3 3'UTR: La autoantigen binds the 3' and 5' UTR independently of the poly(A) tail," *Cell Microbiol.*, 9(7):1705-1715, 2007.

Collart et al., "A human histone H2B.1 variant gene, located on chromosome 1, utilizes alternative 3' end processing," *Journal of Cellular Biochemistry*, 50:374-385, 1992.

Damgaard and Lykke-Andersen, "Translational coregulation of 5'TOP mRNAs by TIA-1 and TIAR," *Genes Dev.*, 25:2057-2068, 2011.

Database EMBL Accession No. EM_STD:AB063609, "Homosapiens RPL36AL mRNA for ribosomal protein L36a-like, complete cds," 2002.

Database Geneseq Accession No. ATN08647, "Human transcriptional regulatory element SEQ ID No. 6587," 2008.

Davuluri et al., "CART classification of human 5' UTR sequences," *Genome Research*, 10(11):1807-1816, 2000.

Deml et al., "Multiple effects of codon usage optimization on expression and immunogenicity of DNA candidate vaccines encoding the human immunodeficiency virus type 1 Gag protein," *Journal of Virology*, 75(22):10991-11001, 2001.

Dollé et al., "Nerve growth factor overexpression and autocrine loop in breast cancer cells," *Oncogene*, 22(36):5592-5601, 2003.

Dominski et al., "Stem-loop binding protein facilitates 3'-end formation by stabilizing U7 snRNP binding to histone pre-mRNA," *Mol Cell Biol.*, 19(5):3561-3570, 1999.

(56) References Cited

OTHER PUBLICATIONS

Eckner et al., "Mature mRNA 3' end formation stimulates RNA export from the nucleus," *The EMBO Journal*, 10(11):3513-3522, 1991.
Gallie et al., "The histone 3'-terminal stem-loop is necessary for translation in Chinese hamster ovary cells," *Nucleic Acids Res.*, 24(10):1954-1962, 1996.
Gerwitz et al., "Nucleic acid therapeutics: state of the art and future prospects," *Blood*, 92(3):712-736, 1998.
Ginn et al., "Gene therapy clinical trails worldwide to 2012—an update," *Journal of Gene Medicine*, 15:65-77, 2013.
Gorgoni et al., "The stem-loop binding protein stimulates histone translation at an early step in the initiation pathway," *RNA*, 11:1030-1042, 2005.
Haines et al., "CL22—a novel cationic peptide for efficient transfection of mammalian cells," *Gene Ther.*, 8:99-110, 2001.
Henke et al., "Coxsackievirus B3 vaccines: use as an expression vector for prevention of myocarditis," *Expert Rev. Vaccines*, 7(10):1557-1567, 2008.
Holtkamp et al., "Modification of antigen-encoding RNA increases stability, translational stimulatory capacity of dendritic cells," *Blood*, 108(13):4009-17, 2006.
Iadevaia et al., "All translation elongation factors and the e, f, and h subunits of translation initiation factor 3 are encoded by 5'-terminal oligopyrimidine (TOP) mRNAs," *RNA*, 14:1730-1736, 2008.
Kato et al., "Histone H2B as an antigen recognized by lung cancer-specific human monoclonal antibody HB4C5," *Human Antibodies and Hybridomas*, 2(2):94-101, 1991.
Kim et al., "Coxsackievirus B3 used as a gene therapy vector to express functional FGF2," *Gene Ther.*, 19(12):1159-1165, 2012.
Kim et al., "Systematic analysis of attenuated *Coxsackievirus* expressing a foreign gene as a viral vaccine vector," *Vaccine*, 28(5):1234-1240, 2010.
Knapinska et al., "Molecular mechanisms regulation mRNA stability: physiological and pathological significance," *Current Genomics*, 6(6):1-16, 2005.
Kramarova et al., "A sequence predicted to form a stem-loop is proposed to be required for formation of an RNA-protein complex involving the 3'UTR of β-subunit $F_0F_1$-ATPase mRNA," *Biochim. Biophys. Acta.*, 1777(7-8):747-757, 2008.
Kudla et al., "High guanine and cytosine content increases mRNA levels in mammalian cells," *PLoS Biology*, 4:0933-0942, 2006.
Ledda et al., "Effect of 3' UTR length on the translational regulation of 5'-terminal oligopyrimidine mRNAs," *Gene*, 344:213-220, 2005.
Levy et al., "Oligopyrimidine tract at the 5' end of mammalian ribosomal protein mRNAs is required for their translational control," *Proc. Natl. Acad. Sci. USA*, 88:3319-3323, 1991.
Levy et al., "Sequence and functional characterization of the terminal exon of the human insulin receptor gene," *Biochim Biophys Acta.*, 1263(3):253-257, 1995.
Ling et al., "The histone 3'-terminal stem-loop-binding protein enhances translation through a functional and physical interaction with eukaryotic initiation factor 4G (eIF4G) and eIF3," *Mol Cell Biol.*, 22:7853-7867, 2002.
Lopez and Samuelsson, "Early evolution of histone mRNA 3' end processing," *Bioinformatics*, 14(1):1-10, 2008.
Lorenzi et al., "Intranasal vaccination with messenger RNA as a new approach in gene therapy: use against tuberculosis," *BMC Biotechnology*, 10:77, 2010.
Meier et al., "Fibroblast growth factor-2 but not Mel-CAM and/or β3 integrin promotes progression of melanocytes to melanoma," *Exp. Dermatol.*, 12(3):296-306, 2003.
Meyuhas, "Synthesis of the translational apparatus is regulated at the translational level," *Eur. J. Biochem.*, 267:6321-6330, 2000.
Montoliu, "Gene transfer strategies in animal transgenesis," *Cloning and Stem Cells*, 4(1):39-46, 2002.
Narita et al., "NELF interacts with CDC and participates in 3' end processing of replication-dependent histone mRNAs," *Molecular Cell*, 26(3):349-365, 2007.
Ngo et al., "Computational complexity, protein structure prediction, and the levinthal paradox," *The Protein Folding Problem and Tertiary Structure Prediction*, Ed. K. Merz and S. Le Grand, pp. 491-495, 1994.
Niemann, "Transgenic farm animals get off the ground," *Transgenic Research*, 7:73-75, 1998.
Office Action issued in U.S. Appl. No. 13/321,474, dated Apr. 6, 2015.
Office Action issued in U.S. Appl. No. 13/321,474, dated May 20, 2014.
Office Action issued in U.S. Appl. No. 14/378,538, dated Jun. 21, 2016.
Office Action issued in U.S. Appl. No. 14/378,538, dated Nov. 12, 2015.
Office Action issued in U.S. Appl. No. 14/378,538, dated Oct. 11, 2016.
Office Action issued in U.S. Appl. No. 14/378,572, dated Aug. 12, 2016.
Office Action issued in U.S. Appl. No. 14/378,572, dated Mar. 3, 2016.
Office Action issued in U.S. Appl. No. 14/378,572, dated Mar. 14, 2017.
Office Action issued in U.S. Appl. No. 14/378,591, dated Aug. 22, 2016.
Office Action issued in U.S. Appl. No. 14/378,591, dated Jan. 27, 2017.
Office Action issued in U.S. Appl. No. 14/378,606, dated May 27, 2015.
Office Action issued in U.S. Appl. No. 14/378,606, dated Nov. 3, 2015.
Office Action issued in U.S. Appl. No. 14/388,224, dated Apr. 21, 2016.
Office Action issued in U.S. Appl. No. 14/388,224, dated Oct. 17, 2016.
Office Action issued in U.S. Appl. No. 14/388,226, dated Jun. 21, 2016.
Office Action issued in U.S. Appl. No. 14/388,226, dated Nov. 6, 2015.
Office Action issued in U.S. Appl. No. 14/945,349, dated Feb. 6, 2017.
Oliveira et al., "Inhibition of translational initiation in *Saccharomyces cerevisiae* by secondary structure: the roles of the stability and position of stem-loops in the mRNA leader," *Mol. Microbiol.*, 9(3):521-532, 1993.
Orom et al., "MicroRNA-10a binds the 5'UTR of ribosomal protein mRNAs and enhances their translation," *Molecular Cell*, 30:460-471, 2008.
Palmowski et al., "Intravenous injection of a lentiviral vector encoding NY-ESO-1 induces an effective CTL response," *J. Immunol.*, 172(3):1582-1587, 2004.
Pandey et al., "Introns in histone genes alter the distribution of 3' ends," *Nucleic Acids Res.*, 18(11):3161-3170, 1990.
PCT International Search Report and Written Opinion issued in International Application No. PCT/EP2013/000938, dated Nov. 13, 2013.
PCT International Search Report and Written Opinion issued in International Application No. PCT/EP2013/000461, dated Apr. 16, 2013.
PCT International Search Report and Written Opinion issued in International Application No. PCT/EP2013/000458, dated Apr. 24, 2013.
PCT International Search Report and Written Opinion issued in International Application No. PCT/EP2013/000459, dated Apr. 23, 2013.
PCT International Search Report and Written Opinion issued in International Application No. PCT/EP2013/000460, dated Apr. 22, 2013.
PCT International Search Report and Written Opinion issued in International Application No. PCT/EP2011/004077, dated Nov. 10, 2011.
PCT International Search Report and Written Opinion issued in International Application No. PCT/EP2013/000937, dated Aug. 30, 2013.

(56) References Cited

OTHER PUBLICATIONS

Prelle et al., "Establishment of pluripotent cell lines from vertebrate species—present status and future prospects," *Cells Tissues Organs*, 165:220-236, 1999.
Ristevski, "Making better transgenic models," *Molecular Biotechnology*, 29:153-163, 2005.
Roesler et al., "Immunize and disappear—safety-optimized mRNA vaccination with a panel of 29 allergens," *Journal of Allergy and Clinical Immunology*, 124(5):1070-1077, 2009.
Russell et al., "The stability of human beta-globin mRNA is dependent on structural determinants positioned within its 3' untranslated region," *Blood*, 87:5314-5323, 1996.
Sanchez et al., "Increased levels of polyadenylated histone H2B mRNA accumulate during *Entamoeba invadens* cyst formation," *Molecular and Biochemical Parasitology*, 67(1):137-146, 1994.
Sanchez et al., "The oligo(A) tail on histone mRNA plays an active role in translational silencing of histone mRNA during Xenopus oogenesis," *Mol Cell Biol.*, 24(6):2513-2525, 2004.
Sharma et al., "Functional role of the 5' terminal cloverleaf in Coxsackievirus RNA replication," *Virology*, 393(2):238-249, 2009.
Shen et al., "Structures required for poly(A) tail-independent translation overlap with, but ar distinct from, cap-independent translation and RNA replication signals at the 3' end of *Tobacco necrosis virus* RNA," *Virology*, 358:448-458, 2007.
Sigmund, "Viewpoint: are studies in genetically altered mice out of control?" *Arteriosclerosis, Thrombosis, and Vascular Biology*, 20:1425-1429, 2000.
Skolnick et al., "From genes to protein structure and function: novel applications of computational approaches in the genomic era," *Trends in Biotech.*, 18:34-39, 2000.
Smith, "Gene transfer in higher animals: theoretical considerations and key concepts," *Journal of Biotechnology*, 99:1-22, 2002.
Stauber et al., "A signal regulating mouse histone H4 mRNA levels in a mammalian cell cycle mutant and sequences controlling RNA 3' processing are both contained within the same 80-bp fragment," *EMBO J.*, 5(12):3297-3303, 1986.
Svoboda et al., "Hairpin RNA; a secondary structure of primary importance," *Cell Mol Life Sci.*, 63(7-8):901-908, 2006.
Thess et al., "Sequence-engineered mRNA without chemical nucleoside modifications enables an effective protein therapy in large animals," *Molecular Therapy*, pp. 1-9 and Supplementary Material, 2015.
Van Dijk et al., "Identification of RNA sequences and structures involved in site-specific cleavage of IGF-II mRNAs," *RNA*, 1623-1635, 1998.
van Ooij et al., "Polyadenylation of genomic RNA and initiation of antigenomic RNA in a positive-strand RNA virus are controlled by the same cis-element," *Nucleic Acids Res.*, 34(10):2953-2965, 2006.
Wagner et al., "A genome-wide RNA interference screen reveals that variant histones are necessary for replication-dependent histone pre-mRNA processing", *Molecular Cell*, 28(4):692-699, 2007.
Weiss et al., "Prophylactic mRNA vaccination against allergy," *Current Opinion in Allergy and Clinical Immunology*, 10(6):567-574, 2010.
Williams et al., "A simple, highly efficient method for heterologous expression in mammalian primary neurons using cationic lipid-mediated mRNA transfection," *Frontiers in Neuroscience*, 4:1-20, 2010.
Wooddell et al., "Sustained liver-specific transgene expression from the albumin prometer in mice following hydrodynamic plasmid DNA delivery," *The Journal of Gene Medicine*, 10:551-563, 2008.
Yamashita et al., "Comprehensive detection of human terminal oligo-pyrimidine (TOP) genes and analysis of their characteristics," *Nucleic Acids Res*, 36(11):3707-3715 and Supplementary Data (six pages), 2008.
Zhong et al., "A double-stranded RNA binding protein required for activation of repressed messages in mammalian germ cells," *Nat Genet.*, 22(2):171-174, 1999.
Zhu et al., "Binding of the La autoantigen to the 5' untranslated region of a chimeric human translation elongation factor 1A reporter mRNA inhibits translation in vitro," *Biochimica et Biophysica Acta*, 1521:19-29, 2001.
Dhamija et al., "Il-1-induced Post-transcriptional Mechanisms Target Overlapping Translational Silencing and Destabilizing Elements in IKBC mRNA," *J. Biol. Chem.*, 285(38):29165-29178, 2010.
Dugaiczyk et al., "Nucleotide sequence and the encoded amino acids of human serum albumin mRNA," *Proc. Natl. Acad. Sci. USA*, 79:71-75, 1982.
Kübler et al., "Self-adjuvanted mRNA vaccination in advanced prostate cancer patients: a first-in-man phase I/IIa study," *Journal of ImmunoTherapy of Cancer*, 3:26, 2015.
Office Action issued in U.S. Appl. No. 14/378,572, dated Sep. 21, 2017.
Office Action issued in U.S. Appl. No. 14/378,591, dated Apr. 9, 2018.
Office Action issued in U.S. Appl. No. 14/378,591, dated Aug. 23, 2017.
Office Action issued in U.S. Appl. No. 14/388,224, dated Jul. 28, 2017.
Office Action issued in U.S. Appl. No. 15/233,933, dated Apr. 6, 2018.
Office Action issued in U.S. Appl. No. 15/233,933, dated Dec. 7, 2017.
Office Action issued in U.S. Appl. No. 15/233,933, dated Jul. 28, 2017.
Office Action issued in U.S. Appl. No. 15/465,322, dated Apr. 2, 2018.
Office Action issued in U.S. Appl. No. 15/465,322, dated Nov. 20, 2017.
Office Action issued in U.S. Appl. No. 15/590,370, dated Apr. 30, 2018.
Shen and Higgins, "The 5' untranslated region-mediated enhancement of intracellular listeriolysin O production is required for *Listeria monocytogenes* pathogenicity," *Molecular Microbiology*, 57(5):1460-1473, 2005.
Thran et al., "mRNA mediates passive vaccination against infectious agents, toxins, and tumors," *EMBO Mol Med.*, 9:1434-1447, 2017.

* cited by examiner

| #A | #T | #C | #G | Cons | 99% | 95% | 90% | |
|---|---|---|---|---|---|---|---|---|
| 2224 | 172 | 1557 | 25 | N* | H* | M* | M* | |
| 1586 | 188 | 2211 | 16 | N* | H* | H* | M* | |
| 3075 | 47 | 875 | 4 | N | H | M | M | |
| 2872 | 205 | 918 | 6 | N | H | H | M | |
| 1284 | 19 | 2675 | 23 | N | V | M | M | |
| 184 | 6 | 270 | 3541 | N | V | S | S | ∧ |
| 0 | 0 | 0 | 4001 | G | G | G | G | ∧ |
| 13 | 569 | 3394 | 25 | N | Y | Y | Y | ∧ |
| 12 | 1620 | 2342 | 27 | N | Y | Y | Y | ∧ |
| 9 | 199 | 3783 | 10 | N | Y | Y | C | ∧ |
| 1 | 3947 | 51 | 2 | N | Y | T | T | ∧ |
| 47 | 3830 | 119 | 5 | N | H | T | T | • |
| 59 | 3704 | 227 | 11 | N | H | Y | T | • |
| 0 | 4001 | 0 | 0 | T | T | T | T | • |
| 675 | 182 | 3140 | 4 | N | H | M | M | • |
| 3818 | 1 | 7 | 175 | N | R | A | A | ∨ |
| 195 | 21 | 50 | 3735 | N | V | R | G | ∨ |
| 1596 | 15 | 31 | 2359 | N | V | R | R | ∨ |
| 523 | 11 | 16 | 3451 | N | R | R | R | ∨ |
| 0 | 0 | 4001 | 0 | C | C | C | C | ∨ |
| 14 | 179 | 3543 | 265 | N | B | S | S | ∨ |
| 3727 | 8 | 154 | 112 | N | V | M | A | |
| 61 | 64 | 3870 | 4 | N | H | C | C | |
| 771 | 557 | 2636 | 37 | N* | H* | H* | H* | |
| 2012 | 201 | 1744 | 43 | N* | N* | H* | M* | |
| 2499 | 690 | 674 | 138 | N* | N* | H* | H* | |

Stem 1: rows marked ∧
Loop: rows marked •
Stem 2: rows marked ∨

Figure 1

| #A | #T | #C | #G | Cons | 99% | 95% | 90% | | |
|---|---|---|---|---|---|---|---|---|---|
| 52 | 20 | 45 | 14 | N* | N* | N* | N* | | |
| 32 | 32 | 59 | 8 | N* | N* | N* | H* | | |
| 71 | 37 | 20 | 3 | N | N | H | H | | |
| 82 | 21 | 25 | 3 | N | N | H | H | | |
| 76 | 8 | 38 | 9 | N | N | N | V | | |
| 13 | 3 | 0 | 115 | D | D | R | R | ^ | ⎫ |
| 0 | 0 | 0 | 131 | G | G | G | G | ^ | ⎪ |
| 12 | 21 | 86 | 12 | N | N | N | N | ^ | ⎪ |
| 12 | 85 | 8 | 26 | N | N | N | D | ^ | ⎬ Stem 1 |
| 9 | 58 | 54 | 10 | N | N | N | B | ^ | ⎪ |
| 1 | 86 | 42 | 2 | N | B | Y | Y | ^ | ⎭ |
| 46 | 70 | 13 | 2 | N | N | H | H | · | ⎫ |
| 3 | 65 | 58 | 5 | N | N | B | Y | · | ⎬ Loop |
| 0 | 131 | 0 | 0 | T | T | T | T | · | ⎪ |
| 75 | 28 | 27 | 1 | N | H | H | H | · | ⎭ |
| 82 | 1 | 2 | 46 | N | V | R | R | v | ⎫ |
| 53 | 17 | 6 | 55 | N | N | D | D | v | ⎪ |
| 79 | 13 | 31 | 8 | N | N | N | H | v | ⎬ Stem 2 |
| 20 | 10 | 10 | 91 | N | N | N | N | v | ⎪ |
| 0 | 0 | 131 | 0 | C | C | C | C | v | ⎪ |
| 4 | 15 | 112 | 0 | H | H | Y | Y | v | ⎭ |
| 94 | 7 | 5 | 25 | N | N | D | R | | |
| 17 | 31 | 82 | 1 | N | H | H | H | | |
| 35 | 32 | 58 | 6 | N* | N* | H* | H* | | |
| 74 | 20 | 30 | 7 | N* | N* | N* | H* | | |
| 56 | 28 | 40 | 7 | N* | N* | N* | H* | | |

Figure 2

| 90% | 95% | 99% | Cons | #G | #C | #T | #A | |
|---|---|---|---|---|---|---|---|---|
| M* | H* | H* | N* | 8 | 601 | 63 | 661 | |
| M* | H* | H* | N* | 4 | 1062 | 121 | 146 | |
| A | A | M | H | 0 | 16 | 2 | 1315 | |
| A | A | A | N | 2 | 6 | 2 | 1323 | |
| M | M | M | N | 4 | 403 | 6 | 920 | |
| G | G | G | N | 1322 | 1 | 2 | 8 | ∧ |
| G | G | G | G | 1333 | 0 | 0 | 0 | ∧ |
| C | C | Y | H | 0 | 1293 | 39 | 1 | ∧ |
| T | Y | Y | Y | 0 | 116 | 1217 | 0 | ∧ |
| C | C | C | Y | 0 | 1331 | 2 | 0 | ∧ |
| T | T | T | Y | 0 | 2 | 1331 | 0 | ∧ |
| T | T | T | D | 3 | 0 | 1329 | 1 | . |
| T | Y | Y | N | 1 | 121 | 1207 | 4 | . |
| T | T | T | T | 0 | 0 | 1333 | 0 | . |
| M | M | H | H | 0 | 862 | 30 | 441 | . |
| A | A | A | A | 0 | 0 | 0 | 1333 | ∨ |
| G | G | G | B | 1330 | 2 | 1 | 0 | ∨ |
| R | R | R | R | 134 | 0 | 0 | 1199 | ∨ |
| G | G | R | D | 1311 | 0 | 1 | 21 | ∨ |
| C | C | C | C | 0 | 1333 | 0 | 0 | ∨ |
| C | C | C | N | 2 | 1328 | 2 | 1 | ∨ |
| M | V | V | N | 78 | 128 | 1 | 1126 | |
| C | C | H | N | 1 | 1284 | 22 | 26 | |
| Y* | H* | N* | N* | 18 | 1143 | 91 | 81 | |
| M* | H* | N* | N* | 28 | 834 | 91 | 380 | |
| M* | M* | M* | H* | 0 | 361 | 12 | 960 | |

Rows 6–11 labeled Stem 1; rows 12–15 labeled Loop; rows 16–21 labeled Stem 2.

Figure 4

| #A | #T | #C | #G | Cons | 99% | 95% | 90% | |
|---|---|---|---|---|---|---|---|---|
| 10 | 8 | 62 | 4 | N* | N* | H* | H* | |
| 17 | 6 | 61 | 0 | H* | H* | H* | M* | |
| 84 | 0 | 0 | 0 | A | A | A | A | |
| 84 | 0 | 0 | 0 | A | A | A | A | |
| 76 | 2 | 6 | 0 | H | H | W | W | |
| 1 | 2 | 0 | 81 | D | D | G | G | ⌐ |
| 0 | 0 | 0 | 84 | G | G | G | G | |
| 1 | 1 | 82 | 0 | H | H | C | C | |
| 0 | 67 | 17 | 0 | Y | Y | Y | Y | Stem 1 |
| 0 | 0 | 84 | 0 | C | C | C | C | |
| 0 | 84 | 0 | 0 | T | T | T | T | ⌐ |
| 1 | 80 | 0 | 3 | D | D | T | T | · |
| 0 | 81 | 3 | 0 | Y | Y | T | T | Loop |
| 0 | 84 | 0 | 0 | T | T | T | T | · |
| 12 | 5 | 67 | 0 | H | H | H | W | · |
| 84 | 0 | 0 | 0 | A | A | A | A | ⌐ |
| 0 | 0 | 1 | 83 | S | S | G | G | |
| 65 | 0 | 0 | 19 | R | R | R | R | Stem 2 |
| 3 | 0 | 0 | 81 | R | R | G | G | |
| 0 | 84 | 0 | 0 | C | C | C | C | |
| 0 | 84 | 0 | 0 | C | C | C | C | ⌐ |
| 69 | 0 | 5 | 10 | V | V | V | R | |
| 5 | 4 | 75 | 0 | H | H | H | M | |
| 0 | 25 | 57 | 2 | B* | B* | Y* | Y* | |
| 10 | 24 | 44 | 6 | N* | N* | N* | H* | |
| 64 | 3 | 17 | 0 | H* | H* | M* | M* | |

Figure 5 ppLuc(GC) – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagauc-3'

Figure 6 ppLuc(GC) – ag – A64 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAAA
AAAAAA-3'

Figure 7 ppLuc(GC) – ag – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucu<u>CAAAGGCUCUUUUCAGAGCCACCA</u>-3'

Figure 8 ppLuc(GC) – ag – A64 – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAA
AAAAAAugcauCAAAGGCUCUUUUCAGAGCCACCA-3′

Figure 9 ppLuc(GC) – ag – A120 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucuAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAA
AAAAAAAA-3′

Figure 10 ppLuc(GC) – ag – A64 – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGCGGCAAGAUCGCCGUGAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcauCCUGCCCGAUGGGCCUCCCAACGGGCCCUCCUCCCCUCCUUGCACCG3'

Figure 11 ppLuc(GC) – ag – A64 – aCPSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGCGGCAAGAUCGCCGUGAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAugcau*CAAUUCCUACACGUGAGGCGCUGUGAUUCCCUAUCCCCCUUCAUUCCCU*
*AUACAUUAGCACAGCGCCAUUGCAUGUAGGAAUU*-3'

Figure 12 ppLuc(GC) – ag – A64 – PolioCL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGCGGCAAGAUCGCCGUGAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*CAAUUCUAAAACAGCUCUGGGGUUGUACCCACCCCAGAGGCCCACGUGG
CGGCUAGUACUCCGGUAUUGCGGUACCCUUGUACGCCUGUUUUAGAAUU-3'* ppLuc(GC) – ag – A64 – G30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAAA
AAAAAAugcau*GGGGGGGGGGGGGGGGGGGGGGGGGGGGGG*-3'

Figure 14 ppLuc(GC) – ag – A64 – U30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAAA
AAAAAAugca*UUUUUUUUUUUUUUUUUUUUUUUUUUUUUU*-3'

Figure 15 ppLuc(GC) – ag – A64 – SL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*UAUGGCGGCCGUGUCCACCACGGAUAUCACCGUGGUGGACGCGGCC*-3'

Figure 16 ppLuc(GC) – ag – A64 – N32 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAAA
AAAAAAugcau*CCCCCUCUAGACAAUUGGAAUUCCAUA*-3'

Figure 17

MmEPO(GC) – ag – A64 – C30 gggagaaagcuuaccAUGGGCGUGCCCGAGCGGCCGACCCUGCUCCUGCUGCUCAGCCUG
CUGCUCAUCCCCUGGGGCUGCCCGUCCUCUGCGCCCCCCGCGCCUGAUCUGCGACUCC
CGGGUGCUGGAGCGCUACAUCCUCGAGGCCAAGGAGGCGGAGAACGUGACCAUGGGCUGC
GCCGAGGGGCCCCGGCUGAGCGAGAACAUCACGGUCCCCGACACCAAGGUGAACUUCUAC
GCCUGGAAGCGCAUGGAGGUGGAGGAGCAGGCCAUCGAGGUCUGGCAGGGCCUGUCCCUC
CUGAGCGAGGCCAUCCUGCAGGCGCAGGCCCUCCUGGCCAACUCCAGCCAGCCCCCGGAG
ACACUGCAGCUCCACAUCGACAAGGCCAUCUCCGGGCUGCGGAGCCUGACCUCCCUCCUG
CGCGUGCUGGGCGCGCAGAAGGAGCUCAUGAGCCCGCCCGACACGACCCCCCGGCCCCG
CUGCGGACCCUGACCGUGGACACGUUCUGCAAGCUCUUCCGCGUCUACGCCAACUUCCUG
CGGGGCAAGCUGAAGCUCUACACCGGGGAGGUGUGCCGCCGGGGCGACCGCUGACCACUA
GUUAUAAGACUGACUAGCCCGAUGGGCCUCCCAACGGGCCCUCCUCCCCUCCUUGCACCG
agauuaauAAAAAAAAAAAAAAAAAAAAAAAAAAAAAAAAAAAAAAAAAAAAAAAAAAAA
AAAAAAAAAAAAuauuCCCCCCCCCCCCCCCCCCCCCCCCCCCCCCucuag

Figure 18

MmEPO(GC) – ag – A64 – C30 - histoneSL gggagaaagcuuaccAUGGGCGUGCCCGAGCGGCCGACCCUGCUCCUGCUGCUCAGCCUG
CUGCUCAUCCCCCUGGGGCUGCCCGUCCUCUGCGCCCCCCGCGCCUGAUCUGCGACUCC
CGGGUGCUGGAGCGCUACAUCCUCGAGGCCAAGGAGGCGGAGAACGUGACCAUGGGCUGC
GCCGAGGGGCCCCGGCUGAGCGAGAACAUCACGGUCCCCGACACCAAGGUGAACUUCUAC
GCCUGGAAGCGCAUGGAGGUGGAGGAGCAGGCCAUCGAGGUCUGGCAGGGCCUGUCCCUC
CUGAGCGAGGCCAUCCUGCAGGCGCAGGCCCUCCUGGCCAACUCCAGCCAGCCCCCGGAG
ACACUGCAGCUCCACAUCGACAAGGCCAUCUCCGGGCUGCGGAGCCUGACCUCCCUCCUG
CGCGUGCUGGGCGCGCAGAAGGAGCUCAUGAGCCCGCCCGACACGACCCCCCCGGCCCCG
CUGCGGACCCUGACCGUGGACACGUUCUGCAAGCUCUUCCGCGUCUACGCCAACUUCCUG
CGGGGCAAGCUGAAGCUCUACACCGGGGAGGUGUGCCGCCGGGCGACCGCUGAccacua
guuauaagacugacua**GCCCGAUGGGCCUCCCAACGGGCCCUCCUCCCCUCCUUGCACCG
AGAUUAAU**AAAAAAAAAAAAAAAAAAAAAAAAAAAAAAAAAAAAAAAAAAAAAAAAAAAA
AAAAAAAAAAAAugcauCCCCCCCCCCCCCCCCCCCCCCCCCCCCCCC<u>CAAAGGCUCUUUU
CAGAGCCACCA</u>gaauu

Figure 19

Trastuzumab(GC) – ag – A64 –C30 gggagaaagcuuaccAUGGCCGUGAUGGCGCCGCGGACCCUGGUCCUCCUGCUGAGCGGCGC
CCUCGCCCUGACGCAGACCUGGGCCGGGGAGGUGCAGCUGGUCGAGAGCGGCGGGGGCCUCG
UGCAGCCGGGCGGGUCGCUGCGGCUGAGCUGCGCCGCGAGCGGGUUCAACAUCAAGGACACC
UACAUCCACUGGGUGCGCCAGGCCCCCGGCAAGGGCCUCGAGUGGGUCGCCCGGAUCUACCC
CACGAACGGGUACACCCGCUACGCCGACAGCGUGAAGGGCCGGUUCACCAUCAGCGCGGACA
CCUCGAAGAACACGGCCUACCUGCAGAUGAACAGCCUGCGCGCCGAGGACACCGCCGUGUAC
UACUGCAGCCGGUGGGGCGGCGACGGGUUCUACGCCAUGGACUACGGGGGCAGGGCACCCU
CGUCACCGUGAGCAGCGCGUCGACGAAGGGGCCCAGCGUGUUCCCGCUGGCCCCCAGCAGCA
AGAGCACCAGCGGCGGGACCGCCGCCCUGGGCUGCCUCGUCAAGGACUACUUCCCCGAGCCC
GUGACCGUGUCGUGGAACAGCGGCGCGCUGACGAGCGGGGUCCACACCUUCCCGGCCGUGCU
GCAGAGCAGCGGCCUCUACUCGCUGAGCAGCGUGGUCACCGUGCCCAGCAGCAGCCUGGGGA
CCCAGACGUACAUCUGCAACGUGAACCACAAGCCCUCGAACACCAAGGUCGACAAGAAGGUG
GAGCCCCCGAAGAGCUGCGACAAGACCCACACCUGCCCGCCCUGCCCCGCCCCCGAGCUCCU
GGGCGGGCCCAGCGUGUUCCUGUUCCCGCCCAAGCCCAAGGACACGCUCAUGAUCAGCCGCA
CCCCCGAGGUCACCUGCGUGGUGGUCGACGUGAGCCACGAGGACCCCGAGGUGAAGUUCAAC
UGGUACGUCGACGGCGUGGAGGUGCACAACGCCAAGACCAAGCCGCGGGAGGAGCAGUACAA
CUCGACGUACCGCGUCGUGAGCGUGCUGACCGUCCUGCACCAGGACUGGCUCAACGGCAAGG
AGUACAAGUGCAAGGUGAGCAACAAGGCCCUGCCCGCGCCCAUCGAGAAGACCAUCAGCAAG
GCCAAGGGGCAGCCCCGGGAGCCGCAGGUGUACACCCUGCCCCCCAGCCGCGACGAGCUCAC
GAAGAACCAGGUCAGCCUGACCUGCCUGGUGAAGGGCUUCUACCCCUCGGACAUCGCCGUGG
AGUGGGAGAGCAACGGGCAGCCGGAGAACAACUACAAGACCACCCCGCCCGUCCUCGACAGC
GACGGCAGCUUCUUCCUGUACAGCAAGCUGACGGUGGACAAGUCGCGGUGGCAGCAGGGCAA
CGUGUUCAGCUGCAGCGUCAUGCACGAGGCCCUCCACAACCACUACACCCAGAAGAGCCUGA
GCCUGAGCCCCGGGAAGCAUCAUCAUCAUCAUCAUUGACCAUGCAUUUGAAAGCCGGGGGUG
GGAGAUCCGGAUUGCCAGUCUGCUCGAUAUCGCAGGCUGGGUCCGUGACUACCCACUCCCCC
UUUAAUUCCGCCCCUCUCCCUCCCCCCCCCUAACGUUACUGGCCGAAGCCGCUUGGAAUAA
GGCCGGUGUGCGUUUGUCUAUAUGUUAUUUUCCACCAUAUUGCCGUCUUUUGGCAAUGUGAG
GGCCCGGAAACCUGGCCCUGUCUUCUUGACGAGCAUUCCUAGGGGUCUUUCCCCUCUCGCCA
AAGGAAUGCAAGGUCUGUUGAAUGUCGUGAAGGAAGCAGUUCCUCUGGAAGCUUCUUGAAGA
CAAACAACGUCUGUAGCGACCCUUUGCAGGCAGCGGAACCCCCCACCUGGCGACAGGUGCCU
CUGCGGCCAAAAGCCACGUGUAUAAGAUACACCUGCAAAGGCGGCACAACCCCAGUGCCACG
UUGUGAGUUGGAUAGUUGUGGAAAGAGUCAAAUGGCUCUCCUCAAGCGUAUUCAACAAGGGG
CUGAAGGAUGCCCAGAAGGUACCCCAUUGUAUGGGAUCUGAUCUGGGGCCUCGGUGCACAUG
CUUUACGUGUGUUUAGUCGAGGUUAAAAAACGUCUAGGCCCCCCGAACCACGGGGACGUGGU
UUUCCUUUGAAAAACACGAUGAUAAUAGAUCUACCAUGGCCGUGAUGGCGCCGCGGACCCUG
GUCCUCCUGCUGAGCGGCGCCCUCGCCCUGACGCAGACCUGGGCCGGGGACAUCCAGAUGAC
CCAGAGCCCGUCGAGCCUGAGCGCCAGCGUGGGCGACCGGGUCACGAUCACCUGCCGCGCGA
GCCAGGACGUGAACACCGCCGUGGCCUGGUACCAGCAGAAGCCCGGGAAGGCCCCCAAGCUC
CUGAUCUACUCGGCGAGCUUCCUGUACAGCGGCGUCCCCAGCCGGUUCAGCGGGUCGCGCAG
CGGCACCGACUUCACGCUCACCAUCAGCAGCCUGCAGCCGGAGGACUUCGCCACCUACUACU
GCCAGCAGCACUACACCACGCCCCCACCUUCGGGCAGGGCACCAAGGUGGAGAUCAAGCGG
ACCGUGGCCGCCCCCAGCGUCUUCAUCUUCCCGCCCAGCGACGAGCAGCUGAAGUCGGGCAC
GGCCAGCGUGGUGUGCCUCCUGAACAACUUCUACCCCGCGAGGCGAAGGUCCAGUGGAAGG
UGGACAACGCCCUGCAGAGCGGGAACAGCCAGGAGAGCGUGACCGAGCAGGACUCGAAGGAC
AGCACCUACAGCCUCAGCAGCACCCUGACGCUGAGCAAGGCCGACUACGAGAAGCACAAGGU
CUACGCCUGCGAGGUGACCCACCAGGGGCUCUCGAGCCCCGUGACCAAGAGCUUCAACCGGG
GCGAGUGCUGAccacuaguuauaagacugacua**GCCCGAUGGGCCUCCCAACGGGCCCUCCU
CCCCUCCUUGCACCG**agauuaauAAAAAAAAAAAAAAAAAAAAAAAAAAAAAAAAAAAAAA
AAAAAAAAAAAAAAAAAAAAAAAAAAuauuCCCCCCCCCCCCCCCCCCCCCCCCCCCCCucu
ag

Figure 24

Trastuzumab(GC) – ag – A64 –C30 – histoneSL gggagaaagcuuaccAUGGCCGUGAUGGCGCCGCGGACCCUGGUCCUCCUGCUGAGCGGCGC
CCUCGCCCUGACGCAGACCUGGGCCGGGGAGGUGCAGCUGGUCGAGAGCGGCGGGGGCCUCG
UGCAGCCGGGCGGGUCGCUGCGGCUGAGCUGCGCCGCGAGCGGGUUCAACAUCAAGGACACC
UACAUCCACUGGGUGCGCCAGGCCCCCGGCAAGGGCCUCGAGUGGGUCGCCCGGAUCUACCC
CACGAACGGGUACACCCGCUACGCCGACAGCGUGAAGGGCCGGUUCACCAUCAGCGCGGACA
CCUCGAAGAACACGGCCUACCUGCAGAUGAACAGCCUGCGCGCCGAGGACACCGCCGUGUAC
UACUGCAGCCGGUGGGGCGGCGACGGGUUCUACGCCAUGGACUACGGGGGCAGGGCACCCU
CGUCACCGUGAGCAGCGCGUCGACGAAGGGGCCCAGCGUGUUCCCGCUGGCCCCCAGCAGCA
AGAGCACCAGCGGCGGGACCGCCGCCCUGGGCUGCCUCGUCAAGGACUACUUCCCCGAGCCC
GUGACCGUGUCGUGGAACAGCGGCGCGCUGACGAGCGGGGUCCACACCUUCCCGGCCGUGCU
GCAGAGCAGCGGCCUCUACUCGCUGAGCAGCGUGGUCACCGUGCCCAGCAGCAGCCUGGGGA
CCCAGACGUACAUCUGCAACGUGAACCACAAGCCCUCGAACACCAAGGUCGACAAGAAGGUG
GAGCCCCCGAAGAGCUGCGACAAGACCCACACCUGCCCGCCCUGCCCCGCCCCCGAGCUCCU
GGGCGGGCCCAGCGUGUUCCUGUUCCCGCCCAAGCCCAAGGACACGCUCAUGAUCAGCCGCA
CCCCCGAGGUCACCUGCGUGGUGGUCGACGUGAGCCACGAGGACCCCGAGGUGAAGUUCAAC
UGGUACGUCGACGGCGUGGAGGUGCACAACGCCAAGACCAAGCCGCGGGAGGAGCAGUACAA
CUCGACGUACCGCGUCGUGAGCGUGCUGACCGUCCUGCACCAGGACUGGCUCAACGGCAAGG
AGUACAAGUGCAAGGUGAGCAACAAGGCCCUGCCCGCGCCCAUCGAGAAGACCAUCAGCAAG
GCCAAGGGGCAGCCCCGGGAGCCGCAGGUGUACACCCUGCCCCCAGCCGCGACGAGCUCAC
GAAGAACCAGGUCAGCCUGACCUGCCUGGUGAAGGGCUUCUACCCCUCGGACAUCGCCGUGG
AGUGGGAGAGCAACGGGCAGCCGGAGAACAACUACAAGACCACCCCGCCCGUCCUCGACAGC
GACGGCAGCUUCUUCCUGUACAGCAAGCUGACGGUGGACAAGUCGCGGUGGCAGCAGGGCAA
CGUGUUCAGCUGCAGCGUCAUGCACGAGGCCCUCCACAACCACUACACCCAGAAGAGCCUGA
GCCUGAGCCCCGGGAAGCAUCAUCAUCAUCAUCAUUGACCAUGCAUUUGAAAGCCGGGGGUG
GGAGAUCCGGAUUGCCAGUCUGCUCGAUAUCGCAGGCUGGGUCCGUGACUACCCACUCCCCC
UUUAAUUCCGCCCCUCUCCCUCCCCCCCCCUAACGUUACUGGCCGAAGCCGCUUGGAAUAA
GGCCGGUGUGCGUUUGUCUAUAUGUUAUUUUCCACCAUAUUGCCGUCUUUUGGCAAUGUGAG
GGCCCGGAAACCUGGCCCUGUCUUCUUGACGAGCAUUCCUAGGGGUCUUUCCCCUCUCGCCA
AAGGAAUGCAAGGUCUGUUGAAUGUCGUGAAGGAAGCAGUUCCUCUGGAAGCUUCUUGAAGA
CAAACAACGUCUGUAGCGACCCUUUGCAGGCAGCGGAACCCCCCACCUGGCGACAGGUGCCU
CUGCGGCCAAAAGCCACGUGUAUAAGAUACACCUGCAAAGGCGGCACAACCCCAGUGCCACG
UUGUGAGUUGGAUAGUUGUGGAAAGAGUCAAAUGGCUCUCCUCAAGCGUAUUCAACAAGGGG
CUGAAGGAUGCCCAGAAGGUACCCCAUUGUAUGGGAUCUGAUCUGGGGCCUCGGUGCACAUG
CUUUACGUGUGUUUAGUCGAGGUUAAAAAACGUCUAGGCCCCCCGAACCACGGGGACGUGGU
UUUCCUUUGAAAAACACGAUGAUAAUAGAUCUACCAUGGCCGUGAUGGCGCCGCGGACCCUG
GUCCUCCUGCUGAGCGGCGCCCUCGCCCUGACGCAGACCUGGGCCGGGGACAUCCAGAUGAC
CCAGAGCCCGUCGAGCCUGAGCGCCAGCGUGGGCGACCGGGUCACGAUCACCUGCCGCGCGA
GCCAGGACGUGAACACCGCCGUGGCCUGGUACCAGCAGAAGCCCGGGAAGGCCCCCAAGCUC
CUGAUCUACUCGGCGAGCUUCCUGUACAGCGGCGUCCCCAGCCGGUUCAGCGGGUCGCGCAG
CGGCACCGACUUCACGCUCACCAUCAGCAGCCUGCAGCCGGAGGACUUCGCCACCUACUACU
GCCAGCAGCACUACACCACGCCCCCACCUUCGGGCAGGGCACCAAGGUGGAGAUCAAGCGG
ACCGUGGCCGCCCCCAGCGUCUUCAUCUUCCCGCCCAGCGACGAGCAGCUGAAGUCGGGCAC
GGCCAGCGUGGUGUGCCUCCUGAACAACUUCUACCCCGCGAGGCGAAGGUCCAGUGGAAGG
UGGACAACGCCCUGCAGAGCGGGAACAGCCAGGAGAGCGUGACCGAGCAGGACUCGAAGGAC
AGCACCUACAGCCUCAGCAGCACCCUGACGCUGAGCAAGGCCGACUACGAGAAGCACAAGGU
CUACGCCUGCGAGGUGACCCACCAGGGGCUCUCGAGCCCCGUGACCAAGAGCUUCAACCGGG
GCGAGUGCUGAccacuaguuauaagacugacua**GCCCGAUGGGCCUCCCAACGGGCCCUCCU
CCCCUCCUUGCACCG**AGAUUAAUAAAAAAAAAAAAAAAAAAAAAAAAAAAAAAAAAAAAAAA
AAAAAAAAAAAAAAAAAAAAAAAAugcauCCCCCCCCCCCCCCCCCCCCCCCCCCCCCCCCA
AAGGCUCUUUUCAGAGCCACCAgaauu

Figure 25

NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED THERAPEUTIC PROTEIN

This application is a continuation of U.S. application Ser. No. 15/233,933, filed Aug. 10, 2016, which is a continuation of U.S. application Ser. No. 14/378,606, filed Aug. 13, 2014, now U.S. Pat. No. 9,447,431, which is a national phase application under 35 U.S.C. § 371 of International Application No. PCT/EP2013/000461, filed Feb. 15, 2013, which is a continuation of International Application No. PCT/EP2012/000671, filed Feb. 15, 2012. The entire text of each of the above referenced disclosures is specifically incorporated herein by reference.

The present invention relates to a nucleic acid sequence, comprising or coding for a coding region, encoding at least one peptide or protein comprising a therapeutic protein or a fragment, variant or derivative thereof, at least one histone stem-loop and a poly(A) sequence or a polyadenylation signal. Furthermore, the present invention provides the use of the nucleic acid for increasing the expression of said encoded peptide or protein, particularly for the use in gene therapy. It also discloses its use for the preparation of a pharmaceutical composition, e.g. for use in gene therapy, particularly in the treatment of diseases which are in need of a treatment with a therapeutic peptide or protein, preferably as defined herein. The present invention further describes a method for increasing the expression of a peptide or protein comprising a therapeutic protein or a fragment, variant or derivative thereof, using the nucleic acid comprising or coding for a histone stem-loop and a poly(A) sequence or a polyadenylation signal.

Gene therapy means the use of nucleic acids as a pharmaceutical agent to treat a disease. It derives its name from the idea that nucleic acids can be used to supplement or alter the expression of a gene within an individual's cells as a therapy to treat a disease. The most common form of gene therapy involves using nucleic acids that encode a functional, therapeutic protein in order to replace a mutated gene. Other forms involve direct correction of a mutation, or using nucleic acids that encode a therapeutic protein drug to provide treatment.

Gene therapy is a method of molecular medicine which already has been proven in the therapy and prevention of diseases and generally exhibits a considerable effect on daily medical practice, in particular on the treatment of diseases as mentioned herein. Gene therapy is based on the introduction of nucleic acids into the patient's cells or tissue and subsequent processing of the information coded for by the nucleic acid that has been introduced into the cells or tissue, that is to say the (protein) expression of the desired polypeptides.

Gene therapy may be beneficial for a lot of inherited or acquired diseases, inter alia infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system.

In gene therapy approaches, typically DNA is used even though RNA is also known in recent developments. Importantly, in all these gene therapy approaches mRNA functions as messenger for the sequence information of the encoded protein, irrespectively if DNA, viral RNA or mRNA is used.

In general RNA is considered an unstable molecule: RNases are ubiquitous and notoriously difficult to inactivate. Furthermore, RNA is also chemically more labile than DNA. Thus, it is perhaps surprising that the "default state" of an mRNA in a eukaryotic cell is characterized by a relative stability and specific signals are required to accelerate the decay of individual mRNAs. The main reason for this finding appears to be that mRNA decay within cells is catalyzed almost exclusively by exonucleases. However, the ends of eukaryotic mRNAs are protected against these enzymes by specific terminal structures and their associated proteins: a m7GpppN CAP at the 5' end and typically a poly(A) sequence at the 3' end. Removal of these two terminal modifications is thus considered rate limiting for mRNA decay. Although a stabilizing element has been characterized in the 3' UTR of the alpha-globin mRNA, RNA sequences affecting turnover of eukaryotic mRNAs typically act as a promoter of decay usually by accelerating deadenylation (reviewed in Meyer, S., C. Temme, et al. (2004), Crit Rev Biochem Mol Biol 39(4): 197-216.).

As mentioned above, the 5' ends of eukaryotic mRNAs are typically modified posttranscriptionally to carry a methylated CAP structure, e.g. m7GpppN. Aside from roles in RNA splicing, stabilization, and transport, the CAP structure significantly enhances the recruitment of the 40S ribosomal subunit to the 5' end of the mRNA during translation initiation. The latter function requires recognition of the CAP structure by the eukaryotic initiation factor complex eIF4F. The poly(A) sequence additionally stimulates translation via increased 40S subunit recruitment to mRNAs, an effect that requires the intervention of poly(A) binding protein (PABP). PABP, in turn, was recently demonstrated to interact physically with eIF4G, which is part of the CAP-bound eIF4F complex. Thus, a closed loop model of translation initiation on capped, polyadenylated mRNAs was postulated (Michel, Y. M., D. Poncet, et al. (2000), J Biol Chem 275(41): 32268-76.).

Nearly all eukaryotic mRNAs end with such a poly(A) sequence that is added to their 3' end by the ubiquitous cleavage/polyadenylation machinery. The presence of a poly (A) sequence at the 3' end is one of the most recognizable features of eukaryotic mRNAs. After cleavage, most pre-mRNAs, with the exception of replication-dependent histone transcripts, acquire a polyadenylated tail. In this context, 3' end processing is a nuclear co-transcriptional process that promotes transport of mRNAs from the nucleus to the cytoplasm and affects the stability and the translation of mRNAs. Formation of this 3' end occurs in a two step reaction directed by the cleavage/polyadenylation machinery and depends on the presence of two sequence elements in mRNA precursors (pre-mRNAs); a highly conserved hexanucleotide AAUAAA (polyadenylation signal) and a downstream G/U-rich sequence. In a first step, pre-mRNAs are cleaved between these two elements. In a second step tightly coupled to the first step the newly formed 3' end is extended by addition of a poly(A) sequence consisting of 200-250 adenylates which affects subsequently all aspects of mRNA metabolism, including mRNA export, stability and translation (Dominski, Z. and W. F. Marzluff (2007), Gene 396(2): 373-90.).

The only known exception to this rule are the replication-dependent histone mRNAs which end with a histone stem-loop instead of a poly(A) sequence. Exemplary histone stem-loop sequences are described in Lopez et al. (Dávila López, M., & Samuelsson, T. (2008), RNA (New York, N.Y.), 14(1), 1-10. doi:10.1261/rna.782308.).

The stem-loops in histone pre-mRNAs are typically followed by a purine-rich sequence known as the histone downstream element (HDE). These pre-mRNAs are processed in the nucleus by a single endonucleolytic cleavage approximately 5 nucleotides downstream of the stem-loop, catalyzed by the U7 snRNP through base pairing of the U7 snRNA with the HDE. The 3'-UTR sequence comprising the histone stem-loop structure and the histone downstream element (HDE) (binding site of the U7 snRNP) were usually termed as histone 3'-processing signal (see e.g. Chodchoy, N., N. B. Pandey, et al. (1991). Mol Cell Biol 11(1): 497-509.).

Due to the requirement to package newly synthesized DNA into chromatin, histone synthesis is regulated in concert with the cell cycle. Increased synthesis of histone proteins during S phase is achieved by transcriptional activation of histone genes as well as posttranscriptional regulation of histone mRNA levels. It could be shown that the histone stem-loop is essential for all posttranscriptional steps of histone expression regulation. It is necessary for efficient processing, export of the mRNA into the cytoplasm, loading onto polyribosomes, and regulation of mRNA stability.

In the above context, a 32 kDa protein was identified, which is associated with the histone stem-loop at the 3'-end of the histone messages in both the nucleus and the cytoplasm. The expression level of this stem-loop binding protein (SLBP) is cell-cycle regulated and is highest during S-phase when histone mRNA levels are increased. SLBP is necessary for efficient 3'-end processing of histone pre-mRNA by the U7 snRNP. After completion of processing, SLBP remains associated with the stem-loop at the end of mature histone mRNAs and stimulates their translation into histone proteins in the cytoplasm. (Dominski, Z. and W. F. Marzluff (2007), Gene 396(2): 373-90). Interestingly, the RNA binding domain of SLBP is conserved throughout metazoa and protozoa (Dávila López, M., & Samuelsson, T. (2008), RNA (New York, N.Y.), 14(1), 1-10. doi:10.1261/rna.782308) and it could be shown that its binding to the histone stem-loop sequence is dependent on the stem-loop structure and that the minimum binding site contains at least 3 nucleotides 5' and 2 nucleotides 3' of the stem-loop (Pandey, N. B., et al. (1994), *Molecular and Cellular Biology*, 14(3), 1709-1720 and Williams, A. S., & Marzluff, W. F., (1995), *Nucleic Acids Research*, 23(4), 654-662.).

Even though histone genes are generally classified as either "replication-dependent", giving rise to mRNA ending in a histone stem-loop, or "replacement-type", giving rise to mRNA bearing a poly(A)-tail instead, naturally occurring mRNAs containing both a histone stem-loop and poly(A) or oligo(A) 3' thereof have been identified in some very rare cases. Sanchez et al. examined the effect of naturally occurring oligo(A) tails appended 3' of the histone stem-loop of histone mRNA during Xenopus oogenesis using Luciferase as a reporter protein and found that the oligo(A) tail is an active part of the translation repression mechanism that silences histone mRNA during oogenesis and its removal is part of the mechanism that activates translation of histone mRNAs (Sanchez, R. and W. F. Marzluff (2004), Mol Cell Biol 24(6): 2513-25).

Furthermore, the requirements for regulation of replication dependent histones at the level of pre-mRNA processing and mRNA stability have been investigated using artificial constructs coding for the marker protein alpha Globin, taking advantage of the fact that the globin gene contains introns as opposed to the intron-less histone genes. For this purpose constructs were generated in which the alpha globin coding sequence was followed by a histone stem-loop signal (histone stem-loop followed by the histone downstream element) and a polyadenylation signal (Whitelaw, E., et al. (1986). Nucleic Acids Research, 14(17), 7059-7070.; Pandey, N. B., & Marzluff, W. F. (1987). Molecular and Cellular Biology, 7(12), 4557-4559.; Pandey, N. B., et al. (1990). Nucleic Acids Research, 18(11), 3161-3170).

In another approach Lüscher et al. investigated the cell-cycle dependent regulation of a recombinant histone H4 gene. Constructs were generated in which the H4 coding sequence was followed by a histone stem-loop signal and a polyadenylation signal, the two processing signals incidentally separated by a galactokinase coding sequence (Lüscher, B. et al., (1985). Proc. Natl. Acad. Sci. USA, 82(13), 4389-4393).

Additionally, Stauber et al. identified the minimal sequence required to confer cell-cycle regulation on histone H4 mRNA levels. For these investigations constructs were used, comprising a coding sequence for the selection marker Xanthine:guanine phosphoribosyl transferase (GPT) preceding a histone stem-loop signal followed by a polyadenylation signal (Stauber, C. et al., (1986). EMBO J, 5(12), 3297-3303).

Examining histone pre-mRNA processing Wagner et al. identified factors required for cleavage of histone pre-mRNAs using a reporter construct placing EGFP between a histone stem-loop signal and a polyadenylation signal, such that EGFP was expressed only in case histone pre-mRNA processing was disrupted (Wagner, E. J. et al., (2007). Mol Cell 28(4), 692-9).

To be noted, translation of polyadenylated mRNA usually requires the 3' poly(A) sequence to be brought into proximity of the 5' CAP. This is mediated through protein-protein interaction between the poly(A) binding protein and eukaryotic initiation factor eIF4G. With respect to replication-dependent histone mRNAs, an analogous mechanism has been uncovered. In this context, Gallie et al. show that the histone stem-loop is functionally similar to a poly(A) sequence in that it enhances translational efficiency and is co-dependent on a 5'-CAP in order to establish an efficient level of translation. They showed that the histone stem-loop is sufficient and necessary to increase the translation of a reporter mRNA in transfected Chinese hamster ovary cells but must be positioned at the 3'-terminus in order to function optimally. Therefore, similar to the poly(A) tail on other mRNAs, the 3' end of these histone mRNAs appears to be essential for translation in vivo and is functionally analogous to a poly(A) tail (Gallie, D. R., Lewis, N. J., & Marzluff, W. F. (1996), Nucleic Acids Research, 24(10), 1954-1962).

Additionally, it could be shown that SLBP is bound to the cytoplasmic histone mRNA and is required for its translation. Even though SLBP does not interact directly with eIF4G, the domain required for translation of histone mRNA interacts with the recently identified protein SLIP1. In a further step, SLIP1 interacts with eIF4G and allows to circularize histone mRNA and to support efficient translation of histone mRNA by a mechanism similar to the translation of polyadenylated mRNAs.

As mentioned above, gene therapy approaches normally use DNA to transfer the coding information into the cell which is then transcribed into mRNA, carrying the naturally occurring elements of an mRNA, particularly the 5'-CAP structure and the 3' poly(A) sequence to ensure expression of the encoded therapeutic or antigenic protein.

However, in many cases expression systems based on the introduction of such nucleic acids into the patient's cells or tissue and the subsequent expression of the desired polypeptides coded for by these nucleic acids do not exhibit the desired, or even the required, level of expression which may allow for an efficient therapy, irrespective as to whether DNA or RNA is used.

In the prior art, different attempts have hitherto been made to increase the yield of the expression of an encoded protein, in particular by use of improved expression systems, both in vitro and/or in vivo. Methods for increasing expression described generally in the prior art are conventionally based on the use of expression vectors or cassettes containing specific promoters and corresponding regulation elements. As these expression vectors or cassettes are typically limited to particular cell systems, these expression systems have to be adapted for use in different cell systems. Such adapted expression vectors or cassettes are then usually transfected into the cells and typically treated in dependence of the specific cell line. Therefore, preference is given primarily to those nucleic acid molecules which are able to express the encoded proteins in a target cell by systems inherent in the cell, independent of promoters and regulation elements which are specific for particular cell types. In this context, there can be distinguished between mRNA stabilizing elements and elements which increase translation efficiency of the mRNA.

mRNAs which are optimized in their coding sequence and which are in general suitable for such a purpose are described in application WO 02/098443 (CureVac GmbH). For example, WO 02/098443 describes mRNAs that are stabilised in general form and optimised for translation in their coding regions. WO 02/098443 further discloses a method for determining sequence modifications. WO 02/098443 additionally describes possibilities for substituting adenine and uracil nucleotides in mRNA sequences in order to increase the guanine/cytosine (G/C) content of the sequences. According to WO 02/098443, such substitutions and adaptations for increasing the G/C content can be used for gene therapeutic applications but also genetic vaccines in the treatment of cancer or infectious diseases. In this context, WO 02/098443 generally mentions sequences as a base sequence for such modifications, in which the modified mRNA codes for at least one biologically active peptide or polypeptide, which is translated in the patient to be treated, for example, either not at all or inadequately or with faults. Alternatively, WO 02/098443 proposes mRNAs coding for antigens e.g. therapeutic proteins or viral antigens as a base sequence for such modifications.

In a further approach to increase the expression of an encoded protein the application WO 2007/036366 describes the positive effect of long poly(A) sequences (particularly longer than 120 bp) and the combination of at least two 3' untranslated regions of the beta globin gene on mRNA stability and translational activity.

However, even though all these latter prior art documents already try to provide quite efficient tools for gene therapy approaches and additionally improved mRNA stability and translational activity, there still remains the problem of a generally lower stability of RNA-based applications versus DNA vaccines and DNA based gene therapeutic approaches. Accordingly, there still exists a need in the art to provide improved tools for gene therapy approaches or as a supplementary therapy for conventional treatments as discussed above, which allow for better provision of encoded proteins in vivo, e.g. via a further improved mRNA stability and/or translational activity, preferably for gene therapy.

Furthermore despite of all progress in the art, efficient expression of an encoded peptide or protein in cell-free systems, cells or organisms (recombinant expression) is still a challenging problem.

The object underlying the present invention is, therefore, to provide additional and/or alternative methods to increase expression of an encoded protein, preferably via further stabilization of the mRNA and/or an increase of the translational efficiency of such an mRNA with respect to such nucleic acids known from the prior art for the use in gene therapy in the therapeutic or prophylactic treatment of inherited or acquired diseases, particularly as defined herein.

This object is solved by the subject matter of the attached claims. Particularly, the object underlying the present invention is solved according to a first aspect by an inventive nucleic acid sequence comprising or coding for
  a) a coding region, encoding at least one peptide or protein which comprises a therapeutic protein or a fragment, variant or derivative thereof;
  b) at least one histone stem-loop, and
  c) a poly(A) sequence or a polyadenylation signal,
preferably for increasing the expression of said encoded peptide or protein.

Alternatively, any appropriate stem loop sequence other than a histone stem loop sequence (derived from histone genes, in particular histone genes of the families H1, H2A, H2B, H3 and H4) may be employed by the present invention in all of its aspects and embodiments.

In this context it is particularly preferred that the inventive nucleic acid according to the first aspect of the present invention is produced at least partially by DNA or RNA synthesis, preferably as described herein or is an isolated nucleic acid.

The present invention is based on the surprising finding of the present inventors, that the combination of a poly(A) sequence or polyadenylation signal and at least one histone stem-loop, even though both representing alternative mechanisms in nature, acts synergistically as this combination increases the protein expression manifold above the level observed with either of the individual elements. The synergistic effect of the combination of poly(A) and at least one histone stem-loop is seen irrespective of the order of poly(A) and histone stem-loop and irrespective of the length of the poly(A) sequence.

Therefore it is particularly preferred that the inventive nucleic acid sequence comprises or codes for a) a coding region, encoding at least one peptide or protein which comprises a therapeutic protein or a fragment, variant or derivative thereof; b) at least one histone stem-loop, and c) a poly(A) sequence or polyadenylation sequence; preferably for increasing the expression level of said encoded peptide or protein, wherein the encoded protein is preferably no histone protein, in particular no histone protein of the H4, H3, H2A and/or H2B histone family or a fragment, derivative or variant thereof retaining histone(-like) function), namely forming a nucleosome.

Also, the encoded protein typically does not correspond to a histone linker protein of the H1 histone family. The inventive nucleic acid molecule does typically not contain any regulatory signals (5' and/or, particularly, 3') of a mouse histone gene, in particular not of a mouse histone gene H2A and, further, most preferably not of the mouse histone gene H2A614. In particular, it does not contain a histone stem loop and/or a histone stem loop processing signal from a mouse histone gene, in particular not of mouse histone gene H2A und, most preferably not of mouse histone gene H2A614.

Also, the inventive nucleic acid typically does not provide a reporter protein (e.g. Luciferase, GFP, EGFP, β-Galactosidase, particularly EGFP), galactokinase (galK) and/or marker or selection protein (e.g. alpha-Globin, Galactokinase and Xanthine:Guanine phosphoribosyl transferase (GPT)) or a bacterial reporter protein, e.g. chloramphenicol acetyl transferase (CAT) or other bacterial antibiotics resistance proteins, e.g. derived from the bacterial neo gene in its element (a).

A reporter, marker or selection protein is typically understood not to be a therapeutic protein according to the invention. A reporter, marker or selection protein or its underlying gene is commonly used as a research tool in bacteria, cell culture, animals or plants. They confer on organisms (preferably heterologously) expressing them an easily identifiable property, which may be measured or which allows for selection. Specifically, marker or selection proteins exhibit a selectable function. Typically, such selection, marker or reporter proteins do not naturally occur in humans or other mammals, but are derived from other organisms, in particular from bacteria or plants. Accordingly, proteins with selection, marker or reporter function originating from species other than mammals, in particular other than humans, are preferably excluded from being understood as "therapeutic protein" according to the present invention. In particular, a selection, marker or reporter protein allows to identify transformed cells by in vitro assays based e.g. on fluorescence or other spectroscopic techniques and resistance towards antibiotics. Selection, reporter or marker genes awarding such properties to transformed cells are therefore typically not understood to be a therapeutic protein according to the invention.

In any case, reporter, marker or selection proteins do usually not exert any therapeutic effect. If any single reporter, marker or selection protein should nevertheless do so (in addition to its reporter, selection or marker function), such a reporter, marker or selection protein is preferably not understood to be a "therapeutic protein" within the meaning of the present invention.

In contrast, a therapeutic protein (including its fragments, variants and derivatives), in particular excluding histone genes of the families H1, H2A, H2B, H3 and H4, according to the present invention does typically not exhibit a selection, marker or reporter function. If any single "therapeutic protein" nevertheless should do so (in addition to its therapeutic function), such a therapeutic protein is preferably not understood to be a "selection, marker or reporter protein" within the meaning of the present invention.

It is most preferably understood that a therapeutic protein according to the invention is derived from mammals, in particular humans, and does not qualify as selection, marker or reporter protein.

Accordingly, it is preferred that the coding region (a) encoding at least one peptide or protein is heterologous to at least (b) the at least one histone stem loop, or more broadly, to any appropriate stem loop. In other words, "heterologous" in the context of the present invention means that the at least one stem loop sequence does not naturally occur as a (regulatory) sequence (e.g. at the 3'UTR) of the specific gene, which encodes the (therapeutic) protein or peptide of element (a) of the inventive nucleic acid. Accordingly, the (histone) stem loop of the inventive nucleic acid is derived preferably from the 3' UTR of a gene other than the one comprising the coding region of element (a) of the inventive nucleic acid. E.g., the coding region of element (a) will not encode a histone protein or a fragment, variant or derivative thereof (retaining the function of a histone protein), if the inventive nucleic is heterologous, but will encode any other peptide or sequence (of the same or another species) which exerts a biological function, preferably therapeutic function other than a histone(-like) function, e.g. will encode an therapeutic protein (exerting a therapeutic function, e.g. in terms endocrine disorders, replacing defective endogenous, e.g. mammalian, in particular human proteins).

In this context it is particularly preferred that the inventive nucleic acid comprises or codes for in 5'- to 3'-direction:
a) a coding region, encoding at least one peptide or protein which comprises a therapeutic protein or a fragment, variant or derivative thereof;
b) at least one histone stem-loop, optionally without a histone downstream element (HDE) 3' to the histone stem-loop
c) a poly(A) sequence or a polyadenylation signal.

The term "histone downstream element (HDE) refers to a purine-rich polynucleotide stretch of about 15 to 20 nucleotides 3' of naturally occurring histone stem-loops, which represents the binding site for the U7 snRNA involved in processing of histone pre-mRNA into mature histone mRNA. For example in sea urchins the HDE is CAAGAAAGA (Dominski, Z. and W. F. Marzluff (2007), Gene 396(2): 373-90).

Furthermore it is preferable that the inventive nucleic acid according to the first aspect of the present invention does not comprise an intron.

In another particular preferred embodiment, the inventive nucleic acid sequence according to the first aspect of the present invention comprises or codes for from 5' to 3':
a) a coding region, preferably encoding at least one peptide or protein which comprises a therapeutic protein or a fragment, variant or derivative thereof;
c) a poly(A) sequence; and
b) at least one histone stem-loop.

The inventive nucleic acid sequence according to the first embodiment of the present invention comprise any suitable nucleic acid, selected e.g. from any (single-stranded or double-stranded) DNA, preferably, without being limited thereto, e.g. genomic DNA, plasmid DNA, single-stranded DNA molecules, double-stranded DNA molecules, or may be selected e.g. from any PNA (peptide nucleic acid) or may be selected e.g. from any (single-stranded or double-stranded) RNA, preferably a messenger RNA (mRNA); etc. The inventive nucleic acid sequence may also comprise a viral RNA (vRNA). However, the inventive nucleic acid sequence may not be a viral RNA or may not contain a viral RNA. More specifically, the inventive nucleic acid sequence may not contain viral sequence elements, e.g. viral enhancers or viral promotors (e.g. no inactivated viral promoter or sequence elements, more specifically not inactivated by replacement strategies), or other viral sequence elements, or viral or retroviral nucleic acid sequences. More specifically, the inventive nucleic acid sequence may not be a retroviral or viral vector or a modified retroviral or viral vector.

In any case, the inventive nucleic acid sequence may or may not contain an enhancer and/or promoter sequence, which may be modified or not or which may be activated or not. The enhancer and or promoter may be plant expressible or not expressible, and/or in eukaryotes expressible or not expressible and/or in prokaryotes expressible or not expressible. The inventive nucleic acid sequence may contain a sequence encoding a (self-splicing) ribozyme or not.

In specific embodiments the inventive nucleic acid sequence may be or may comprise a self-replicating RNA (replicon).

Preferably, the inventive nucleic acid sequence is a plasmid DNA, or an RNA, particularly an mRNA.

In particular embodiments of the first aspect of the present invention, the inventive nucleic acid is a nucleic acid sequence comprised in a nucleic acid suitable for in vitro transcription, particularly in an appropriate in vitro transcription vector (e.g. a plasmid or a linear nucleic acid sequence comprising specific promoters for in vitro transcription such as T3, T7 or Sp6 promoters).

In further particular preferred embodiments of the first aspect of the present invention, the inventive nucleic acid is comprised in a nucleic acid suitable for transcription and/or translation in an expression system (e.g. in an expression vector or plasmid), particularly a prokaryotic (e.g. bacteria like *E. coli*) or eukaryotic (e.g. mammalian cells like CHO cells, yeast cells or insect cells or whole organisms like plants or animals) expression system.

The term "expression system" means a system (cell culture or whole organisms) which is suitable for production of peptides, proteins or RNA particularly mRNA (recombinant expression).

The inventive nucleic acid sequence according to the first aspect of the present invention comprises or codes for at least one (histone) stem-loop. A stem-loop, in general (irrespective of whether it is a histone stem loop or not), can occur in single-stranded DNA or, more commonly, in RNA. The structure is also known as a hairpin or hairpin loop and usually consists of a stem and a (terminal) loop within a consecutive sequence, wherein the stem is formed by two neighbored entirely or partially reverse complementary sequences separated by a short sequence as sort of spacer, which builds the loop of the stem-loop structure. The two neighbored entirely or partially reverse complementary sequences may be defined as e.g. stem loop elements stem1 and stem2. The stem loop is formed when these two neighbored entirely or partially reverse complementary sequences, e.g. stem loop elements stem1 and stem2, form base-pairs with each other, leading to a double stranded nucleic acid sequence stretch comprising an unpaired loop at its terminal ending formed by the short sequence located between stem loop elements stem1 and stem2 on the consecutive sequence. The unpaired loop thereby typically represents a region of the nucleic acid which is not capable of base pairing with either of these stem loop elements. The resulting lollipop-shaped structure is a key building block of many RNA secondary structures. The formation of a stem-loop structure is thus dependent on the stability of the resulting stem and loop regions, wherein the first prerequisite is typically the presence of a sequence that can fold back on itself to form a paired double strand. The stability of paired stem loop elements is determined by the length, the number of mismatches or bulges it contains (a small number of mismatches is typically tolerable, especially for a longer double stranded stretch), and the base composition of the paired region. In the context of the present invention, a loop length of 3 to 15 bases is conceivable, while a more preferred loop length is 3-10 bases, more preferably 3 to 8, 3 to 7, 3 to 6 or even more preferably 4 to 5 bases, and most preferably 4 bases. The stem sequence forming the double stranded structure typically has a length of between 5 to 10 bases, more preferably, between 5 to 8 bases.

In the context of the present invention, a histone stem-loop is typically derived from histone genes (e.g. genes from the histone families H1, H2A, H2B, H3, H4) and comprises an intramolecular base pairing of two neighbored entirely or partially reverse complementary sequences, thereby forming a stem-loop. Typically, a histone 3' UTR stem-loop is an RNA element involved in nucleocytoplasmic transport of the histone mRNAs, and in the regulation of stability and of translation efficiency in the cytoplasm. The mRNAs of metazoan histone genes lack polyadenylation and a poly-A tail, instead 3' end processing occurs at a site between this highly conserved stem-loop and a purine rich region around 20 nucleotides downstream (the histone downstream element, or HDE). The histone stem-loop is bound by a 31 kDa stem-loop binding protein (SLBP—also termed the histone hairpin binding protein, or HBP). Such histone stem-loop structures are preferably employed by the present invention in combination with other sequence elements and structures, which do not occur naturally (which means in untransformed living organisms/cells) in histone genes, but are combined—according to the invention—to provide an artificial, heterologous nucleic acid. Accordingly, the present invention is particularly based on the finding that an artificial (non-native) combination of a histone stem-loop structure with other heterologous sequence elements, which do not occur in histone genes or metazoan histone genes and are isolated from operational and/or regulatory sequence regions (influencing transcription and/or translation) of genes coding for proteins other than histones, provide advantageous effects. Accordingly, one aspect of the invention provides the combination of a histone stem-loop structure with a poly(A) sequence or a sequence representing a polyadenylation signal (3'-terminal of a coding region), which does not occur in metazoan histone genes.

According to another preferred aspect of the invention, a combination of a histone stem-loop structure with a coding region coding for a therapeutic protein, which does, preferably not occur in metazoan histone genes, is provided herewith (coding region and histone stem loop sequence are heterologous). It is preferred, if such therapeutic proteins occur naturally in mammalians, preferably humans. In a still further preferred embodiment, all the elements (a), (b) and (c) of the inventive nucleic acid are heterologous to each other and are combined artificially from three different sources, e.g. (a) the therapeutic protein coding region from a human gene, (b) the histone stem loop from an untranlated region of a metazoan, e.g. mammalian, non-human or human, histone gene and (c) the poly(A) sequence or the polyadenylation signal from e.g. an untranlated region of a gene other than a histone gene and other than the gene coding for the therapeutic protein according to element (a) of such an inventive nucleic acid.

A histone stem loop is, therefore, a stem-loop structure as described herein, which, if preferably functionally defined, exhibits/retains the property of binding to its natural binding partner, the stem-loop binding protein (SLBP—also termed the histone hairpin binding protein, or HBP).

According to the present invention the histone stem loop sequence according to component (b) of claim 1 may not derived from a mouse histone protein. More specifically, the histone stem loop sequence may not be derived from mouse histone gene H2A614. Also, the nucleic acid of the invention may neither contain a mouse histone stem loop sequence nor contain mouse histone gene H2A614. Further, the inventive nucleic acid sequence may not contain a stem-loop processing signal, more specifically, a mouse histone processing signal and, most specifically, may not contain mouse stem loop processing signal H2kA614, even if the inventive nucleic acid sequence may contain at least one mammalian histone gene. However, the at least one mammalian histone gene may not be Seq. ID No. 7 of WO 01/12824.

According to one preferred embodiment of the first inventive aspect, the inventive nucleic acid sequence comprises or codes for at least one histone stem-loop sequence, preferably according to at least one of the following formulae (I) or (II):

formula (I) (stem-loop sequence without stem bordening elements):

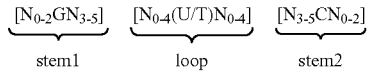

stem1   loop   stem2 formula (II) (stem-loop sequence without stem bordening elements):

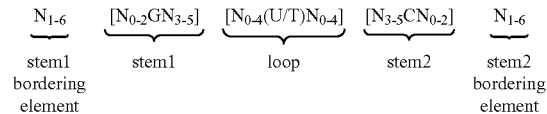

$N_{1-6}$     $[N_{0-2}GN_{3-5}]$   $[N_{0-4}(U/T)N_{0-4}]$   $[N_{3-5}CN_{0-2}]$   $N_{1-6}$ stem1       stem1        loop        stem2      stem2
bordering                                       bordering
element                                         element wherein:
stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;
  wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;
  wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and
  wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;
  wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and
  wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;
  wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;
  wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and
  wherein C is cytidine or an analogue thereof, and may be optionally replaced by a guanosine or an analogue thereof provided that its complementary nucleotide guanosine in stem1 is replaced by cytidine;

wherein
stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one or more bases in one stem do not have a complementary base in the reverse complementary sequence of the other stem.

In the above context, a wobble base pairing is typically a non-Watson-Crick base pairing between two nucleotides. The four main wobble base pairs in the present context, which may be used, are guanosine-uridine, inosine-uridine, inosine-adenosine, inosine-cytidine (G-U/T, I-U/T, I-A and I-C) and adenosine-cytidine (A-C).

Accordingly, in the context of the present invention, a wobble base is a base, which forms a wobble base pair with a further base as described above. Therefore non-Watson-Crick base pairing, e.g. wobble base pairing, may occur in the stem of the histone stem-loop structure according to the present invention.

In the above context a partially reverse complementary sequence comprises maximally 2, preferably only one mismatch in the stem-structure of the stem-loop sequence formed by base pairing of stem1 and stem2. In other words, stem1 and stem2 are preferably capable of (full) base pairing with each other throughout the entire sequence of stem1 and stem2 (100% of possible correct Watson-Crick or non-Watson-Crick base pairings), thereby forming a reverse complementary sequence, wherein each base has its correct Watson-Crick or non-Watson-Crick base pendant as a complementary binding partner. Alternatively, stem1 and stem2 are preferably capable of partial base pairing with each other throughout the entire sequence of stem1 and stem2, wherein at least about 70%, 75%, 80%, 85%, 90%, or 95% of the 100% possible correct Watson-Crick or non-Watson-Crick base pairings are occupied with the correct Watson-Crick or non-Watson-Crick base pairings and at most about 30%, 25%, 20%, 15%, 10%, or 5% of the remaining bases are unpaired.

According to a preferred embodiment of the first inventive aspect, the at least one histone stem-loop sequence (with stem bordering elements) of the inventive nucleic acid sequence as defined herein comprises a length of about 15 to about 45 nucleotides, preferably a length of about 15 to about 40 nucleotides, preferably a length of about 15 to about 35 nucleotides, preferably a length of about 15 to about 30 nucleotides and even more preferably a length of about 20 to about 30 and most preferably a length of about 24 to about 28 nucleotides.

According to a further preferred embodiment of the first inventive aspect, the at least one histone stem-loop sequence (without stem bordering elements) of the inventive nucleic acid sequence as defined herein comprises a length of about 10 to about 30 nucleotides, preferably a length of about 10 to about 20 nucleotides, preferably a length of about 12 to about 20 nucleotides, preferably a length of about 14 to about 20 nucleotides and even more preferably a length of about 16 to about 17 and most preferably a length of about 16 nucleotides.

According to a further preferred embodiment of the first inventive aspect, the inventive nucleic acid sequence according to the first aspect of the present invention may comprise or code for at least one histone stem-loop sequence according to at least one of the following specific formulae (Ia) or (IIa):

formula (Ia) (stem-loop sequence without stem bordening elements):

$$\underbrace{[N_{0-1}GN_{3-5}]}_{\text{stem1}} \underbrace{[N_{1-3}(U/T)N_{0-2}]}_{\text{loop}} \underbrace{[N_{3-5}CN_{0-1}]}_{\text{stem2}}$$

formula (IIa) (stem-loop sequence without stem bordening elements):

$$\underbrace{N_{2-5}}_{\substack{\text{stem1}\\\text{bordering}\\\text{element}}} \underbrace{[N_{0-1}GN_{3-5}]}_{\text{stem1}} \underbrace{[N_{1-3}(U/T)N_{0-2}]}_{\text{loop}} \underbrace{[N_{3-5}CN_{0-1}]}_{\text{stem2}} \underbrace{N_{2-5}}_{\substack{\text{stem2}\\\text{bordering}\\\text{element}}}$$

wherein:
N, C, G, T and U are as defined above.

According to a further more particularly preferred embodiment of the first aspect, the inventive nucleic acid sequence may comprise or code for at least one histone stem-loop sequence according to at least one of the following specific formulae (Ib) or (IIb):

formula (Ib) (stem-loop sequence without stem bordening elements):

$$\underbrace{[N_1GN_4]}_{\text{stem1}} \underbrace{[N_2(U/T)N_1]}_{\text{loop}} \underbrace{[N_4CN_1]}_{\text{stem2}}$$

formula (IIb) (stem-loop sequence without stem bordening elements):

$$\underbrace{N_{4-5}}_{\substack{\text{stem1}\\\text{bordering}\\\text{element}}} \underbrace{[N_1GN_4]}_{\text{stem1}} \underbrace{[N_2(U/T)N_1]}_{\text{loop}} \underbrace{[N_4CN_1]}_{\text{stem2}} \underbrace{N_{4-5}}_{\substack{\text{stem2}\\\text{bordering}\\\text{element}}}$$

wherein:
N, C, G, T and U are as defined above.

According to an even more preferred embodiment of the first inventive aspect, the inventive nucleic acid sequence according to the first aspect of the present invention may comprise or code for at least one histone stem-loop sequence according to at least one of the following specific formulae (Ic) to (Ih) or (IIc) to (IIh), shown alternatively in its stem-loop structure and as a linear sequence representing histone stem-loop sequences as generated according to Example 1:

formula (Ic): (metazoan and protozoan histone stem-loop consensus sequence without stem bordering elements):

```
                                        (SEQ ID NO: 1)
    N U
   N   N
   N-N
   N-N
   N-N
   N-N
   G-C
   N-N   (stem-loop structure)

NGNNNNNNUNNNNNCN
(linear sequence)
``` formula (IIc): (metazoan and protozoan histone stem-loop consensus sequence with stem bordering elements):

```
                                        (SEQ ID NO: 2)
    N U
   N   N
   N-N
   N-N
   N-N
   N-N
   G-C
N*N*NNNN-NNNN*N*N*   (stem-loop structure)

N*N*NNNNGNNNNNNUNNNNNNCNNNN*N*N*
(linear sequence)
``` formula (Id): (without stem bordering elements)

```
                                        (SEQ ID NO: 3)
    N U
   N   N
   N-N
   N-N
   N-N
   N-N
   C-G
   N-N   (stem-loop structure)

NCNNNNNNUNNNNNGN
(linear sequence)
``` formula (IId): (with stem bordering elements)

```
                                        (SEQ ID NO: 4)
    N U
   N   N
   N-N
   N-N
   N-N
   N-N
   C-G
N*N*NNNN-NNNN*N*N*   (stem-loop structure)

N*N*NNNNCNNNNNNUNNNNNGNNNN*N*N*
(linear sequence)
``` formula (Ie): (protozoan histone stem-loop consensus sequence without stem bordering elements)

```
                                        (SEQ ID NO: 5)
    N U
   N   N
   N-N
   N-N
   N-N
   N-N
   G-C
   D-H   (stem-loop structure)

DGNNNNNNUNNNNNCH
(linear sequence)
``` formula (IIe): (protozoan histone stem-loop consensus sequence with stem bordering elements)

```
                                        (SEQ ID NO: 6)
    N U
   N   N
   N-N
   N-N
   N-N
   N-N
   G-C
N*N*NNND-HNNN*N*N*   (stem-loop structure)

N*N*NNNDGNNNNNNUNNNNNCHNNN*N*N*
(linear sequence)
``` formula (If): (metazoan histone stem-loop consensus sequence without stem bordering elements)

(SEQ ID NO: 7)
```
    N U
   N   N
   Y-V
   Y-N
   B-D
   N-N
   G-C
   N-N  (stem-loop structure)
```

NGNBYYNNUNVNDNCN
(linear sequence)

formula (IIf): (metazoan histone stem-loop consensus sequence with stem bordering elements)

(SEQ ID NO: 8)
```
    N U
   N   N
   Y-V
   Y-N
   B-D
   N-N
   G-C
N*N*NNNN-NNNN*N*N*  (stem-loop structure)
```

N*N*NNNNGNBYYNNUNVNDNCNNNN*N*N*
(linear sequence)

formula (Ig): (vertebrate histone stem-loop consensus sequence without stem bordering elements)

(SEQ ID NO: 9)
```
    N U
   D   H
   Y-A
   Y-B
   Y-R
   H-D
   G-C
   N-N  (stem-loop structure)
```

NGHYYYDNUHABRDCN
(linear sequence)

formula (IIg): (vertebrate histone stem-loop consensus sequence with stem bordering elements)

(SEQ ID NO: 10)
```
    N U
   D   H
   Y-A
   Y-B
   Y-R
   H-D
   G-C
N*N*HNNN-NNNN*N*H*  (stem-loop structure)
```

N*N*HNNNGHYYYDNUHABRDCNNNN*N*H*
(linear sequence)

formula (Ih): (human histone stem-loop consensus sequence (*Homo sapiens*) without stem bordering elements)

(SEQ ID NO: 11)
```
    Y U
   D   H
   U-A
   C-S
   Y-R
   H-R
   G-C
   D-C  (stem-loop structure)
```

DGHYCUDYUHASRRCC
(linear sequence)

formula (IIh): (human histone stem-loop consensus sequence (*Homo sapiens*) with stem bordering elements)

(SEQ ID NO: 12)
```
    Y U
   D   H
   U-A
   C-S
   Y-R
   H-R
   G-C
N*H*AAHD-CVHB*N*H*  (stem loop structure)
```

N*H*AAHDGHYCUDYUHASRRCCVHB*N*H*
(linear sequence)

wherein in each of above formulae (Ic) to (Ih) or (IIc) to (IIh):
N, C, G, A, T and U are as defined above;
each U may be replaced by T;
each (highly) conserved G or C in the stem elements 1 and 2 may be replaced by its complementary nucleotide base C or G, provided that its complementary nucleotide in the corresponding stem is replaced by its complementary nucleotide in parallel; and/or
G, A, T, U, C, R, Y, M, K, S, W, H, B, V, D, and N are nucleotide bases as defined in the following Table:

| abbreviation | Nucleotide bases | remark |
| --- | --- | --- |
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | Present or not | Base may be present or not |

In this context it is particularly preferred that the histone stem-loop sequence according to at least one of the formulae (I) or (Ia) to (Ih) or (II) or (IIa) to (IIh) of the present invention is selected from a naturally occurring histone stem loop sequence, more particularly preferred from protozoan or metazoan histone stem-loop sequences, and even more particularly preferred from vertebrate and mostly preferred from mammalian histone stem-loop sequences especially from human histone stem-loop sequences.

According to a particularly preferred embodiment of the first aspect, the histone stem-loop sequence according to at least one of the specific formulae (I) or (Ia) to (Ih) or (II) or (IIa) to (IIh) of the present invention is a histone stem-loop sequence comprising at each nucleotide position the most frequently occurring nucleotide, or either the most frequently or the second-most frequently occurring nucleotide of naturally occurring histone stem-loop sequences in metazoa and protozoa (FIG. 1), protozoa (FIG. 2), metazoa (FIG. 3), vertebrates (FIG. 4) and humans (FIG. 5) as shown in FIG. 1-5. In this context it is particularly preferred that at least 80%, preferably at least 85%, or most preferably at least 90% of all nucleotides correspond to the most frequently occurring nucleotide of naturally occurring histone stem-loop sequences.

In a further particular embodiment of the first aspect, the histone stem-loop sequence according to at least one of the specific formulae (I) or (Ia) to (Ih) of the present invention is selected from following histone stem-loop sequences (without stem-bordering elements) representing histone stem-loop sequences as generated according to Example 1:

```
(SEQ ID NO: 13 according to formula (Ic))
    VGYYYYHHTHRVVRCB (SEQ ID NO: 14 according to formula (Ic))
    SGYYYTTYTMARRRCS (SEQ ID NO: 15 according to formula (Ic))
    SGYYCTTTTMAGRRCS (SEQ ID NO: 16 according to formula (Ie))
    DGNNNBNNTHVNNNCH (SEQ ID NO: 17 according to formula (Ie))
    RGNNNYHBTHRDNNCY (SEQ ID NO: 18 according to formula (Ie))
    RGNDBYHYTHRDHNCY (SEQ ID NO: 19 according to formula (If))
    VGYYYTYHTHRVRRCB (SEQ ID NO: 20 according to formula (If))
    SGYYCTTYTMAGRRCS (SEQ ID NO: 21 according to formula (If))
    SGYYCTTTTMAGRRCS (SEQ ID NO: 22 according to formula (Ig))
    GGYYCTTYTHAGRRCC (SEQ ID NO: 23 according to formula (Ig))
    GGCYCTTYTMAGRGCC (SEQ ID NO: 24 according to formula (Ig))
    GGCTCTTTTMAGRGCC (SEQ ID NO: 25 according to formula (Ih))
    DGHYCTDYTHASRRCC (SEQ ID NO: 26 according to formula (Ih))
    GGCYCTTTTHAGRGCC (SEQ ID NO: 27 according to formula (Ih))
    GGCYCTTTTMAGRGCC
```

Furthermore in this context following histone stem-loop sequences (with stem bordering elements) as generated according to Example 1 according to one of specific formulae (II) or (IIa) to (IIh) are particularly preferred:

```
(SEQ ID NO: 28 according to formula (IIc))
    H*H*HHVVGYYYYHHTHRVVRCBVHH*N*N*

(SEQ ID NO: 29 according to formula (IIc))
    M*H*MHMSGYYYTTYTMARRRCSMCH*H*H*

(SEQ ID NO: 30 according to formula (IIc))
    M*M*MMMSGYYCTTTTMAGRRCSACH*M*H*

(SEQ ID NO: 31 according to formula (IIe))
    N*N*NNNDGNNNBNNTHVNNNCHNHN*N*N*

(SEQ ID NO: 32 according to formula (IIe))
    N*N*HHNRGNNNYHBTHRDNNCYDHH*N*N*

(SEQ ID NO: 33 according to formula (IIe))
    N*H*HHVRGNDBYHYTHRDHNCYRHH*H*H*

(SEQ ID NO: 34 according to formula (IIf))
    H*H*MHMVGYYYTYHTHRVRRCBVMH*H*N*

(SEQ ID NO: 35 according to formula (IIf))
    M*M*MMMSGYYCTTYTMAGRRCSMCH*H*H*

(SEQ ID NO: 36 according to formula (IIf))
    M*M*MMMSGYYCTTTTMAGRRCSACH*M*H*

(SEQ ID NO: 37 according to formula (IIg))
    H*H*MAMGGYYCTTYTHAGRRCCVHN*N*M*

(SEQ ID NO: 38 according to formula (IIg))
    H*H*AAMGGCYCTTYTMAGRGCCVCH*H*M*

(SEQ ID NO: 39 according to formula (IIg))
    M*M*AAMGGCTCTTTTMAGRGCCMCY*M*M*

(SEQ ID NO: 40 according to formula (IIh))
    N*H*AAHDGHYCTDYTHASRRCCVHB*N*H*

(SEQ ID NO: 41 according to formula (IIh))
    H*H*AAMGGCYCTTTTHAGRGCCVMY*N*M*

(SEQ ID NO: 42 according to formula (IIh))
    H*M*AAAGGCYCTTTTMAGRGCCRMY*H*M*
```

According to a further preferred embodiment of the first inventive aspect, the inventive nucleic acid sequence comprises or codes for at least one histone stem-loop sequence showing at least about 80%, preferably at least about 85%, more preferably at least about 90%, or even more preferably at least about 95%, sequence identity with the not to 100% conserved nucleotides in the histone stem-loop sequences according to at least one of specific formulae (I) or (Ia) to (Ih) or (II) or (IIa) to (IIh) or with a naturally occurring histone stem-loop sequence.

In a preferred embodiment, the histone stem loop sequence does not contain the loop sequence 5'-UUUC-3'. More specifically, the histone stem loop does not contain the stem1 sequence 5'-GGCUCU-3' and/or the stem2 sequence 5'-AGAGCC-3', respectively. In another preferred embodiment, the stem loop sequence does not contain the loop sequence 5'-CCUGCCC-3' or the loop sequence 5'-UGAAU-3'. More specifically, the stem loop does not contain the stem1 sequence 5'-CCUGAGC-3' or does not contain the steml sequence 5'-ACCUUUCUCCA-3' (SEQ ID NO: 59) and/or the stem2 sequence 5'-GCUCAGG-3' or 5'-UGGAGAAAGGU-3' (SEQ ID NO: 60), respectively. Also, as far as the invention is not limited to histone stem loop sequences specifically, stem loop sequences are preferably not derived from a mammalian insulin receptor 3'-untranslated region. Also, preferably, the inventive nucleic acid may not contain histone stem loop processing signals, in particular not those derived from mouse histone gene H2A614 gene (H2kA614).

The inventive nucleic acid sequence according to the first aspect of the present invention may optionally comprise or code for a poly(A) sequence. When present, such a poly(A) sequence comprises a sequence of about 25 to about 400 adenosine nucleotides, preferably a sequence of about 30 or, more preferably, of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context the term "about" refers to a deviation of ±10% of the value(s) it is attached to. Accordingly, the poly(A) sequence contains at least 25 or more than 25, more preferably, at least 30, more preferably at least 50 adenosine nucleotides. Therefore, such a poly (A) sequence does typically not contain less than 20 adenosine nucleotides. More particularly, it does not contain 10 and/or less than 10 adenosine nucleotides.

Preferably, the nucleic acid according of the present invention does not contain one or two or at least one or all but one or all of the components of the group consisting of: a sequence encoding a ribozyme (preferably a self-splicing ribozyme), a viral nucleic acid sequence, a histone stem-loop processing signal, in particular a histone-stem loop processing sequence derived from mouse histone H2A614 gene, a Neo gene, an inactivated promoter sequence and an inactivated enhancer sequence. Even more preferably, the nucleic acid according to the invention does not contain a ribozyme, preferably a self-splicing ribozyme, and one of the group consisting of: a Neo gene, an inactivated promoter sequence, an inactivated enhancer sequence, a histone stem-loop processing signal, in particular a histone-stem loop processing sequence derived from mouse histone H2A614 gene. Accordingly, the nucleic acid may in a preferred mode neither contain a ribozyme, preferably a self-splicing ribozyme, nor a Neo gene or, alternatively, neither a ribozyme, preferably a self-splicing ribozyme, nor any resistance gene (e.g. usually applied for selection). In another preferred mode, the nucleic acid of the invention may neither contain a ribozyme, preferably a self-splicing ribozyme nor a histone stem-loop processing signal, in particular a histone-stem loop processing sequence derived from mouse histone H2A614 gene Alternatively, according to the first aspect of the present invention, the inventive nucleic sequence optionally comprises a polyadenylation signal which is defined herein as a signal which conveys polyadenylation to a (transcribed) mRNA by specific protein factors (e.g. cleavage and polyadenylation specificity factor (CPSF), cleavage stimulation factor (CstF), cleavage factors I and II (CF I and CF II), poly(A) polymerase (PAP)). In this context a consensus polyadenylation signal is preferred comprising the NN(U/T)ANA consensus sequence. In a particular preferred aspect the polyadenylation signal comprises one of the following sequences: AA(U/T)AAA or A(U/T)(U/T)AAA (wherein uridine is usually present in RNA and thymidine is usually present in DNA). In some embodiments, the polyadenylation signal used in the inventive nucleic acid does not correspond to the U3 snRNA, U5, the polyadenylation processing signal from human gene G-CSF, or the SV40 polyadenylation signal sequences. In particular, the above polyadenylation signals are not combined with any antibiotics resistance gene (or any other reporter, marker or selection gene), in particular not with the resistance neo gene (neomycin phosphotransferase) (as the gene of the coding region according to element (a) of the inventive nucleic acid. And, any of the above polyadenylation signals (which typically do not occur in the inventive nucleic acid) are preferably not combined with the histone stem loop or the histone stem loop processing signal from mouse histone gene H2A614 in an inventive nucleic acid.

The inventive nucleic acid sequence according to the first aspect of the present invention furthermore encodes a protein or a peptide, which comprises a therapeutic protein or a fragment, variant or derivative thereof.

Therapeutic proteins as defined herein are peptides or proteins which are beneficial for the treatment of any inherited or acquired disease or which improves the condition of an individual. Particularly, therapeutic proteins plays a big role in the creation of therapeutic agents that could modify and repair genetic errors, destroy cancer cells or pathogen infected cells, treat immune system disorders, treat metabolic or endocrine disorders, among other functions. For instance, Erythropoietin (EPO), a protein hormone can be utilized in treating patients with erythrocyte deficiency, which is a common cause of kidney complications. Furthermore adjuvant proteins, therapeutic antibodies are encompassed by therapeutic proteins and also hormone replacement therapy which is e.g. used in the therapy of women in the menopause. In newer approaches somatic cells of a patient are used to reprogram them into pluripotent stem cells which replace the disputed stem cell therapy. Also these proteins used for reprogramming of somatic cells or used for differentiating of stem cells are defined herein as therapeutic proteins. Furthermore therapeutic proteins may be used for other purposes e.g. wound healing, tissue regeneration, angiogenesis, etc.

Therefore therapeutic proteins can be used for various purposes including treatment of various diseases like e.g. infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired.

In this context, particularly preferred therapeutic proteins which can be used inter alia in the treatment of metabolic or endocrine disorders are selected from: Acid sphingomyelinase (Niemann-Pick disease), Adipotide (obesity), Agalsidase-beta (human galactosidase A) (Fabry disease; prevents accumulation of lipids that could lead to renal and cardiovascular complications), Alglucosidase (Pompe disease (glycogen storage disease type II)), alpha-galactosidase A (alpha-GAL A, Agalsidase alpha) (Fabry disease), alpha-glucosidase (Glycogen storage disease (GSD), Morbus Pompe), alpha-L-iduronidase (mucopolysaccharidoses (MPS), Hurler syndrome, Scheie syndrome), alpha-N-acetylglucosaminidase (Sanfilippo syndrome), Amphiregulin (cancer, metabolic disorder), Angiopoietin ((Ang1, Ang2, Ang3, Ang4, ANGPTL2, ANGPTL3, ANGPTL4, ANGPTL5, ANGPTL6, ANGPTL7) (angiogenesis, stabilize vessels), Betacellulin (metabolic disorder), Beta-glucuronidase (Sly syndrome), Bone morphogenetic protein BMPs (BMP1, BMP2, BMP3, BMP4, BMP5, BMP6, BMP7, BMP8a, BMP8b, BMP10, BMP15) (regenerative effect, bone-related conditions, chronic kidney disease (CKD)), CLN6 protein (CLN6 disease—Atypical Late Infantile, Late Onset variant, Early Juvenile, Neuronal Ceroid Lipofuscinoses (NCL)), Epidermal growth factor (EGF) (wound healing, regulation of cell growth, proliferation, and differentiation), Epigen (metabolic disorder), Epiregulin (metabolic disorder), Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23) (wound healing, angiogenesis, endocrine disorders, tissue regeneration), Galsulphase (Mucopolysaccharidosis VI), Ghrelin (irritable bowel syndrome (IBS), obesity, Prader-Willi syndrome, type II diabetes mellitus), Glucocerebrosidase (Gaucher's disease), GM-CSF (regenerative effect, production of white blood cells, cancer), Heparin-binding EGF-like growth factor (HB-EGF) (wound healing, cardiac hypertrophy and heart development and function), Hepatocyte growth factor HGF (regenerative effect, wound healing), Hepcidin (iron metabolism disorders, Beta-thalassemia), Human albumin (Decreased production of albumin (hypoproteinaemia), increased loss of albumin (nephrotic syndrome), hypovolaemia, hyperbilirubinaemia), Idursulphase (Iduronate-2-sulphatase) (Mucopolysaccharidosis II (Hunter syndrome)), Integrins αVβ3, αVβ5 and α5β1 (Bind matrix macromolecules and proteinases, angiogenesis), Iuduronate sulfatase (Hunter syndrome), Laronidase (Hurler and Hurler-Scheie forms of mucopolysaccharidosis I), N-acetylgalactosamine-4-sulfatase (rhASB; galsulfase, Arylsulfatase A (ARSA), Arylsulfatase B (ARSB)) (arylsulfatase B deficiency, Maroteaux-Lamy syndrome, mucopolysaccharidosis VI), N-acetylglucosamine-6-sulfatase (Sanfilippo syndrome), Nerve growth factor (NGF, Brain-Derived Neurotrophic Factor (BDNF), Neurotrophin-3 (NT-3), and Neurotrophin 4/5 (NT-4/5) (regenerative effect, cardiovascular diseases, coronary atherosclerosis, obesity, type 2 diabetes, metabolic syndrome, acute coronary syndromes, dementia, depression, schizophrenia, autism, Rett syndrome, anorexia nervosa, bulimia nervosa, wound healing, skin ulcers, corneal ulcers, Alzheimer's disease), Neuregulin (NRG1, NRG2, NRG3, NRG4) (metabolic disorder, schizophrenia), Neuropilin (NRP-1, NRP-2) (angiogenesis, axon guidance, cell survival, migration), Obestatin (irritable bowel syndrome (IBS), obesity, Prader-Willi syndrome, type II diabetes mellitus), Platelet Derived Growth factor (PDGF (PDFF-A, PDGF-B, PDGF-C, PDGF-D) (regenerative effect, wound healing, disorder in angiogenesis, Arteriosclerosis, Fibrosis, cancer), TGF beta receptors (endoglin, TGF-beta 1 receptor, TGF-beta 2 receptor, TGF-beta 3 receptor) (renal fibrosis, kidney disease, diabetes, ultimately end-stage renal disease (ESRD), angiogenesis), Thrombopoietin (THPO) (Megakaryocyte growth and development factor (MGDF)) (platelets disorders, platelets for donation, recovery of platelet counts after myelosuppressive chemotherapy), Transforming Growth factor (TGF (TGF-a, TGF-beta (TGFbeta1, TGFbeta2, and TGFbeta3))) (regenerative effect, wound healing, immunity, cancer, heart disease, diabetes, Marfan syndrome, Loeys-Dietz syndrome), VEGF (VEGF-A, VEGF-B, VEGF-C, VEGF-D, VEGF-E, VEGF-F and PlGF) (regenerative effect, angiogenesis, wound healing, cancer, permeability), Nesiritide (Acute decompensated congestive heart failure), Trypsin (Decubitus ulcer, varicose ulcer, debridement of eschar, dehiscent wound, sunburn, meconium ileus), adrenocorticotrophic hormone (ACTH) ("Addison's disease, Small cell carcinoma, Adrenoleukodystrophy, Congenital adrenal hyperplasia, Cushing's syndrome, Nelson's syndrome, Infantile spasms), Atrial-natriuretic peptide (ANP) (endocrine disorders), Cholecystokinin (diverse), Gastrin (hypogastrinemia), Leptin (Diabetes, hypertriglyceridemia, obesity), Oxytocin (stimulate breastfeeding, non-progression of parturition), Somatostatin (symptomatic treatment of carcinoid syndrome, acute variceal bleeding, and acromegaly, polycystic diseases of the liver and kidney, acromegaly and symptoms caused by neuroendocrine tumors), Vasopressin (antidiuretic hormone) (diabetes insipidus), Calcitonin (Postmenopausal osteoporosis, Hypercalcaemia, Paget's disease, Bone metastases, Phantom limb pain, Spinal Stenosis), Exenatide (Type 2 diabetes resistant to treatment with metformin and a sulphonylurea), Growth hormone (GH), somatotropin (Growth failure due to GH deficiency or chronic renal insufficiency, Prader-Willi syndrome, Turner syndrome, AIDS wasting or cachexia with antiviral therapy), Insulin (Diabetes mellitus, diabetic ketoacidosis, hyperkalaemia), Insulin-like growth factor 1 IGF-1 (Growth failure in children with GH gene deletion or severe primary IGF1 deficiency, neurodegenerative disease, cardiovascular diseases, heart failure), Mecasermin rinfabate, IGF-1 analog (Growth failure in children with GH gene deletion or severe primary IGF1 deficiency, neurodegenerative disease, cardiovascular diseases, heart failure), Mecasermin, IGF-1 analog (Growth failure in children with GH gene deletion or severe primary IGF1 deficiency, neurodegenerative disease, cardiovascular diseases, heart failure), Pegvisomant (Acromegaly), Pramlintide (Diabetes mellitus, in combination with insulin), Teriparatide (human parathyroid hormone residues 1-34) (Severe osteoporosis), Becaplermin (Debridement adjunct for diabetic ulcers), Dibotermin-alpha (Bone morphogenetic protein 2) (Spinal fusion surgery, bone injury repair), Histrelin acetate (gonadotropin releasing hormone; GnRH) (Precocious puberty), Octreotide (Acromegaly, symptomatic relief of VIP-secreting adenoma and metastatic carcinoid tumours), and Palifermin (keratinocyte growth factor; KGF) (Severe oral mucositis in patients undergoing chemotherapy, wound healing). (in brackets is the particular disease for which the therapeutic protein is used in the treatment). These and other proteins are understood to be therapeutic, as they are meant to treat the subject by replacing its defective endogenous production of a functional protein in sufficient amounts. Accordingly, such therapeutic proteins are typically mammalian, in particular human proteins.

For the treatment of blood disorders, diseases of the circulatory system, diseases of the respiratory system, cancer or tumour diseases, infectious diseases or immunodeficiencies following therapeutic proteins may be used: Alteplase (tissue plasminogen activator; tPA) (Pulmonary embolism, myocardial infarction, acute ischaemic stroke, occlusion of central venous access devices), Anistreplase (Thrombolysis), Antithrombin III (AT-III) (Hereditary AT-III deficiency, Thromboembolism), Bivalirudin (Reduce blood-clotting risk in coronary angioplasty and heparin-induced thrombocytopaenia), Darbepoetin-alpha (Treatment of anaemia in patients with chronic renal insufficiency and chronic renal failure (+/−dialysis)), Drotrecogin-alpha (activated protein C) (Severe sepsis with a high risk of death), Erythropoietin, Epoetin-alpha, erythropoetin, erthropoyetin (Anaemia of chronic disease, myleodysplasia, anaemia due to renal failure or chemotherapy, preoperative preparation), Factor IX (Haemophilia B), Factor VIIa (Haemorrhage in patients with haemophilia A or B and inhibitors to factor VIII or factor IX), Factor VIII (Haemophilia A), Lepirudin (Heparin-induced thrombocytopaenia), Protein C concentrate (Venous thrombosis, Purpura fulminans), Reteplase (deletion mutein of tPA) (Management of acute myocardial infarction, improvement of ventricular function), Streptokinase (Acute evolving transmural myocardial infarction, pulmonary embolism, deep vein thrombosis, arterial thrombosis or embolism, occlusion of arteriovenous cannula), Tenecteplase (Acute myocardial infarction), Urokinase (Pulmonary embolism), Angiostatin (Cancer), Anti-CD22 immunotoxin (Relapsed CD33+ acute myeloid leukaemia), Denileukin diftitox (Cutaneous T-cell lymphoma (CTCL)), Immunocyanin (bladder and prostate cancer), MPS (Metallopanstimulin) (Cancer), Aflibercept (Non-small cell lung cancer (NSCLC), metastatic colorectal cancer (mCRC), hormone-refractory metastatic prostate cancer, wet macular degeneration), Endostatin (Cancer, inflammatory diseases like rheumatoid arthritis as well as Crohn's disease, diabetic retinopathy, psoriasis, and endometriosis), Collagenase (Debridement of chronic dermal ulcers and severely burned areas, Dupuytren's contracture, Peyronie's disease), Human deoxy-ribonuclease I, dornase (Cystic fibrosis; decreases respiratory tract infections in selected patients with FVC greater than 40% of predicted), Hyaluronidase (Used as an adjuvant to increase the absorption and dispersion of injected drugs, particularly anaesthetics in ophthalmic surgery and certain imaging agents), Papain (Debridement of necrotic tissue or liquefication of slough in acute and chronic lesions, such as pressure ulcers, varicose and diabetic ulcers, burns, postoperative wounds, pilonidal cyst wounds, carbuncles, and other wounds), L-Asparaginase (Acute lymphocytic leukaemia, which requires exogenous asparagine for proliferation), Peg-asparaginase (Acute lymphocytic leukaemia, which requires exogenous asparagine for proliferation), Rasburicase (Paediatric patients with leukaemia, lymphoma, and solid tumours who are undergoing anticancer therapy that may cause tumour lysis syndrome), Human chorionic gonadotropin (HCG) (Assisted reproduction), Human follicle-stimulating hormone (FSH) (Assisted reproduction), Lutropin-alpha (Infertility with luteinizing hormone deficiency), Prolactin (Hypoprolactinemia, serum prolactin deficiency, ovarian dysfunction in women, anxiety, arteriogenic erectile dysfunction, premature ejaculation, oligozoospermia, asthenospermia, hypofunction of seminal vesicles, hypoandrogenism in men), alpha-1-Proteinase inhibitor (Congenital antitrypsin deficiency), Lactase (Gas, bloating, cramps and diarrhoea due to inability to digest lactose), Pancreatic enzymes (lipase, amylase, protease) (Cystic fibrosis, chronic pancreatitis, pancreatic insufficiency, post-Billroth II gastric bypass surgery, pancreatic duct obstruction, steatorrhoea, poor digestion, gas, bloating), Adenosine deaminase (pegademase bovine, PEG-ADA) (Severe combined immunodeficiency disease due to adenosine deaminase deficiency), Abatacept (Rheumatoid arthritis (especially when refractory to TNFa inhibition)), Alefacept (Plaque Psoriasis), Anakinra (Rheumatoid arthritis), Etanercept (Rheumatoid arthritis, polyarticular-course juvenile rheumatoid arthritis, psoriatic arthritis, ankylosing spondylitis, plaque psoriasis, ankylosing spondylitis), Interleukin-1 (IL-1) receptor antagonist, Anakinra (inflammation and cartilage degradation associated with rheumatoid arthritis), Thymulin (neurodegenerative diseases, rheumatism, anorexia nervosa), TNF-alpha antagonist (autoimmune disorders such as rheumatoid arthritis, ankylosing spondylitis, Crohn's disease, psoriasis, hidradenitis suppurativa, refractory asthma), Enfuvirtide (HIV-1 infection), and Thymosin al (Hepatitis B and C).

(in brackets is the particular disease for which the therapeutic protein is used in the treatment)

Furthermore adjuvant or immunostimulating proteins are also encompassed in the term therapeutic proteins. Adjuvant or immunostimulating proteins may be used in this context to induce, alter or improve an immune response in an individual to treat a particular disease or to ameliorate the condition of the individual.

In this context adjuvant proteins may be selected from mammalian, in particular human adjuvant proteins, which typically comprise any human protein or peptide, which is capable of eliciting an innate immune response (in a mammal), e.g. as a reaction of the binding of an exogenous TLR ligand to a TLR. More preferably, human adjuvant proteins are selected from the group consisting of proteins which are components and ligands of the signalling networks of the pattern recognition receptors including TLR, NLR and RLH, including TLR1, TLR2, TLR3, TLR4, TLR5, TLR6, TLR7, TLR8, TLR9, TLR10, TLR11; NOD1, NOD2, NOD3, NOD4, NOD5, NALP1, NALP2, NALP3, NALP4, NALP5, NALP6, NALP6, NALP7, NALP7, NALP8, NALP9, NALP10, NALP11, NALP12, NALP13, NALP14, 1 IPAF, NAIP, CIITA, RIG-I, MDA5 and LGP2, the signal transducers of TLR signaling including adaptor proteins including e.g. Trif and Cardif; components of the Small-GTPases signalling (RhoA, Ras, Rac1, Cdc42, Rab etc.), components of the PIP signalling (PI3K, Src-Kinases, etc.), components of the MyD88-dependent signalling (MyD88, IRAK1, IRAK2, IRAK4, TIRAP, TRAF6 etc.), components of the MyD88-independent signalling (TICAM1, TICAM2, TRAF6, TBK1, IRF3, TAK1, IRAK1 etc.); the activated kinases including e.g. Akt, MEKK1, MKK1, MKK3, MKK4, MKK6, MKK7, ERK1, ERK2, GSK3, PKC kinases, PKD kinases, GSK3 kinases, JNK, p38MAPK, TAK1, IKK, and TAK1; the activated transcription factors including e.g. NF-κB, c-Fos, c-Jun, c-Myc, CREB, AP-1, Elk-1, ATF2, IRF-3, IRF-7.

Mammalian, in particular human adjuvant proteins may furthermore be selected from the group consisting of heat shock proteins, such as HSP10, HSP60, HSP65, HSP70, HSP75 and HSP90, gp96, Fibrinogen, TypIII repeat extra domain A of fibronectin; or components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4bp, MCP, DAF, H, I, P and CD59, or induced target genes including e.g. Beta-Defensin, cell surface proteins; or human adjuvant proteins including trif, flt-3 ligand, Gp96 or fibronectin, etc., or any species homolog of any of the above human adjuvant proteins.

Mammalian, in particular human adjuvant proteins may furthermore comprise cytokines which induce or enhance an innate immune response, including IL-1 alpha, IL1 beta, IL-2, IL-6, IL-7, IL-8, IL-9, IL-12, IL-13, IL-15, IL-16, IL-17, IL-18, IL-21, IL-23, TNFalpha, IFNalpha, IFNbeta, IFNgamma, GM-CSF, G-CSF, M-CSF; chemokines including IL-8, IP-10, MCP-1, MIP-1alpha, RANTES, Eotaxin, CCL21; cytokines which are released from macrophages, including IL-1, IL-6, IL-8, IL-12 and TNF-alpha; as well as IL-1R1 and IL-1 alpha.

Therapeutic proteins for the treatment of blood disorders, diseases of the circulatory system, diseases of the respiratory system, cancer or tumour diseases, infectious diseases or immunedeficiencies or adjuvant proteins are typically proteins of mammalian origin, preferably of human origin, depending on which animal shall be treated. A human is e.g. preferably treated by a therapeutic protein of human origin.

Pathogenic adjuvant proteins, typically comprise any pathogenic adjuvant protein, which is capable of eliciting an innate immune response (in a mammal), more preferably selected from pathogenic adjuvant proteins derived from bacteria, protozoa, viruses, or fungi, etc., e.g., bacterial (adjuvant) proteins, protozoan (adjuvant) proteins (e.g. profilin-like protein of *Toxoplasma gondii*), viral (adjuvant) proteins, or fungal (adjuvant) proteins, etc.

Particularly, bacterial (adjuvant) proteins may be selected from the group consisting of bacterial heat shock proteins or chaperons, including Hsp60, Hsp70, Hsp90, Hsp100; OmpA (Outer membrane protein) from gram-negative bacteria; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from pertussis toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori*; Surfactant protein D; Outer surface protein A lipoprotein from *Borrelia burgdorferi*, Ag38 (38 kDa antigen) from *Mycobacterium tuberculosis*; proteins from bacterial fimbriae; Enterotoxin CT of *Vibrio cholerae*, Pilin from pili from gram negative bacteria, and Surfactant protein A; etc., or any species homolog of any of the above bacterial (adjuvant) proteins.

Bacterial (adjuvant) proteins may also comprise bacterial flagellins. In the context of the present invention, bacterial flagellins may be selected from flagellins from organisms including, without being limited thereto, *Agrobacterium, Aquifex, Azospirillum, Bacillus, Bartonella, Bordetella, Borrelia, Burkholderia, Campylobacter, Caulobacte, Clostridium, Escherichia, Helicobacter, Lachnospiraceae, Legionella, Listeria, Proteus, Pseudomonas, Rhizobium, Rhodobacter, Roseburia, Salmonella, Serpulina, Serratia, Shigella, Treponema, Vibrio, Wolinella, Yersinia*, more preferably from flagellins from the species including, without being limited thereto, *Agrobacterium tumefaciens, Aquifex pyrophilus, Azospirillum brasilense, Bacillus subtilis, Bacillus thuringiensis, Bartonella bacilliformis, Bordetella bronchiseptica, Borrelia burgdorferi, Burkholderia cepacia, Campylobacter jejuni, Caulobacter crescentus, Clostridium botulinum* strain Bennett clone 1, *Escherichia coli, Helicobacter pylori, Lachnospiraceae bacterium, Legionella pneumophila, Listeria monocytogenes, Proteus mirabilis, Pseudomonas aeroguinosa, Pseudomonas syringae, Rhizobium meliloti, Rhodobacter sphaeroides, Roseburia cecicola, Roseburis hominis, Salmonella typhimurium, Salmonella bongori, Salmonella typhi, Salmonella enteritidis, Serpulina hyodysenteriae, Serratia marcescens, Shigella boydii, Treponema phagedenis, Vibrio alginolyticus, Vibrio cholerae, Vibrio parahaemolyticus, Wolinella succinogenes* and *Yersinia enterocolitica*.

Protozoan (adjuvant) proteins are a further example of pathogenic adjuvant proteins. Protozoan (adjuvant) proteins may be selected in this context from any protozoan protein showing adjuvant character, more preferably, from the group consisting of, without being limited thereto, Tc52 from *Trypanosoma cruzi*, PFTG from *Trypanosoma gondii*, Protozoan heat shock proteins, LeIF from *Leishmania* spp., profiling-like protein from *Toxoplasma gondii*, etc.

Viral (adjuvant) proteins are another example of pathogenic adjuvant proteins. In this context, viral (adjuvant) proteins may be selected from any viral protein showing adjuvant character, more preferably, from the group consisting of, without being limited thereto, Respiratory Syncytial Virus fusion glycoprotein (F-protein), envelope protein from MMT virus, mouse leukemia virus protein, Hemagglutinin protein of wild-type measles virus, etc.

Fungal (adjuvant) proteins are even a further example of pathogenic adjuvant proteins. In the context of the present invention, fungal (adjuvant) proteins may be selected from any fungal protein showing adjuvant character, more preferably, from the group consisting of, fungal immunomodulatory protein (FIP; LZ-8), etc.

Finally, adjuvant proteins may furthermore be selected from the group consisting of, Keyhole limpet hemocyanin (KLH), OspA, etc.

In a further embodiment therapeutic proteins may be used for hormone replacement therapy, particularly for the therapy of women in the menopause. These therapeutic proteins are preferably selected from oestrogens, progesterone or progestins, and sometimes testosterone.

Furthermore, therapeutic proteins may be used for reprogramming of somatic cells into pluri- or omnipotent stem cells. For this purpose several factors are described, particularly Oct-3/4, Sox gene family (Sox1, Sox2, Sox3, and Sox15), Klf family (Klf1, Klf2, Klf4, and Klf5), Myc family (c-myc, L-myc, and N-myc), Nanog, and LIN28.

As mentioned above, also therapeutic antibodies are defined herein as therapeutic proteins. These therapeutic antibodies are preferably selected from antibodies which are used inter alia for the treatment of cancer or tumour diseases, e.g. 131I-tositumomab (Follicular lymphoma, B cell lymphomas, leukemias), 3F8 (Neuroblastoma), 8H9, Abagovomab (Ovarian cancer), Adecatumumab (Prostate and breast cancer), Afutuzumab (Lymphoma), Alacizumab pegol, Alemtuzumab (B-cell chronic lymphocytic leukaemia, T-cell-Lymphoma), Amatuximab, AME-133v (Follicular lymphoma, cancer), AMG 102 (Advanced Renal Cell Carcinoma), Anatumomab mafenatox (Non-small cell lung carcinoma), Apolizumab (Solid Tumors, Leukemia, Non-Hodgkin-Lymphoma, Lymphoma), Bavituximab (Cancer, viral infections), Bectumomab (Non-Hodgkin's lymphoma), Belimumab (Non-Hodgkin lymphoma), Bevacizumab (Colon Cancer, Breast Cancer, Brain and Central Nervous System Tumors, Lung Cancer, Hepatocellular Carcinoma, Kidney Cancer, Breast Cancer, Pancreatic Cancer, Bladder Cancer, Sarcoma, Melanoma, Esophageal Cancer; Stomach Cancer, Metastatic Renal Cell Carcinoma; Kidney Cancer, Glioblastoma, Liver Cancer, Proliferative Diabetic Retinopathy, Macular Degeneration), Bivatuzumab mertansine (Squamous cell carcinoma), Blinatumomab, Brentuximab vedotin (Hematologic cancers), Cantuzumab (Colon Cancer, Gastric Cancer, Pancreatic Cancer, NSCLC), Cantuzumab mertansine (Colorectal cancer), Cantuzumab ravtansine (Cancers), Capromab pendetide (Prostate cancer), Carlumab, Catumaxomab (Ovarian Cancer, Fallopian Tube Neoplasms, Peritoneal Neoplasms), Cetuximab (Metastatic colorectal cancer and head and neck cancer), Citatuzumab bogatox (Ovarian cancer and other solid tumors), Cixutumumab (Solid tumors), Clivatuzumab tetraxetan (Pancreatic cancer), CNTO 328 (B-Cell Non-Hodgkin's Lymphoma, Multiple Myeloma, Castleman's Disease, ovarian cancer), CNTO 95 (Melanoma), Conatumumab, Dacetuzumab (Hematologic cancers), Dalotuzumab, Denosumab (Myeloma, Giant Cell Tumor of Bone, Breast Cancer, Prostate Cancer, Osteoporosis), Detumomab (Lymphoma), Drozitumab, Ecromeximab (Malignant melanoma), Edrecolomab (Colorectal carcinoma), Elotuzumab (Multiple myeloma), Elsilimomab, Enavatuzumab, Ensituximab, Epratuzumab (Autoimmune diseases, Systemic Lupus Erythematosus, Non-Hodgkin-Lymphoma, Leukemia), Ertumaxomab (Breast cancer), Ertumaxomab (Breast Cancer), Etaracizumab (Melanoma, prostate cancer, ovarian cancer), Farletuzumab (Ovarian cancer), FBTA05 (Chronic lymphocytic leukaemia), Ficlatuzumab (Cancer), Figitumumab (Adrenocortical carcinoma, non-small cell lung carcinoma), Flanvotumab (Melanoma), Galiximab (B-cell lymphoma), Galiximab (Non-Hodgkin-Lymphoma), Ganitumab, GC1008 (Advanced Renal Cell Carcinoma; Malignant Melanoma, Pulmonary Fibrosis), Gemtuzumab (Leukemia), Gemtuzumab ozogamicin (Acute myelogenous leukemia), Girentuximab (Clear cell renal cell carcinoma), Glembatumumab vedotin (Melanoma, breast cancer), GS6624 (Idiopathic pulmonary fibrosis and solid tumors), HuC242-DM4 (Colon Cancer, Gastric Cancer, Pancreatic Cancer), HuHMFG1 (Breast Cancer), HuN901-DM1 (Myeloma), Ibritumomab (Relapsed or refractory low-grade, follicular, or transformed B-cell non-Hodgkin's lymphoma (NHL)), Icrucumab, IDO9C3 (Non-Hodgkin-Lymphoma), Indatuximab ravtansine, Inotuzumab ozogamicin, Intetumumab (Solid tumors (Prostate cancer, melanoma)), Ipilimumab (Sarcoma, Melanoma, Lung cancer, Ovarian Cancer leucemia, Lymphoma, Brain and Central Nervous System Tumors, Testicular Cancer, Prostate Cancer, Pancreatic Cancer, Breast Cancer), Iratumumab (Hodgkin's lymphoma), Labetuzumab (Colorectal cancer), Lexatumumab, Lintuzumab, Lorvotuzumab mertansine, Lucatumumab (Multiple myeloma, non-Hodgkin's lymphoma, Hodgkin's lymphoma), Lumiliximab (Chronic lymphocytic leukemia), Mapatumumab (Colon Cancer, Myeloma), Matuzumab (Lung Cancer, Cervical Cancer, Esophageal Cancer), MDX-060 (Hodgkin-Lymphoma, Lymphoma), MEDI 522 (Solid Tumors, Leukemia, Lymphoma, Small Intestine Cancer, Melanoma), Mitumomab (Small cell lung carcinoma), Mogamulizumab, MORab-003 (Ovarian Cancer, Fallopian Tube Cancer, Peritoneal Cancer), MORab-009 (Pancreatic Cancer, Mesothelioma, Ovarian Cancer, Non-Small Cell Lung Cancer, Fallopian Tube Cancer, Peritoneal Cavity Cancer), Moxetumomab pasudotox, MT103 (Non-Hodgkin-Lymphoma), Nacolomab tafenatox (Colorectal cancer), Naptumomab estafenatox (Non-small cell lung carcinoma, renal cell carcinoma), Narnatumab, Necitumumab (Non-small cell lung carcinoma, Nimotuzumab (Squamous cell carcinoma, head and neck cancer, nasopharyngeal cancer, glioma), Nimotuzumab (Squamous cell carcinomas, Glioma, Solid Tumors, Lung Cancer), Olaratumab, Onartuzumab (Cancer), Oportuzumab monatox, Oregovomab (Ovarian cancer), Oregovomab (Ovarian Cancer, Fallopian Tube Cancer, Peritoneal Cavity Cancer), PAM4 (Pancreatic Cancer), Panitumumab (Colon Cancer, Lung Cancer, Breast Cancer; Bladder Cancer; Ovarian Cancer), Patritumab, Pemtumomab, Pertuzumab (Breast Cancer, Ovarian Cancer, Lung Cancer, Prostate Cancer), Pritumumab (Brain cancer), Racotumomab, Radretumab, Ramucirumab (Solid tumors), Rilotumumab (Solid tumors), Rituximab (Urticaria, Rheumatoid Arthritis, Ulcerative Colitis, Chronic Focal Encephalitis, Non-Hodgkin-Lymphoma, Lymphoma, Chronic Lymphocytic Leukemia), Robatumumab, Samalizumab, SGN-30 (Hodgkin-Lymphoma, Lymphoma), SGN-40 (Non-Hodgkin-Lymphoma, Myeloma, Leukemia, Chronic Lymphocytic Leukemia), Sibrotuzumab, Siltuximab, Tabalumab (B-cell cancers), Tacatuzumab tetraxetan, Taplitumomab paptox, Tenatumomab, Teprotumumab (Hematologic tumors), TGN1412 (Chronic lymphocytic leukemia, rheumatoid arthritis), Ticilimumab (=tremelimumab), Tigatuzumab, TNX-650 (Hodgkin's lymphoma), Tositumomab (Follicular lymphoma, B cell lymphomas, Leukemias, Myeloma), Trastuzumab (Breast Cancer, Endometrial Cancer, Solid Tumors), TRB S07 (Melanoma), Tremelimumab, TRU-016 (Chronic lymphocytic leukemia), TRU-016 (Non-Hodgkin lymphoma), Tucotuzumab celmoleukin, Ublituximab, Urelumab, Veltuzumab (Non-Hodgkin's lymphoma), Veltuzumab (IMMU-106) (Non-Hodgkin's lymphoma), Volociximab (Renal Cell Carcinoma, Pancreatic Cancer, Melanoma), Votumumab (Colorectal tumors), WX-G250 (Renal Cell Carcinoma), Zalutumumab (Head and Neck Cancer, Squamous Cell Cancer), and Zanolimumab (T-Cell-Lymphoma);

antibodies which are used inter alia for the treatment of immune disorders, e.g. Efalizumab (Psoriasis), Epratuzumab (Autoimmune diseases, Systemic Lupus Erythematosus, Non-Hodgkin-Lymphoma, Leukemia), Etrolizumab (inflammatory bowel disease), Fontolizumab (Crohn's disease), Ixekizumab (autoimmune diseases), Mepolizumab (Hypereosinophilie-Syndrom, Asthma, Eosinophilic Gastroenteritis, Churg-Strauss Syndrome, Eosinophilic Esophagitis), Milatuzumab (multiple myeloma and other hematological malignancies), Pooled immunoglobulins (Primary immunodeficiencies), Priliximab (Crohn's disease, multiple sclerosis), Rituximab (Urticaria, Rheumatoid Arthritis, Ulcerative Colitis, Chronic Focal Encephalitis, Non-Hodgkin-Lymphoma, Lymphoma, Chronic Lymphocytic Leukemia), Rontalizumab (systemic lupus erythematosus), Ruplizumab (rheumatic diseases), Sarilumab (rheumatoid arthritis, ankylosing spondylitis), Vedolizumab (Crohn's disease, ulcerative colitis), Visilizumab (Crohn's disease, ulcerative colitis), Reslizumab (inflammations of the airways, skin and gastrointestinal tract), Adalimumab (Rheumatoid arthritis, Crohn's disease, Ankylosing spondylitis, Psoriatic arthritis), Aselizumab (severely injured patients), Atinumab (treatment of neurologic systems), Atlizumab (rheumatoid arthritis, systemic juvenile idiopathic arthritis), Bertilimumab (severe allergic disorders), Besilesomab (inflammatory lesions and metastases), BMS-945429, ALD518 (cancer and rheumatoid arthritis), Briakinumab (psoriasis, rheumatoid arthritis, inflammatory bowel diseases, multiple sclerosis), Brodalumab (inflammatory diseases), Canakinumab (rheumatoid arthritis), Canakinumab (cryopyrin-associated periodic syndromes (CAPS), rheumatoid arthritis, chronic obstructive pulmonary disease), Certolizumab pegol (Crohn's disease), Erlizumab (heart attack, stroke, traumatic shock), Fezakinumab (rheumatoid arthritis, psoriasis), Golimumab (rheumatoid arthritis, psoriatic arthritis, ankylosing spondylitis), Gomiliximab (allergic asthma), Infliximab (Rheumatoid arthritis, Crohn's disease, ankylosing spondylitis, psoriatic arthritis, plaque psoriasis, Morbus Bechterew, Colitis ulcerosa), Mavrilimumab (rheumatoid arthritis), Natalizumab (Multiple sclerosis), Ocrelizumab (multiple sclerosis, rheumatoid arthritis, lupus erythematosus, hematological cancer), Odulimomab (prevention of organ transplant rejections, immunological diseases), Ofatumumab (Chronic lymphocytic leukemia, follicular non-Hodgkin's lymphoma, B cell lymphoma, rheumatoid arthritis, relapsing remitting multiple sclerosis, Lymphoma, B-Cell Chronic Lymphocytic Leukemia), Ozoralizumab (inflammation), Pexelizumab (reduction of side effects of cardiac surgery), Rovelizumab (haemorrhagic shock), SBI-087 (Rheumatoid arthritis), SBI-087 (Systemic lupus erythematosus), Secukinumab (uveitis, rheumatoid arthritis psoriasis), Sirukumab (rheumatoid arthritis), Talizumab (allergic reaction), Tocilizumab (rheumatoid arthritis, systemic juvenile idiopathic arthritis, Castleman's disease), Toralizumab (rheumatoid arthritis, lupus nephritis), TRU-015 (Rheumatoid arthritis), TRU-016 (Autoimmune disease and inflammation), Ustekinumab (multiple sclerosis, psoriasis, psoriatic arthritis), Ustekinumab (IL-12/IL-23 blocker) (Plaque-Psoriasis, psoriatic arthritis, multiple sclerosis, sarcoidosis, the latter versus), Vepalimomab (inflammation), Zolimomab aritox (systemic lupus erythematosus, graft-versus-host disease), Sifalimumab (SLE, dermatomyositis, polymyositis), Lumiliximab (Allergies), and Rho(D) Immune Globulin (Rhesus disease); or are selected from antibodies used for the treatment of infectious diseases, e.g. Afelimomab (sepsis), CR6261 (infectious disease/influenza A), Edobacomab (sepsis caused by gram-negative bacteria), Efungumab (invasive Candida infection), Exbivirumab (hepatitis B), Felvizumab (respiratory syncytial virus infection), Foravirumab (rabies (prophylaxis)), Ibalizumab (HIV infection), Libivirumab (hepatitis B), Motavizumab (respiratory syncytial virus (prevention)), Nebacumab (sepsis), Tuvirumab (chronic hepatitis B), Urtoxazumab (diarrhoea caused by *E. coli*), Bavituximab (diverse viral infections), Pagibaximab (sepsis (e.g. *Staphylococcus*)), Palivizumab (prevention of respiratory syncytial virus infection in high-risk paediatric patients), Panobacumab (*Pseudomonas aeruginosa* infection), PRO 140 (HIV infection), Rafivirumab (rabies (prophylaxis)), Raxibacumab (anthrax (prophylaxis and treatment)), Regavirumab (cytomegalovirus infection), Sevirumab (cytomegalovirus infection), Suvizumab (viral infections), and Tefibazumab (*Staphylococcus aureus* infection);

antibodies which are used inter alia for the treatment of blood disorders, e.g. Abciximab (percutaneous coronary intervention), Atorolimumab (hemolytic disease of the newborn), Eculizumab (Paroxysmal nocturnal haemoglobinuria), Mepolizumab (Hypereosinophilie-Syndrom, Asthma, Eosinophilic Gastroenteritis, Churg-Strauss Syndrome, Eosinophilic Esophagitis), and Milatuzumab (multiple myeloma and other hematological malignancies);

antibodies which are used inter alia for immunoregulation, e.g. Antithymocyte globulin (Acute kidney transplant rejection, aplastic anaemia), Basiliximab (Prophylaxis against allograft rejection in renal transplant patients receiving an immunosuppressive regimen including cyclosporine and corticosteroids), Cedelizumab (prevention of organ transplant rejections, treatment of autoimmune diseases), Daclizumab (Prophylaxis against acute allograft rejection in patients receiving renal transplants, Multiple Sclerosis), Gavilimomab (graft versus host disease), Inolimomab (graft versus host disease), Muromonab-CD3 (prevention of organ transplant rejections), Muromonab-CD3 (Acute renal allograft rejection or steroid-resistant cardiac or hepatic allograft rejection), Odulimomab (prevention of organ transplant rejections, immunological diseases), and Siplizumab (psoriasis, graft-versus-host disease (prevention));

antibodies used for the treatment of diabetes, e.g. Gevokizumab (diabetes), Otelixizumab (diabetes mellitus type 1), and Teplizumab (diabetes mellitus type 1);

antibodies which are used for the treatment of the Alzheimer's disease, e.g. Bapineuzumab, Crenezumab, Gantenerumab, Ponezumab, R1450, and Solanezumab;

antibodies which are used for the treatment of asthma, e.g. Benralizumab, Enokizumab, Keliximab, Lebrikizumab, Omalizumab, Oxelumab, Pascolizumab, and Tralokinumab;

and antibodies which are used for the treatment of diverse disorders, e.g. Blosozumab (osteoporosis), CaroRx (Tooth decay), Fresolimumab (idiopathic pulmonary fibrosis, focal segmental glomerulosclerosis, cancer), Fulranumab (pain), Romosozumab (osteoporosis), Stamulumab (muscular dystrophy), Tanezumab (pain), and Ranibizumab (Neovascular age-related macular degeneration).

The coding region of the inventive nucleic acid according to the first aspect of the present invention may occur as a mono-, di-, or even multicistronic nucleic acid, i.e. a nucleic acid which carries the coding sequences of one, two or more proteins or peptides. Such coding sequences in di-, or even multicistronic nucleic acids may be separated by at least one internal ribosome entry site (IRES) sequence, e.g. as described herein or by signal peptides which induce the cleavage of the resulting polypeptide which comprises several proteins or peptides.

According to the first aspect of the present invention, the inventive nucleic acid sequence comprises a coding region, encoding a peptide or protein which comprises a therapeutic protein or a fragment, variant or derivative thereof. Preferably, the encoded therapeutic protein is no histone protein. In the context of the present invention such a histone protein is typically a strongly alkaline protein found in eukaryotic cell nuclei, which package and order the DNA into structural units called nucleosomes. Histone proteins are the chief protein components of chromatin, act as spools around which DNA winds, and play a role in gene regulation. Without histones, the unwound DNA in chromosomes would be very long (a length to width ratio of more than 10 million to one in human DNA). For example, each human cell has about 1.8 meters of DNA, but wound on the histones it has about 90 millimeters of chromatin, which, when duplicated and condensed during mitosis, result in about 120 micrometers of chromosomes.

More preferably, in the context of the present invention such a histone protein is typically defined as a highly conserved protein selected from one of the following five major classes of histones: H1/H5, H2A, H2B, H3, and H4", preferably selected from mammalian histone, more preferably from human histones or histone proteins. Such histones or histone proteins are typically organised into two superclasses defined as core histones, comprising histones H2A, H2B, H3 and H4, and linker histones, comprising histones H1 and H5.

In this context, linker histones, preferably excluded from the scope of protection of the pending invention, preferably mammalian linker histones, more preferably human linker histones, are typically selected from H1, including H1F, particularly including H1F0, H1FNT, H1FOO, H1FX, and H1H1, particularly including HIST1H1A, HIST1H1B, HIST1H1C, HIST1H1D, HIST1H1E, HIST1H1T; and Furthermore, core histones, preferably excluded from the scope of protection of the pending invention, preferably mammalian core histones, more preferably human core histones, are typically selected from H2A, including H2AF, particularly including H2AFB1, H2AFB2, H2AFB3, H2AFJ, H2AFV, H2AFX, H2AFY, H2AFY2, H2AFZ, and H2A1, particularly including HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, and H2A2, particularly including HIST2H2AA3, HIST2H2AC; H2B, including H2BF, particularly including H2BFM, H2BFO, H2BFS, H2BFWT H2B1, particularly including HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, and H2B2, particularly including HIST2H2BE; H3, including H3A1, particularly including HIST1H3A, HIST1H3B, HIST1H3C, HIST1H3D, HIST1H3E, HIST1H3F, HIST1H3G, HIST1H3H, HIST1H3I, HIST1H3J, and H3A2, particularly including HIST2H3C, and H3A3, particularly including HIST3H3; H4, including H41, particularly including HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, and H44, particularly including HIST4H4, and H5.

According to the first aspect of the present invention, the inventive nucleic acid sequence comprises a coding region, encoding a peptide or protein which comprises a therapeutic protein or a fragment, variant or derivative thereof. Preferably, the encoded therapeutic protein is no reporter protein (e.g. Luciferase, Green Fluorescent Protein (GFP), Enhanced Green Fluorescent Protein (EGFP), β-Galactosidase) and no marker or selection protein (e.g. alpha-Globin, Galactokinase and Xanthine:guanine phosphoribosyl transferase (GPT)). Preferably, the nucleic acid sequence of the invention does not contain a (bacterial) antibiotics resistance gene, in particular not a neo gene sequence (Neomycin resistance gene) or CAT gene sequence (chloramphenicol acetyl transferase, chloramphenicol resistance gene).

The inventive nucleic acid as define above, comprises or codes for a) a coding region, encoding a peptide or protein which comprises a therapeutic protein or a fragment, variant or derivative thereof; b) at least one histone stem-loop, and c) a poly(A) sequence or polyadenylation signal; preferably for increasing the expression of said encoded peptide or protein, wherein the encoded peptide or protein is preferably no histone protein, no reporter protein and/or no marker or selection protein, as defined above. The elements b) to c) of the inventive nucleic acid may occur in the inventive nucleic acid in any order, i.e. the elements a), b) and c) may occur in the order a), b) and c) or a), c) and b) from 5' to 3' direction in the inventive nucleic acid sequence, wherein further elements as described herein, may also be contained, such as a 5'-CAP structure, a poly(C) sequence, stabilization sequences, IRES sequences, etc. Each of the elements a) to c) of the inventive nucleic acid, particularly a) in di- or multicistronic constructs and/or each of the elements b) and c), more preferably element b) may also be repeated at least once, preferably twice or more in the inventive nucleic acid. As an example, the inventive nucleic acid may show its sequence elements a), b) and optionally c) in e.g. the following order:

5'-coding region-histone stem-loop-poly(A) sequence-3'; or
5'-coding region-histone stem-loop-polyadenylation signal-3'; or
5'-coding region-poly(A) sequence-histone stem-loop-3'; or
5'-coding region-polyadenylation signal-histone stem-loop-3'; or
5'-coding region-coding region-histone stem-loop-polyadenylation signal-3'; or
5'-coding region-histone stem-loop-histone stem-loop-poly(A) sequence-3'; or
5'-coding region-histone stem-loop-histone stem-loop-polyadenylation signal-3'; etc.

In this context it is particularly preferred that the inventive nucleic acid sequence comprises or codes for a) a coding region, encoding a peptide or protein which comprises a therapeutic protein or fragment, variant or derivative thereof; b) at least one histone stem-loop, and c) a poly(A) sequence or polyadenylation sequence; preferably for increasing the expression level of said encoded peptide or protein, wherein the encoded protein is preferably no histone protein, no reporter protein (e.g. Luciferase, GFP, EGFP, β-Galactosidase, particularly EGFP) and/or no marker or selection protein (e.g. alpha-Globin, Galactokinase and Xanthine:Guanine phosphoribosyl transferase (GPT)).

In a further preferred embodiment of the first aspect the inventive nucleic acid sequence as defined herein may also occur in the form of a modified nucleic acid.

In this context, the inventive nucleic acid sequence as defined herein may be modified to provide a "stabilized nucleic acid", preferably a stabilized RNA, more preferably an RNA that is essentially resistant to in vivo degradation (e.g. by an exo- or endo-nuclease). A stabilized nucleic acid may e.g. be obtained by modification of the G/C content of the coding region of the inventive nucleic acid sequence, by introduction of nucleotide analogues (e.g. nucleotides with backbone modifications, sugar modifications or base modifications) or by introduction of stabilization sequences in the 3'- and/or 5'-untranslated region of the inventive nucleic acid sequence.

As mentioned above, the inventive nucleic acid sequence as defined herein may contain nucleotide analogues/modifications e.g. backbone modifications, sugar modifications or base modifications. A backbone modification in connection with the present invention is a modification in which phosphates of the backbone of the nucleotides contained in inventive nucleic acid sequence as defined herein are chemically modified. A sugar modification in connection with the present invention is a chemical modification of the sugar of the nucleotides of the inventive nucleic acid sequence as defined herein. Furthermore, a base modification in connection with the present invention is a chemical modification of the base moiety of the nucleotides of the nucleic acid molecule of the inventive nucleic acid sequence. In this context nucleotide analogues or modifications are preferably selected from nucleotide analogues which are applicable for transcription and/or translation.

In a particular preferred embodiment of the first aspect of the present invention the herein defined nucleotide analogues/modifications are selected from base modifications which additionally increase the expression of the encoded protein and which are preferably selected from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to a further embodiment, the inventive nucleic acid sequence as defined herein can contain a lipid modification. Such a lipid-modified nucleic acid typically comprises a nucleic acid as defined herein. Such a lipid-modified nucleic acid molecule of the inventive nucleic acid sequence as defined herein typically further comprises at least one linker covalently linked with that nucleic acid molecule, and at least one lipid covalently linked with the respective linker. Alternatively, the lipid-modified nucleic acid molecule comprises at least one nucleic acid molecule as defined herein and at least one (bifunctional) lipid covalently linked (without a linker) with that nucleic acid molecule. According to a third alternative, the lipid-modified nucleic acid molecule comprises a nucleic acid molecule as defined herein, at least one linker covalently linked with that nucleic acid molecule, and at least one lipid covalently linked with the respective linker, and also at least one (bifunctional) lipid covalently linked (without a linker) with that nucleic acid molecule. In this context it is particularly preferred that the lipid modification is present at the terminal ends of a linear inventive nucleic acid sequence.

According to another preferred embodiment of the first aspect of the invention, the inventive nucleic acid sequence as defined herein, particularly if provided as an (m)RNA, can therefore be stabilized against degradation by RNases by the addition of a so-called "5' CAP" structure.

According to a further preferred embodiment of the first aspect of the invention, the inventive nucleic acid sequence as defined herein can be modified by a sequence of at least 10 cytidines, preferably at least 20 cytidines, more preferably at least 30 cytidines (so-called "poly(C) sequence"). Particularly, the inventive nucleic acid sequence may contain or code for a poly(C) sequence of typically about 10 to 200 cytidine nucleotides, preferably about 10 to 100 cytidine nucleotides, more preferably about 10 to 70 cytidine nucleotides or even preferably about 20 to 50 or even 20 to 30 cytidine nucleotides. This poly(C) sequence is preferably located 3' of the coding region comprised in the inventive nucleic acid according to the first aspect of the present invention.

In a particularly preferred embodiment of the present invention, the G/C content of the coding region, encoding at least one peptide or protein which comprises a therapeutic protein or a fragment, variant or derivative thereof of the inventive nucleic acid sequence as defined herein, is modified, particularly increased, compared to the G/C content of its particular wild type coding region, i.e. the unmodified coding region. The encoded amino acid sequence of the coding region is preferably not modified compared to the coded amino acid sequence of the particular wild type coding region.

The modification of the G/C-content of the coding region of the inventive nucleic acid sequence as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Depending on the amino acid to be encoded by the coding region of the inventive nucleic acid sequence as defined herein, there are various possibilities for modification of the nucleic acid sequence, e.g. the coding region, compared to its wild type coding region. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:
the codons for Pro can be modified from CCU or CCA to CCC or CCG;
the codons for Arg can be modified from CGU or CGA or AGA or AGG to CGC or CGG;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:
the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codon for Asn can be modified from AAU to AAC;
the codon for Lys can be modified from AAA to AAG;
the codons for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in all possible combinations to increase the G/C content of the coding region of the inventive nucleic acid sequence as defined herein, compared to its particular wild type coding region (i.e. the original sequence). Thus, for example, all codons for Thr occurring in the wild type sequence can be modified to ACC (or ACG).

In the above context, codons present in mRNA are shown. Therefore uridine present in an mRNA may also be present as thymidine in the respective DNA coding for the particular mRNA.

Preferably, the G/C content of the coding region of the inventive nucleic acid sequence as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein which comprises a therapeutic protein or a fragment, variant or derivative thereof are substituted, thereby increasing the G/C content of said coding region.

In this context, it is particularly preferable to increase the G/C content of the coding region of the inventive nucleic acid sequence as defined herein, to the maximum (i.e. 100% of the substitutable codons), compared to the wild type coding region.

According to the invention, a further preferred modification of the coding region encoding at least one peptide or protein which comprises a therapeutic protein or a fragment, variant or derivative thereof of the inventive nucleic acid sequence as defined herein, is based on the finding that the translation efficiency is also determined by a different frequency in the occurrence of tRNAs in cells. Thus, if so-called "rare codons" are present in the coding region of the inventive nucleic acid sequence as defined herein, to an increased extent, the corresponding modified nucleic acid sequence is translated to a significantly poorer degree than in the case where codons coding for relatively "frequent" tRNAs are present.

In this context the coding region of the inventive nucleic acid sequence is preferably modified compared to the corresponding wild type coding region such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the coding region of the inventive nucleic acid sequence as defined herein, is modified such that codons for which frequently occurring tRNAs are available are inserted. In other words, according to the invention, by this modification all codons of the wild type coding region which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the coding region of the inventive nucleic acid sequence as defined herein, with the "frequent" codons without modifying the amino acid sequence of the peptide or protein encoded by the coding region of the nucleic acid sequence. This preferred embodiment allows provision of a particularly efficiently translated and stabilized (modified) inventive nucleic acid sequence as defined herein.

According to another preferred embodiment of the first aspect of the invention, the inventive nucleic acid sequence as defined herein, preferably has additionally at least one 5' and/or 3' stabilizing sequence. These stabilizing sequences in the 5' and/or 3' untranslated regions have the effect of increasing the half-life of the nucleic acid, particularly of the mRNA in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from *Homo sapiens* or *Xenopus laevis* may be mentioned as an example of stabilizing sequences which can be used in the present invention for a stabilized nucleic acid. Another example of a stabilizing sequence has the general formula (C/U)CCANxCCC(U/A)PyxUC(C/U)CC (SEQ ID NO: 55) which is contained in the 3'-UTRs of the very stable RNAs which code for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. In this context it is particularly preferred that the 3' UTR sequence of the alpha globin gene is located 3' of the coding region encoding at least one peptide or protein which comprises a therapeutic protein or a fragment, variant or derivative thereof comprised in the inventive nucleic acid sequence according to the first aspect of the present invention.

Substitutions, additions or eliminations of bases are preferably carried out with the inventive nucleic acid sequence as defined herein, using a DNA matrix for preparation of the nucleic acid sequence by techniques of the well-known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N.Y., 2001).

Any of the above modifications may be applied to the inventive nucleic acid sequence as defined herein and further to any nucleic acid as used in the context of the present invention and may be, if suitable or necessary, be combined with each other in any combination, provided, these combinations of modifications do not interfere with each other in the respective nucleic acid. A person skilled in the art will be able to take his choice accordingly.

Nucleic acid sequences used according to the present invention as defined herein may be prepared using any method known in the art, including synthetic methods such as e.g. solid phase synthesis, as well as in vitro methods, such as in vitro transcription reactions or in vivo reactions, such as in vivo propagation of DNA plasmids in bacteria.

In such a process, for preparation of the inventive nucleic acid sequence as defined herein, especially if the nucleic acid is in the form of an mRNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the nucleic acid molecule, e.g. mRNA, to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

The inventive nucleic acid sequence as defined herein as well as proteins or peptides as encoded by this nucleic acid sequence may comprise fragments or variants of those sequences. Such fragments or variants may typically comprise a sequence having a sequence identity with one of the above mentioned nucleic acids, or with one of the proteins or peptides or sequences, if encoded by the inventive nucleic acid sequence, of at least 5%, 10%, 20%, 30%, 40%, 50%, 60%, preferably at least 70%, more preferably at least 80%, equally more preferably at least 85%, even more preferably at least 90% and most preferably at least 95% or even 97%, 98% or 99%, to the entire wild type sequence, either on nucleic acid level or on amino acid level.

"Fragments" of proteins or peptides in the context of the present invention (e.g. as encoded by the inventive nucleic acid sequence as defined herein) may comprise a sequence of a protein or peptide as defined herein, which is, with regard to its amino acid sequence (or its encoded nucleic acid molecule), N-terminally, C-terminally and/or intrasequentially truncated/shortened compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Likewise, "fragments" of nucleic acids in the context of the present invention may comprise a sequence of a nucleic acid as defined herein, which is, with regard to its nucleic acid molecule 5'-, 3'- and/or intrasequentially truncated/shortened compared to the nucleic acid molecule of the original (native) nucleic acid molecule. A sequence identity with respect to a fragment as defined herein may therefore preferably refer to the entire nucleic acid as defined herein and the preferred sequence identity level typically is as indicated herein. Fragments have the same biological function or specific activity or at least retain an activity of the natural full length protein of at least 50%, more preferably at least 70%, even more preferably at least 90% (measured in an appropriate functional assay, e.g. an assay assessing the enzymatic activity of the fragment of the therapeutic protein or the binding activity thereof) as compared to the full-length native wt peptide or protein, e.g. its specific antigenic or therapeutic property. Accordingly, in a preferred embodiment, the "fragment" is a portion of the full-length (naturally occurring) wt therapeutic protein, which exerts therapeutic properties as indicated herein.

Furthermore also domains of a protein, like the extracellular domain, the intracellular domain or the transmembrane domain and shortened or truncated versions of a protein may be understood to comprise/correspond to a fragment of a protein.

"Variants" of proteins or peptides as defined in the context of the present invention may be encoded by the inventive nucleic acid sequence as defined herein. Thereby, a protein or peptide may be generated, having an amino acid sequence which differs from the original sequence in one or more (2, 3, 4, 5, 6, 7 or more) mutation(s), such as one or more substituted, inserted and/or deleted amino acid(s). The preferred level of sequence identity of "variants" in view of the full-length natural wt protein sequence typically is as indicated herein. Preferably, variants have the same biological function or specific activity or at least retain an activity of the natural full length protein of at least 50%, more preferably at least 70%, even more preferably at least 90% (measured in an appropriate functional assay, e.g. an assay assessing the enzymatic activity of the variant of the therapeutic protein or the binding activity thereof) as compared to the full-length native peptide or protein, e.g. its specific therapeutic property. Accordingly, in a preferred embodiment, the "variant" is a variant of a therapeutic protein, which exerts therapeutic properties to the extent as indicated herein.

"Variants" of proteins or peptides as defined in the context of the present invention (e.g. as encoded by a nucleic acid as defined herein) may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein, which may be encoded by the inventive nucleic acid sequence as defined herein, may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by the inventive nucleic acid sequence as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

The inventive nucleic acid sequence as defined herein may encode derivatives of a peptide or protein. Such a derivative of a peptide or protein is a molecule that is derived from another molecule, such as said peptide or protein. A "derivative" typically contains the full-length sequence of the natural wt peptide or protein and additional sequence features, e.g. at the N- or at the C-terminus, which may exhibit an additional function to the natural full-length peptide/protein. Again such derivatives have the same biological function or specific activity or at least retain an activity of the natural wt full-length protein of at least 50%, more preferably at least 70%, even more preferably at least 90% (measured in an appropriate functional assay, see above, e.g. a binding or an enzyme activity assay) as compared to the full-length native peptide or protein, e.g. its specific therapeutic property. Thereby, a "derivative" of a peptide or protein also encompasses (chimeric) fusion peptides/proteins comprising a peptide or protein used in the present invention or a natural full-length protein (or variant/fragment thereof) fused to a distinct peptide/protein awarding e.g. two or more biological functions to the fusion peptide/protein. For example, the fusion may comprise a label, such as, for example, an epitope, e.g., a FLAG epitope or a V5 epitope or an HA epitope. For example, the epitope is a FLAG epitope. Such a tag is useful for, for example, purifying the fusion protein.

In this context, a "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide. Analogously, a "variant" of a nucleic acid sequence, or particularly, a fragment, may have at least 70%, 75%, 80%, 85%, 90%, 95%, 98% or 99% nucleotide identity over a stretch of 10, 20, 30, 50, 75 or 100 nucleotide of such nucleic acid sequence; typically, however, referring to the naturally occurring full-length sequences. In case of "fragments" typically, sequence identity is determined for the fragment over the length (of the fragment) on the portion of the full-length protein (reflecting the same length as the fragment), which exhibits the highest level of sequence identity.

In a further preferred embodiment of the first aspect of the present invention the inventive nucleic acid sequence is associated with a vehicle, transfection or complexation agent for increasing the transfection efficiency and/or the immunostimulatory properties of the inventive nucleic acid sequence. Particularly preferred agents in this context suitable for increasing the transfection efficiency are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l; (Lys)_m; (His)_n; (Orn)_o; (Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In this context it is particularly preferred that the inventive nucleic acid is complexed at least partially with a cationic or polycationic compound, preferably cationic proteins or peptides. Partially means that only a part of the inventive nucleic acid is complexed with a cationic or polycationic compound and that the rest of the inventive nucleic acid is in uncomplexed form ("free"). Preferably the ratio of complexed nucleic acid to:free nucleic acid is selected from a range. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed nucleic acid to free nucleic acid is selected from a ratio of about 1:1 (w/w).

It is preferred that the nucleic acid sequence of the invention is provided in either naked form or complexed, e.g. by polycationic compounds of whatever chemical structure, preferably polycationic (poly)peptides or synthetic polycationic compounds. Preferably, the nucleic acid sequence is not provided together with a packaging cell.

In a further aspect the invention provides for a composition or kit or kit of parts comprising a plurality or more than one, preferably 2 to 10, more preferably 2 to 5, most preferably 2 to 4 of the inventive nucleic acid sequences as defined herein. These inventive compositions comprise more than one inventive nucleic acid sequences, preferably encoding different peptides or proteins which comprise preferably different therapeutic proteins or fragments, variants or derivatives thereof.

According to a further aspect, the present invention also provides a method for increasing the expression of an encoded peptide or protein comprising the steps, e.g. a) providing the inventive nucleic acid sequence as defined herein or the inventive composition comprising a plurality (which means typically more than 1, 2, 3, 4, 5, 6 or more than 10 nucleic acids, e.g. 2 to 10, preferably 2 to 5 nucleic acids) of inventive nucleic acid sequences as defined herein, b) applying or administering the inventive nucleic acid sequence as defined herein or the inventive composition comprising a plurality of inventive nucleic acid sequences as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive nucleic acid sequence as defined herein or of the inventive composition comprising a plurality of inventive nucleic acid sequences as defined herein, it is typically applied or administered to a cell-free expression system, a cell (e.g. an expression host cell or a somatic cell), a tissue or an organism, e.g. in naked or complexed form or as a pharmaceutical composition as described herein, preferably via transfection or by using any of the administration modes as described herein. The method may be carried out in vitro, in vivo or ex vivo. The method may furthermore be carried out in the context of the treatment of a specific disease, preferably as defined herein.

In this context in vitro is defined herein as transfection or transduction of the inventive nucleic acid as defined herein or of the inventive composition comprising a plurality of inventive nucleic acid sequences as defined herein into cells in culture outside of an organism; in vivo is defined herein as transfection or transduction of the inventive nucleic acid or of the inventive composition comprising a plurality of inventive nucleic acid sequences (which means typically more than 1, 2, 3, 4, 5, 6 or more than 10 nucleic acids, e.g. 2 to 10, preferably 2 to 5 nucleic acids) into cells by application of the inventive nucleic acid or of the inventive composition to the whole organism or individual and ex vivo is defined herein as transfection or transduction of the inventive nucleic acid or of the inventive composition comprising a plurality of inventive nucleic acid sequences into cells outside of an organism or individual and subsequent application of the transfected cells to the organism or individual.

Likewise, according to another aspect, the present invention also provides the use of the inventive nucleic acid sequence as defined herein or of the inventive composition comprising a plurality of inventive nucleic acid sequences as defined herein, preferably for diagnostic or therapeutic purposes, for increasing the expression of an encoded peptide or protein, particularly in gene therapy e.g. by applying or administering the inventive nucleic acid sequence as defined herein or of the inventive composition comprising a plurality of inventive nucleic acid sequences as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes, preferably for gene therapy. In this context, typically after preparing the inventive nucleic acid sequence as defined herein or of the inventive composition comprising a plurality of inventive nucleic acid sequences as defined herein, it is typically applied or administered to a cell-free expression system, a cell (e.g. an expression host cell or a somatic cell), a tissue or an organism, preferably in naked form or complexed form, or as a pharmaceutical composition as described herein, preferably via transfection or by using any of the administration modes as described herein. The use may be carried out in vitro, in vivo or ex vivo. The use may furthermore be carried out in the context of the treatment of a specific disease, preferably as defined herein.

In yet another aspect the present invention also relates to an inventive expression system comprising an inventive nucleic acid sequence or expression vector or plasmid according to the first aspect of the present invention. In this context the expression system may be a cell-free expression system (e.g. an in vitro transcription/translation system), a cellular expression system (e.g. mammalian cells like CHO cells, insect cells, yeast cells, bacterial cells like E. coli) or organisms used for expression of peptides or proteins (e.g. plants or animals like cows).

Additionally, according to another aspect, the present invention also relates to the use of the inventive nucleic acid as defined herein or of the inventive composition comprising a plurality of inventive nucleic acid sequences as defined herein for the preparation of a pharmaceutical composition for increasing the expression of an encoded peptide or protein, particularly for use in gene therapy, e.g. for treating a disease, preferably as defined herein, e.g. applying or administering the inventive nucleic acid as defined herein or of the inventive composition comprising a plurality of inventive nucleic acid sequences as defined herein to a cell (e.g. an expression host cell or a somatic cell), a tissue or an organism, preferably in naked form or complexed form or as a pharmaceutical composition as described herein, more preferably using any of the administration modes as described herein.

Accordingly, in a particular preferred aspect, the present invention also provides a pharmaceutical composition, comprising an inventive nucleic acid as defined herein or an inventive composition comprising a plurality of inventive nucleic acid sequences as defined herein and optionally a pharmaceutically acceptable carrier and/or vehicle.

As a first ingredient, the inventive pharmaceutical composition comprises at least one inventive nucleic acid as defined herein.

As a second ingredient the inventive pharmaceutical composition may optional comprise at least one additional pharmaceutically active component. A pharmaceutically active component in this connection is a compound that has a therapeutic effect to heal, ameliorate or prevent a particular indication or disease as mentioned herein. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the inventive nucleic acid as defined herein in such a manner that no interaction occurs which would substantially reduce the pharmaceutical effectiveness of the inventive pharmaceutical composition under typical use conditions.

According to a specific embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive nucleic acid sequence as vehicle, transfection or complexation agent.

Further additives which may be included in the inventive pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The inventive pharmaceutical composition may be administered orally, parenterally, by inhalation spray, topically, rectally, nasally, buccally, vaginally or via an implanted reservoir.

The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

The inventive pharmaceutical composition as defined herein may also be administered orally in any orally acceptable dosage form including, but not limited to, capsules, tablets, aqueous suspensions or solutions.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive nucleic acid as defined herein suspended or dissolved in one or more carriers.

The inventive pharmaceutical composition typically comprises a "safe and effective amount" of the components of the inventive pharmaceutical composition, particularly of the inventive nucleic acid sequence(s) as defined herein. As used herein, a "safe and effective amount" means an amount of the inventive nucleic acid sequence(s) as defined herein as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

The present invention furthermore provides several applications and uses of the inventive nucleic acid sequence as defined herein, of the inventive composition comprising a plurality of inventive nucleic acid sequences as defined herein, of the inventive pharmaceutical composition, comprising the inventive nucleic acid sequence as defined herein or of kits comprising same.

According to one specific aspect, the present invention is directed to the first medical use of the inventive nucleic acid sequence as defined herein or of the inventive composition comprising a plurality of inventive nucleic acid sequences as defined herein as a medicament, particularly in gene therapy, preferably for the treatment of diseases as defined herein.

According to another aspect, the present invention is directed to the second medical use of the inventive nucleic acid sequence as defined herein or of the inventive composition comprising a plurality of inventive nucleic acid sequences as defined herein, for the treatment of diseases as defined herein, preferably to the use of the inventive nucleic acid sequence as defined herein, of the inventive composition comprising a plurality of inventive nucleic acid sequences as defined herein, of a pharmaceutical composition comprising same or of kits comprising same for the preparation of a medicament for the prophylaxis, treatment and/or amelioration of diseases as defined herein. Preferably, the pharmaceutical composition is used or to be administered to a patient in need thereof for this purpose.

Preferably, diseases as mentioned herein are preferably selected from infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system.

In this context particularly preferred are inherited diseases selected from: 1p36 deletion syndrome; 18p deletion syndrome; 21-hydroxylase deficiency; 45,X (Turner syndrome); 47,XX,+21 (Down syndrome); 47,XXX (triple X syndrome); 47,XXY (Klinefelter syndrome); 47,XY,+21 (Down syndrome); 47,XYY syndrome; 5-ALA dehydratase-deficient porphyria (ALA dehydratase deficiency); 5-aminolaevulinic dehydratase deficiency porphyria (ALA dehydratase deficiency); 5p deletion syndrome (Cri du chat) 5p-syndrome (Cri du chat); A-T (ataxia-telangiectasia); AAT (alpha-1 antitrypsin deficiency); Absence of vas deferens (congenital bilateral absence of vas deferens); Absent vasa (congenital bilateral absence of vas deferens); aceruloplasminemia; ACG2 (achondrogenesis type II); ACH (achondroplasia); Achondrogenesis type II; achondroplasia; Acid beta-glucosidase deficiency (Gaucher disease type 1); Acrocephalosyndactyly (Apert) (Apert syndrome); acrocephalosyndactyly, type V (Pfeiffer syndrome); Acrocephaly (Apert syndrome); Acute cerebral Gaucher's disease (Gaucher disease type 2); acute intermittent porphyria; ACY2 deficiency (Canavan disease); AD (Alzheimer's disease); Adelaide-type craniosynostosis (Muenke syndrome); Adenomatous Polyposis *Coli* (familial adenomatous polyposis); Adenomatous Polyposis of the Colon (familial adenomatous polyposis); ADP (ALA dehydratase deficiency); adenylosuccinate lyase deficiency; Adrenal gland disorders (21-hydroxylase deficiency); Adrenogenital syndrome (21-hydroxylase deficiency); Adrenoleukodystrophy; AIP (acute intermittent porphyria); AIS (androgen insensitivity syndrome); AKU (alkaptonuria); ALA dehydratase porphyria (ALA dehydratase deficiency); ALA-D porphyria (ALA dehydratase deficiency); ALA dehydratase deficiency; Alcaptonuria (alkaptonuria); Alexander disease; alkaptonuria; Alkaptonuric ochronosis (alkaptonuria); alpha-1 antitrypsin deficiency; alpha-1 proteinase inhibitor (alpha-1 antitrypsin deficiency); alpha-1 related emphysema (alpha-1 antitrypsin deficiency); Alpha-galactosidase A deficiency (Fabry disease); ALS (amyotrophic lateral sclerosis); Alstrom syndrome; ALX (Alexander disease); Alzheimer disease; Amelogenesis Imperfecta; Amino levulinic acid dehydratase deficiency (ALA dehydratase deficiency); Aminoacylase 2 deficiency (Canavan disease); amyotrophic lateral sclerosis; Anderson-Fabry disease (Fabry disease); androgen insensitivity syndrome; Anemia; Anemia, hereditary sideroblastic (X-linked sideroblastic anemia); Anemia, sex-linked hypochromic sideroblastic (X-linked sideroblastic anemia); Anemia, splenic, familial (Gaucher disease); Angelman syndrome; Angiokeratoma Corporis Diffusum (Fabry's disease); Angiokeratoma diffuse (Fabry's disease); Angiomatosis retinae (von Hippel-Lindau disease); ANH1 (X-linked sideroblastic anemia); APC resistance, Leiden type (factor V Leiden thrombophilia); Apert syndrome; AR deficiency (androgen insensitivity syndrome); AR-CMT2 ee (Charcot-Mare-Tooth disease, type 2); Arachnodactyly (Marfan syndrome); ARN-SHL (Nonsyndromic deafness # autosomal recessive); Arthro-ophthalmopathy, hereditary progressive (Stickler syndrome # COL2A1); Arthrochalasis multiplex congenita (Ehlers-Danlos syndrome # arthrochalasia type); AS (Angelman syndrome); Asp deficiency (Canavan disease); Aspa deficiency (Canavan disease); Aspartoacylase deficiency (Canavan disease); ataxia-telangiectasia; Autism-Dementia-Ataxia-Loss of Purposeful Hand Use syndrome (Rett syndrome); autosomal dominant juvenile ALS (amyotrophic lateral sclerosis, type 4); Autosomal dominant opitz G/BBB syndrome (22q11.2 deletion syndrome); autosomal recessive form of juvenile ALS type 3 (Amyotrophic lateral sclerosis # type 2); Autosomal recessive nonsyndromic hearing loss (Nonsyndromic deafness # autosomal recessive); Autosomal Recessive Sensorineural Hearing Impairment and Goiter (Pendred syndrome); AxD (Alexander disease); Ayerza syndrome (primary pulmonary hypertension); B variant of the Hexosaminidase GM2 gangliosidosis (Sandhoff disease); BANF (neurofibromatosis 2); Beare-Stevenson cutis gyrata syndrome; Benign paroxysmal peritonitis (Mediterranean fever, familial); Benjamin syndrome; beta thalassemia; BH4 Deficiency (tetrahydrobiopterin deficiency); Bilateral Acoustic Neurofibromatosis (neurofibromatosis 2); biotinidase deficiency; bladder cancer; Bleeding disorders (factor V Leiden thrombophilia); Bloch-Sulzberger syndrome (incontinentia pigmenti); Bloom syndrome; Bone diseases; Bone marrow diseases (X-linked sideroblastic anemia); Bonnevie-Ullrich syndrome (Turner syndrome); Bourneville disease (tuberous sclerosis); Bourneville phakomatosis (tuberous sclerosis); Brain diseases (prion disease); breast cancer; Birt-Hogg-Dubé syndrome; Brittle bone disease (osteogenesis imperfecta); Broad Thumb-Hallux syndrome (Rubinstein-Taybi syndrome); Bronze Diabetes (hemochromatosis); Bronzed cirrhosis (hemochromatosis); Bulbospinal muscular atrophy, X-linked (Kennedy disease); Burger-Grutz syndrome (lipoprotein lipase deficiency, familial); CADASIL; CGD Chronic Granulomatous Disorder; Camptomelic dysplasia; Canavan disease; Cancer; Cancer Family syndrome (hereditary nonpolyposis colorectal cancer); Cancer of breast (breast cancer); Cancer of the bladder (bladder cancer); Carboxylase Deficiency, Multiple, Late-Onset (biotinidase deficiency); Cardiomyopathy (Noonan syndrome); Cat cry syndrome (Cri du chat); CAVD (congenital bilateral absence of vas deferens); Caylor cardiofacial syndrome (22q11.2 deletion syndrome); CBAVD (congenital bilateral absence of vas deferens); Celiac Disease; CEP (congenital erythropoietic porphyria); Ceramide trihexosidase deficiency (Fabry disease); Cerebelloretinal Angiomatosis, familial (von Hippel-Lindau disease); Cerebral arteriopathy with subcortical infarcts and leukoencephalopathy (CADASIL); Cerebral autosomal dominant ateriopathy with subcortical infarcts and leukoencephalopathy (CADASIL); Cerebral sclerosis (tuberous sclerosis); Cerebroatrophic Hyperammonemia (Rett syndrome); Cerebroside Lipidosis syndrome (Gaucher disease); CF (cystic fibrosis); CH (congenital hypothyroidism); Charcot disease (amyotrophic lateral sclerosis); Charcot-Marie-Tooth disease; Chondrodystrophia (achondroplasia); Chondrodystrophy syndrome (achondroplasia); Chondrodystrophy with sensorineural deafness (otospondylomegaepiphyseal dysplasia); Chondrogenesis imperfecta (achondrogenesis, type II); Choreoathetosis self-mutilation hyperuricemia syndrome (Lesch-Nyhan syndrome); Classic Galactosemia (galactosemia); Classical Ehlers-Danlos syndrome (Ehlers-Danlos syndrome # classical type); Classical Phenylketonuria (phenylketonuria); Cleft lip and palate (Stickler syndrome); Cloverleaf skull with thanatophoric dwarfism (Thanatophoric dysplasia # type 2); CLS (Coffin-Lowry syndrome); CMT (Charcot-Marie-Tooth disease); Cockayne syndrome; Coffin-Lowry syndrome; collagenopathy, types II and XI; Colon Cancer, familial Nonpolyposis (hereditary nonpolyposis colorectal cancer); Colon cancer, familial (familial adenomatous polyposis); Colorectal Cancer; Complete HPRT deficiency (Lesch-Nyhan syndrome); Complete hypoxanthine-guanine phosphoribosy transferase deficiency (Lesch-Nyhan syndrome); Compression neuropathy (hereditary neuropathy with liability to pressure palsies); Congenital adrenal hyperplasia (21-hydroxylase deficiency); congenital bilateral absence of vas deferens (Congenital absence of the vas deferens); Congenital erythropoietic porphyria; Congenital heart disease; Congenital hypomyelination (Charcot-Marie-Tooth disease # Type 1/Charcot-Marie-Tooth disease # Type 4); Congenital hypothyroidism; Congenital methemoglobinemia (Methemoglobinemia # Congenital methaemoglobinaemia); Congenital osteosclerosis (achondroplasia); Congenital sideroblastic anaemia (X-linked sideroblastic anemia); Connective tissue disease; Conotruncal anomaly face syndrome (22q11.2 deletion syndrome); Cooley's Anemia (beta thalassemia); Copper storage disease (Wilson disease); Copper transport disease (Menkes disease); Coproporphyria, hereditary (hereditary coproporphyria); Coproporphyrinogen oxidase deficiency (hereditary coproporphyria); Cowden syndrome; CPO deficiency (hereditary coproporphyria); CPRO deficiency (hereditary coproporphyria); CPX deficiency (hereditary coproporphyria); Craniofacial dysarthrosis (Crouzon syndrome); Craniofacial Dysostosis (Crouzon syndrome); Cretinism (congenital hypothyroidism); Creutzfeldt-Jakob disease (prion disease); Cri du chat (Crohn's disease, fibrostenosing); Crouzon syndrome; Crouzon syndrome with acanthosis nigricans (Crouzonodermoskeletal syndrome); Crouzonodermoskeletal syndrome; CS (Cockayne syndrome) (Cowden syndrome); Curschmann-Batten-Steinert syndrome (myotonic dystrophy); cutis gyrata syndrome of Beare-Stevenson (Beare-Stevenson cutis gyrata syndrome); Disorder Mutation Chromosome; D-glycerate dehydrogenase deficiency (hyperoxaluria, primary); Dappled metaphysis syndrome (spondyloepimetaphyseal dysplasia, Strudwick type); DAT—Dementia Alzheimer's type (Alzheimer disease); Genetic hypercalciuria (Dent's disease); DBMD (muscular dystrophy, Duchenne and Becker types); Deafness with goiter (Pendred syndrome); Deafness-retinitis pigmentosa syndrome (Usher syndrome); Deficiency disease, Phenylalanine Hydroxylase (phenylketonuria); Degenerative nerve diseases; de Grouchy syndrome 1 (De Grouchy Syndrome); Dejerine-Sottas syndrome (Charcot-Marie-Tooth disease); Delta-aminolevulinate dehydratase deficiency porphyria (ALA dehydratase deficiency); Dementia (CADASIL); demyelinogenic leukodystrophy (Alexander disease); Dermatosparactic type of Ehlers-Danlos syndrome (Ehlers-Danlos syndrome # dermatosparaxi s type); Dermatosparaxi s (Ehlers-Danlos syndrome # dermatosparaxi s type); developmental disabilities; dHMN (Amyotrophic lateral sclerosis # type 4); DHMN-V (distal spinal muscular atrophy, type V); DHTR deficiency (androgen insensitivity syndrome); Diffuse Globoid Body Sclerosis (Krabbe disease); DiGeorge syndrome; Dihydrotestosterone receptor deficiency (androgen insensitivity syndrome); distal spinal muscular atrophy, type V; DM1 (Myotonic dystrophy # type1); DM2 (Myotonic dystrophy # type2); Down syndrome; DSMAV (distal spinal muscular atrophy, type V); DSN (Charcot-Marie-Tooth disease # type 4); DSS (Charcot-Marie-Tooth disease, type 4); Duchenne/Becker muscular dystrophy (muscular dystrophy, Duchenne and Becker types); Dwarf, achondroplastic (achondroplasia); Dwarf, thanatophoric (thanatophoric dysplasia); Dwarfism; Dwarfism-retinal atrophy-deafness syndrome (Cockayne syndrome); dysmyelinogenic leukodystrophy (Alexander disease); Dystrophia myotonica (myotonic dystrophy); dystrophia retinae pigmentosa-dysostosis syndrome (Usher syndrome); Early-Onset familial alzheimer disease (EO-FAD) (Alzheimer disease); EDS (Ehlers-Danlos syndrome); Ehlers-Danlos syndrome; Ekman-Lobstein disease (osteogenesi s imperfecta); Entrapment neuropathy (hereditary neuropathy with liability to pressure palsies); Epiloia (tuberous sclerosis); EPP (erythropoietic protoporphyria); Erythroblastic anemia (beta thalassemia); Erythrohepatic protoporphyria (erythropoietic protoporphyria); Erythroid 5-aminolevulinate synthetase deficiency (X-linked sideroblastic anemia); Erythropoietic porphyria (congenital erythropoietic porphyria); Erythropoietic protoporphyria; Erythropoietic uroporphyria (congenital erythropoietic porphyria); Eye cancer (retinoblastoma FA—Friedreich ataxia); Fabry disease; Facial injuries and disorders; Factor V Leiden thrombophilia; FALS (amyotrophic lateral sclerosis); familial acoustic neuroma (neurofibromatosis type II); familial adenomatous polyposis; familial Alzheimer disease (FAD) (Alzheimer disease); familial amyotrophic lateral sclerosis (amyotrophic lateral sclerosis); familial dysautonomia; familial fat-induced hypertriglyceridemia (lipoprotein lipase deficiency, familial); familial hemochromatosis (hemochromatosis); familial LPL deficiency (lipoprotein lipase deficiency, familial); familial nonpolyposis colon cancer (hereditary nonpolyposis colorectal cancer); familial paroxysmal polyserositis (Mediterranean fever, familial); familial PCT (porphyria cutanea tarda); familial pressure sensitive neuropathy (hereditary neuropathy with liability to pressure palsies); familial primary pulmonary hypertension (FPPH) (primary pulmonary hypertension); Familial Turner syndrome (Noonan syndrome); familial vascular leukoencephalopathy (CADASIL); FAP (familial adenomatous polyposis); FD (familial dysautonomia); Female pseudo-Turner syndrome (Noonan syndrome); Ferrochelatase deficiency (erythropoietic protoporphyria); ferroportin disease (Haemochromatosis # type 4); Fever (Mediterranean fever, familial); FG syndrome; FGFR3-associated coronal synostosis (Muenke syndrome); Fibrinoid degeneration of astrocytes (Alexander disease); Fibrocystic disease of the pancreas (cystic fibrosis); FMF (Mediterranean fever, familial); Folling disease (phenylketonuria); fra(X) syndrome (fragile X syndrome); fragile X syndrome; Fragilitas ossium (osteogenesis imperfecta); FRAXA syndrome (fragile X syndrome); FRDA (Friedreich's ataxia); Friedreich ataxia (Friedreich's ataxia); Friedreich's ataxia; FXS (fragile X syndrome); G6PD deficiency; Galactokinase deficiency disease (galactosemia); Galactose-1-phosphate uridyl-transferase deficiency disease (galactosemia); galactosemia; Galactosylceramidase deficiency disease (Krabbe disease); Galactosylceramide lipidosis (Krabbe disease); galactosylcerebrosidase deficiency (Krabbe disease); galactosylsphingosine lipidosis (Krabbe disease); GALC deficiency (Krabbe disease); GALT deficiency (galactosemia); Gaucher disease; Gaucher-like disease (pseudo-Gaucher disease); GBA deficiency (Gaucher disease type 1); GD (Gaucher's disease); Genetic brain disorders; genetic emphysema (alpha-1 antitrypsin deficiency); genetic hemochromatosis (hemochromatosis); Giant cell hepatitis, neonatal (Neonatal hemochromatosis); GLA deficiency (Fabry disease); Glioblastoma, retinal (retinoblastoma); Glioma, retinal (retinoblastoma); globoid cell leukodystrophy (GCL, GLD) (Krabbe disease); globoid cell leukoencephalopathy (Krabbe disease); Glucocerebrosidase deficiency (Gaucher disease); Glucocerebrosidosis (Gaucher disease); Glucosyl cerebroside lipidosis (Gaucher disease); Glucosylceramidase deficiency (Gaucher disease); Glucosylceramide beta-glucosidase deficiency (Gaucher disease); Glucosylceramide lipidosis (Gaucher disease); Glyceric aciduria (hyperoxaluria, primary); Glycine encephalopathy (Nonketotic hyperglycinemia); Glycolic aciduria (hyperoxaluria, primary); GM2 gangliosidosis, type 1 (Tay-Sachs disease); Goiter-deafness syndrome (Pendred syndrome); Graefe-Usher syndrome (Usher syndrome); Gronblad-Strandberg syndrome (pseudoxanthoma elasticum); Guenther porphyria (congenital erythropoietic porphyria); Gunther disease (congenital erythropoietic porphyria); Haemochromatosis (hemochromatosis); Hallgren syndrome (Usher syndrome); Harlequin Ichthyosis; Hb S disease (sickle cell anemia);

HCH (hypochondroplasia); HCP (hereditary coproporphyria); Head and brain malformations; Hearing disorders and deafness; Hearing problems in children; HEF2A (hemochromatosis # type 2); HEF2B (hemochromatosis # type 2); Hematoporphyria (porphyria); Heme synthetase deficiency (erythropoietic protoporphyria); Hemochromatoses (hemochromatosis); hemochromatosis; hemoglobin M disease (methemoglobinemia # beta-globin type); Hemoglobin S disease (sickle cell anemia); hemophilia; HEP (hepatoerythropoietic porphyria); hepatic AGT deficiency (hyperoxaluria, primary); hepatoerythropoietic porphyria; Hepatolenticular degeneration syndrome (Wilson disease); Hereditary arthro-ophthalmopathy (Stickler syndrome); Hereditary coproporphyria; Hereditary dystopic lipidosis (Fabry disease); Hereditary hemochromatosis (HHC) (hemochromatosis); Hereditary Inclusion Body Myopathy (skeletal muscle regeneration); Hereditary iron-loading anemia (X-linked sideroblastic anemia); Hereditary motor and sensory neuropathy (Charcot-Marie-Tooth disease); Hereditary motor neuronopathy (spinal muscular atrophy); Hereditary motor neuronopathy, type V (distal spinal muscular atrophy, type V); Hereditary Multiple Exostoses; Hereditary nonpolyposis colorectal cancer; Hereditary periodic fever syndrome (Mediterranean fever, familial); Hereditary Polyposis *Coli* (familial adenomatous polyposis); Hereditary pulmonary emphysema (alpha-1 antitrypsin deficiency); Hereditary resistance to activated protein C (factor V Leiden thrombophilia); Hereditary sensory and autonomic neuropathy type III (familial dysautonomia); Hereditary spastic paraplegia (infantile-onset ascending hereditary spastic paralysis); Hereditary spinal ataxia (Friedreich ataxia); Hereditary spinal sclerosis (Friedreich ataxia); Herrick's anemia (sickle cell anemia); Heterozygous OSMED (Weissenbacher-Zweymüller syndrome); Heterozygous otospondylomegaepiphyseal dysplasia (Weissenbacher-Zweymuller syndrome); HexA deficiency (Tay-Sachs disease); Hexosaminidase A deficiency (Tay-Sachs disease); Hexosaminidase alpha-subunit deficiency (variant B) (Tay-Sachs disease); FIFE-associated hemochromatosis (hemochromatosis); HGPS (Progeria); Hippel-Lindau disease (von Hippel-Lindau disease); HLAH (hemochromatosis); HMN V (distal spinal muscular atrophy, type V); HMSN (Charcot-Marie-Tooth disease); HNPCC (hereditary nonpolyposis colorectal cancer); HNPP (hereditary neuropathy with liability to pressure palsies); homocystinuria; Homogentisic acid oxidase deficiency (alkaptonuria); Homogentisic acidura (alkaptonuria); Homozygous porphyria cutanea tarda (hepatoerythropoietic porphyria); HP1 (hyperoxaluria, primary); HP2 (hyperoxaluria, primary); HPA (hyperphenylalaninemia); HPRT—Hypoxanthine-guanine phosphoribosyltransferase deficiency (Lesch-Nyhan syndrome); HSAN type III (familial dysautonomia); HSAN3 (familial dysautonomia); HSN-III (familial dysautonomia); Human dermatosparaxis (Ehlers-Danlos syndrome # dermatosparaxis type); Huntington's disease; Hutchinson-Gilford progeria syndrome (progeria); Hyperandrogenism, nonclassic type, due to 21-hydroxylase deficiency (21-hydroxylase deficiency); Hyperchylomicronemi a, familial (lipoprotein lipase deficiency, familial); hyperglycinemia with ketoacidosis and leukopenia (propionic acidemia); Hyperlipoproteinemia type I (lipoprotein lipase deficiency, familial); hyperoxaluria, primary; hyperphenylal aninaemia (hyperphenylalaninemia); hyperphenylalaninemia; Hypochondrodysplasia (hypochondroplasia); hypochondrogenesis; hypochondroplasia; Hypochromic anemia (X-linked sideroblastic anemia); Hypocupremia, congenital; Menkes syndrome); hypoxanthine phosphoribosyltransferse (HPRT) deficiency (Lesch-Nyhan syndrome); IAHSP (infantile-onset ascending hereditary spastic paralysis); idiopathic hemochromatosis (hemochromatosis, type 3); Idiopathic neonatal hemochromatosis (hemochromatosis, neonatal); Idiopathic pulmonary hypertension (primary pulmonary hypertension); Immune system disorders (X-linked severe combined immunodeficiency); Incontinentia Pigmenti; Infantile cerebral Gaucher's disease (Gaucher disease type 2); Infantile Gaucher disease (Gaucher disease type 2); infantile-onset ascending hereditary spastic paralysis; Infertility; inherited emphysema (alpha-1 antitrypsin deficiency); Inherited human transmissible spongiform encephalopathies (prion disease); inherited tendency to pressure palsies (hereditary neuropathy with liability to pressure palsies); Insley-Astley syndrome (otospondylomegaepiphyseal dysplasia); Intermittent acute porphyria syndrome (acute intermittent porphyria); Intestinal polyposis-cutaneous pigmentation syndrome (Peutz-Jeghers syndrome); IP (incontinentia pigmenti); Iron storage disorder (hemochromatosis); Isodicentric 15 (idic15); Isolated deafness (nonsyndromic deafness); Jackson-Weiss syndrome; JH (Haemochromatosis # type 2); Joubert syndrome; JPLS (Juvenile Primary Lateral Sclerosis); juvenile amyotrophic lateral sclerosis (Amyotrophic lateral sclerosis # type 2); Juvenile gout, choreoathetosis, mental retardation syndrome (Lesch-Nyhan syndrome); juvenile hyperuricemia syndrome (Lesch-Nyhan syndrome); JWS (Jackson-Weiss syndrome); KD (X-linked spinal-bulbar muscle atrophy); Kennedy disease (X-linked spinal-bulbar muscle atrophy); Kennedy spinal and bulbar muscular atrophy (X-linked spinal-bulbar muscle atrophy); Kerasin histiocytosis (Gaucher disease); Kerasin lipoidosis (Gaucher disease); Kerasin thesaurismosis (Gaucher disease); ketotic glycinemia (propionic acidemia); ketotic hyperglycinemia (propionic acidemia); Kidney diseases (hyperoxaluria, primary); Klinefelter syndrome; Klinefelter's syndrome; Kniest dysplasia; Krabbe disease; Lacunar dementia (CADASIL); Langer-Saldino achondrogenesis (achondrogenesis, type II); Langer-Saldino dysplasia (achondrogenesis, type II); Late-onset Alzheimer disease (Alzheimer disease # type 2); Late-onset familial Alzheimer disease (AD2) (Alzheimer disease # type 2); late-onset Krabbe disease (LOKD) (Krabbe disease); Learning Disorders (Learning disability); Lentiginosis, perioral (Peutz-Jeghers syndrome); Lesch-Nyhan syndrome; Leukodystrophies; leukodystrophy with Rosenthal fibers (Alexander disease); Leukodystrophy, spongiform (Canavan disease); LFS (Li-Fraumeni syndrome); Li-Fraumeni syndrome; Lipase D deficiency (lipoprotein lipase deficiency, familial); LIPD deficiency (lipoprotein lipase deficiency, familial); Lipidosis, cerebroside (Gaucher disease); Lipidosis, ganglioside, infantile (Tay-Sachs disease); Lipoid histiocytosis (kerasin type) (Gaucher disease); lipoprotein lipase deficiency, familial; Liver diseases (galactosemia); Lou Gehrig disease (amyotrophic lateral sclerosis); Louis-Bar syndrome (ataxia-telangiectasia); Lynch syndrome (hereditary nonpolyposis colorectal cancer); Lysyl-hydroxylase deficiency (Ehlers-Danlos syndrome # kyphoscoliosis type); Machado-Joseph disease (Spinocerebellar ataxia # type 3); Male breast cancer (breast cancer); Male genital disorders; Male Turner syndrome (Noonan syndrome); Malignant neoplasm of breast (breast cancer); malignant tumor of breast (breast cancer); Malignant tumor of urinary bladder (bladder cancer); Mammary cancer (breast cancer); Marfan syndrome 15; Marker X syndrome (fragile X syndrome); Martin-Bell syndrome (fragile X syndrome); McCune-Albright syndrome; McLeod syndrome; MEDNIK; Mediterranean Anemia (beta thalassemia); Mediterranean fever, familial;

Mega-epiphyseal dwarfism (otospondylomegaepiphyseal dysplasia); Menkea syndrome (Menkes syndrome); Menkes syndrome; Mental retardation with osteocartilaginous abnormalities (Coffin-Lowry syndrome); Metabolic disorders; Metatropic dwarfism, type II (Kniest dysplasia); Metatropic dysplasia type II (Kniest dysplasia); Methemoglobinemia # beta-globin type; methylmalonic acidemia; MFS (Marfan syndrome); MHAM (Cowden syndrome); MK (Menkes syndrome); Micro syndrome; Microcephaly; MMA (methylmalonic acidemia); MNK (Menkes syndrome); Monosomy 1p36 syndrome (1p36 deletion syndrome); monosomy X (Turner syndrome); Motor neuron disease, amyotrophic lateral sclerosis (amyotrophic lateral sclerosis); Movement disorders; Mowat-Wilson syndrome; Mucopolysaccharidosis (MPS I); Mucoviscidosis (cystic fibrosis); Muenke syndrome; Multi-Infarct dementia (CADASIL); Multiple carboxylase deficiency, late-onset (biotinidase deficiency); Multiple hamartoma syndrome (Cowden syndrome); Multiple neurofibromatosi s (neurofibromatosi s); Muscular dystrophy; Muscular dystrophy, Duchenne and Becker type; Myotonia atrophica (myotonic dystrophy); Myotonia dystrophica (myotonic dystrophy); myotonic dystrophy; Myxedema, congenital (congenital hypothyroidism); Nance-Insley syndrome (otospondylomegaepiphyseal dysplasia); Nance-Sweeney chondrodysplasia (otospondylomegaepiphyseal dysplasia); NBIA1 (pantothenate kinase-associated neurodegeneration); Neill-Dingwall syndrome (Cockayne syndrome); Neuroblastoma, retinal (retinoblastoma); Neurodegeneration with brain iron accumulation type 1 (pantothenate kinase-associated neurodegeneration); Neurofibromatosis type I; Neurofibromatosis type II; Neurologic diseases; Neuromuscular disorders; neuronopathy, distal hereditary motor, type V (Distal spinal muscular atrophy # type V); neuronopathy, distal hereditary motor, with pyramidal features (Amyotrophic lateral sclerosis # type 4); NF (neurofibromatosis); Niemann-Pick (Niemann-Pick disease); Noack syndrome (Pfeiffer syndrome); Nonketotic hyperglycinemia (Glycine encephalopathy); Non-neuronopathic Gaucher disease (Gaucher disease type 1); Non-phenylketonuric hyperphenylalaninemia (tetrahydrobiopterin deficiency); nonsyndromic deafness; Noonan syndrome; Norrbottnian Gaucher disease (Gaucher disease type 3); Ochronosis (alkaptonuria); Ochronotic arthritis (alkaptonuria); OI (osteogenesis imperfecta); OSMED (otospondylomegaepiphyseal dysplasia); osteogenesis imperfecta; Osteopsathyrosis (osteogenesis imperfecta); Osteosclerosis congenita (achondroplasia); Oto-spondylomegaepiphyseal dysplasia (otospondylomegaepiphyseal dysplasia); otospondylomegaepiphyseal dysplasia; Oxalosis (hyperoxaluria, primary); Oxaluria, primary (hyperoxaluria, primary); pantothenate kinase-associated neurodegeneration; Patau Syndrome (Trisomy 13); PBGD deficiency (acute intermittent porphyria); PCC deficiency (propionic acidemia); PCT (porphyria cutanea tarda); PDM (Myotonic dystrophy # type 2); Pendred syndrome; Periodic disease (Mediterranean fever, familial); Periodic peritonitis (Mediterranean fever, familial); Periorificial lentiginosis syndrome (Peutz-Jeghers syndrome); Peripheral nerve disorders (familial dysautonomia); Peripheral neurofibromatosis (neurofibromatosis 1); Peroneal muscular atrophy (Charcot-Marie-Tooth disease); peroxisomal alanine:glyoxylate aminotransferase deficiency (hyperoxaluria, primary); Peutz-Jeghers syndrome; Pfeiffer syndrome; Phenylalanine hydroxylase deficiency disease (phenylketonuria); phenylketonuria; Pheochromocytoma (von Hippel-Lindau disease); Pierre Robin syndrome with fetal chondrodysplasia (Wei ssenbacher-Zweymüller syndrome); Pigmentary cirrhosis (hemochromatosis); PJS (Peutz-Jeghers syndrome); PKAN (pantothenate kinase-associated neurodegeneration); PKU (phenylketonuria); Plumboporphyria (ALA deficiency porphyria); PMA (Charcot-Marie-tooth disease); polyostotic fibrous dysplasia (McCune-Albright syndrome); polyposis coli (familial adenomatous polyposis); polyposis, hamartomatous intestinal (Peutz-Jeghers syndrome); polyposis, intestinal, II (Peutz-Jeghers syndrome); polyps-and-spots syndrome (Peutz-Jeghers syndrome); Porphobilinogen synthase deficiency (ALA deficiency porphyria); porphyria; porphyrin disorder (porphyria); PPH (primary pulmonary hypertension); PPDX deficiency (variegate porphyria); Prader-Labhart-Willi syndrome (Prader-Willi syndrome); Prader-Willi syndrome; presenile and senile dementia (Alzheimer disease); primary hemochromatosis (hemochromatosis); primary hyperuricemia syndrome (Lesch-Nyhan syndrome); primary pulmonary hypertension; primary senile degenerative dementia (Alzheimer disease); prion disease; procollagen type EDS VII, mutant (Ehlers-Danlos syndrome # arthrochalasia type); progeria (Hutchinson Gilford Progeria Syndrome); Progeria-like syndrome (Cockayne syndrome); progeroid nanism (Cockayne syndrome); progressive chorea, chronic hereditary (Huntington) (Huntington's disease); progressive muscular atrophy (spinal muscular atrophy); progressively deforming osteogenesis imperfecta with normal sclerae (Osteogenesis imperfecta # type III); PROMM (Myotonic dystrophy # type 2); propionic academia; propionyl-CoA carboxylase deficiency (propionic acidemia); protein C deficiency; protein S deficiency; protoporphyria (erythropoietic protoporphyria); protoporphyrinogen oxidase deficiency (variegate porphyria); proximal myotonic dystrophy (Myotonic dystrophy # type 2); proximal myotonic myopathy (Myotonic dystrophy # type 2); pseudo-Gaucher disease; pseudo-Ullrich-Turner syndrome (Noonan syndrome); pseudoxanthoma elasticum; psychosine lipidosis (Krabbe disease); pulmonary arterial hypertension (primary pulmonary hypertension); pulmonary hypertension (primary pulmonary hypertension); PWS (Prader-Willi syndrome); PXE—pseudoxanthoma elasticum (pseudoxanthoma elasticum); Rb (retinoblastoma); Recklinghausen disease, nerve (neurofibromatosis 1); Recurrent polyserositis (Mediterranean fever, familial); Retinal disorders; Retinitis pigmentosa-deafness syndrome (Usher syndrome); Retinoblastoma; Rett syndrome; RFALS type 3 (Amyotrophic lateral sclerosis # type 2); Ricker syndrome (Myotonic dystrophy # type 2); Riley-Day syndrome (familial dysautonomia); Roussy-Levy syndrome (Charcot-Marie-Tooth disease); RSTS (Rubinstein-Taybi syndrome); RTS (Rett syndrome) (Rubinstein-Taybi syndrome); RTT (Rett syndrome); Rubinstein-Taybi syndrome; Sack-Barabas syndrome (Ehlers-Danlos syndrome, vascular type); SADDAN; sarcoma family syndrome of Li and Fraumeni (Li-Fraumeni syndrome); sarcoma, breast, leukemia, and adrenal gland (SBLA) syndrome (Li-Fraumeni syndrome); SBLA syndrome (Li-Fraumeni syndrome); SBMA (X-linked spinal-bulbar muscle atrophy); SCD (sickle cell anemia); Schwannoma, acoustic, bilateral (neurofibromatosis 2); SCIDX1 (X-linked severe combined immunodeficiency); sclerosis tuberosa (tuberous sclerosis); SDAT (Alzheimer disease); SED congenita (spondyloepiphyseal dysplasia congenita); SED Strudwick (spondyloepimetaphyseal dysplasia, Strudwick type); SEDc (spondyloepiphyseal dysplasia congenita); SEMD, Strudwick type (spondyloepimetaphyseal dysplasia, Strudwick type); senile dementia (Alzheimer disease # type 2); severe achondroplasia with developmental delay and acanthosis nigricans (SADDAN); Shprintzen syndrome (22q11.2 deletion syndrome); sickle cell anemia;

skeleton-skin-brain syndrome (SADDAN); Skin pigmentation disorders; SMA (spinal muscular atrophy); SMED, Strudwick type (spondyloepimetaphyseal dysplasia, Strudwick type); SMED, type I (spondyloepimetaphyseal dysplasia, Strudwick type); Smith Lemli Opitz Syndrome; South-African genetic porphyria (variegate porphyria); spastic paralysis, infantile onset ascending (infantile-onset ascending hereditary spastic paralysis); Speech and communication disorders; sphingolipidosis, Tay-Sachs (Tay-Sachs disease); spinal-bulbar muscular atrophy; spinal muscular atrophy; spinal muscular atrophy, distal type V (Distal spinal muscular atrophy # type V); spinal muscular atrophy, distal, with upper limb predominance (Distal spinal muscular atrophy # type V); spinocerebellar ataxia; spondyloepimetaphyseal dysplasia, Strudwick type; spondyloepiphyseal dysplasia congenital; spondyloepiphyseal dysplasia (collagenopathy, types II and XI); spondylometaepiphyseal dysplasia congenita, Strudwick type (spondyloepimetaphyseal dysplasia, Strudwick type); spondylometaphyseal dysplasia (SMD) (spondyloepimetaphyseal dysplasia, Strudwick type); spondylometaphyseal dysplasia, Strudwick type (spondyloepimetaphyseal dysplasia, Strudwick type); spongy degeneration of central nervous system (Canavan disease); spongy degeneration of the brain (Canavan disease); spongy degeneration of white matter in infancy (Canavan disease); sporadic primary pulmonary hypertension (primary pulmonary hypertension); SSB syndrome (SADDAN); steely hair syndrome (Menkes syndrome); Steinert disease (myotonic dystrophy); Steinert myotonic dystrophy syndrome (myotonic dystrophy); Stickler syndrome; stroke (CADASIL); Strudwick syndrome (spondyloepimetaphyseal dysplasia, Strudwick type); subacute neuronopathic Gaucher disease (Gaucher disease type 3); Swedish genetic porphyria (acute intermittent porphyria); Swedish porphyria (acute intermittent porphyria); Swiss cheese cartilage dysplasia (Kniest dysplasia); Tay-Sachs disease; TD—thanatophoric dwarfism (thanatophoric dysplasia); TD with straight femurs and cloverleaf skull (thanatophoric dysplasia # Type 2); Telangiectasia, cerebello-oculocutaneous (ataxia-telangiectasia); Testicular feminization syndrome (androgen insensitivity syndrome); tetrahydrobiopterin deficiency; TFM—testicular feminization syndrome (androgen insensitivity syndrome); thalassemia intermedia (beta thalassemia); Thalassemia Major (beta thalassemia); thanatophoric dysplasia; thiamine-responsive megaloblastic anemia with diabetes mellitus and sensorineural deafness; Thrombophilia due to deficiency of cofactor for activated protein C, Leiden type (factor V Leiden thrombophilia); Thyroid disease; Tomaculous neuropathy (hereditary neuropathy with liability to pressure palsies); Total HPRT deficiency (Lesch-Nyhan syndrome); Total hypoxanthine-guanine phosphoribosyl transferase deficiency (Lesch-Nyhan syndrome); Tourette's Syndrome; Transmissible dementias (prion disease); Transmissible spongiform encephalopathies (prion disease); Treacher Collins syndrome; Trias fragilitis ossium (osteogenesis imperfecta # Type I); triple X syndrome; Triplo X syndrome (triple X syndrome); Trisomy 21 (Down syndrome); Trisomy X (triple X syndrome); Troisier-Hanot-Chauffard syndrome (hemochromatosis); TS (Turner syndrome); TSD (Tay-Sachs disease); TSEs (prion disease); tuberose sclerosis (tuberous sclerosis); tuberous sclerosis; Turner syndrome; Turner syndrome in female with X chromosome (Noonan syndrome); Turner's phenotype, karyotype normal (Noonan syndrome); Turner's syndrome (Turner syndrome); Turner-like syndrome (Noonan syndrome); Type 2 Gaucher disease (Gaucher disease type 2); Type 3 Gaucher disease (Gaucher disease type 3); UDP-galactose-4-epimerase deficiency disease (galactosemia); UDP glucose 4-epimerase deficiency disease (galactosemia); UDP glucose hexose-1-phosphate uridylyltransferase deficiency (galactosemia); Ullrich-Noonan syndrome (Noonan syndrome); Ullrich-Turner syndrome (Turner syndrome); Undifferentiated deafness (nonsyndromic deafness); UPS deficiency (acute intermittent porphyria); Urinary bladder cancer (bladder cancer); UROD deficiency (porphyria cutanea tarda); Uroporphyrinogen decarboxylase deficiency (porphyria cutanea tarda); Uroporphyrinogen synthase deficiency (acute intermittent porphyria); UROS deficiency (congenital erythropoietic porphyria); Usher syndrome; UTP hexose-1-phosphate uridylyltransferase deficiency (galactosemia); Van Bogaert-Bertrand syndrome (Canavan disease); Van der Hoeve syndrome (osteogenesis imperfecta # Type I); variegate porphyria; Velocardiofacial syndrome (22q11.2 deletion syndrome); VHL syndrome (von Hippel-Lindau disease); Vision impairment and blindness (Alstrom syndrome); Von Bogaert-Bertrand disease (Canavan disease); von Hippel-Lindau disease; Von Recklenhausen-Applebaum disease (hemochromatosis); von Recklinghausen disease (neurofibromatosis 1); VP (variegate porphyria); Vrolik disease (osteogenesis imperfecta); Waardenburg syndrome; Warburg Sjo Fledelius Syndrome (Micro syndrome); WD (Wilson disease); Weissenbacher-Zweymtiller syndrome; Wilson disease; Wilson's disease (Wilson disease); Wolf-Hirschhorn syndrome; Wolff Periodic disease (Mediterranean fever, familial); WZS (Weissenbacher-Zweymtiller syndrome); Xeroderma Pigmentosum; X-linked mental retardation and macroorchidism (fragile X syndrome); X-linked primary hyperuricemia (Lesch-Nyhan syndrome); X-linked severe combined immunodeficiency; X-linked sideroblastic anemia; X-linked spinal-bulbar muscle atrophy (Kennedy disease); X-linked uric aciduria enzyme defect (Lesch-Nyhan syndrome); X-SCID (X-linked severe combined immunodeficiency); XLSA (X-linked sideroblastic anemia); XSCID (X-linked severe combined immunodeficiency); XXX syndrome (triple X syndrome); XXXX syndrome (48, XXXX); XXXXX syndrome (49, XXXXX); XXY syndrome (Klinefelter syndrome); XXY trisomy (Klinefelter syndrome); XYY karyotype (47,XYY syndrome); XYY syndrome (47,XYY syndrome); and YY syndrome (47,XYY syndrome).

In a further preferred aspect, the inventive nucleic acid sequence as defined herein or the inventive composition comprising a plurality of inventive nucleic acid sequences as defined herein may be used for the preparation of a pharmaceutical composition, particularly for purposes as defined herein, preferably for the use in gene therapy in the treatment of diseases as defined herein.

The inventive pharmaceutical composition may furthermore be used in gene therapy particularly in the treatment of a disease or a disorder, preferably as defined herein.

According to a final aspect, the present invention also provides kits, particularly kits of parts. Such kits, particularly kits of parts, typically comprise as components alone or in combination with further components as defined herein at least one inventive nucleic acid sequence as defined herein, the inventive pharmaceutical composition or vaccine comprising the inventive nucleic acid sequence. The at least one inventive nucleic acid sequence as defined herein, is optionally in combination with further components as defined herein, whereby the at least one nucleic acid of the invention is provided separately (first part of the kit) from at least one other part of the kit comprising one or more other components. The inventive pharmaceutical composition may e.g. occur in one or different parts of the kit. As an example, e.g.

at least one part of the kit may comprise at least one inventive nucleic acid sequence as defined herein, and at least one further part of the kit at least one other component as defined herein, e.g. at least one other part of the kit may comprise at least one pharmaceutical composition or a part thereof, e.g. at least one part of the kit may comprise the inventive nucleic acid sequence as defined herein, at least one further part of the kit at least one other component as defined herein, at least one further part of the kit at least one component of the inventive pharmaceutical composition or the inventive pharmaceutical composition as a whole, and at least one further part of the kit e.g. at least one pharmaceutical carrier or vehicle, etc. In case the kit or kit of parts comprises a plurality of inventive nucleic acid sequences, one component of the kit can comprise only one, several or all inventive nucleic acid sequences comprised in the kit. In an alternative embodiment every/each inventive nucleic acid sequence may be comprised in a different/separate component of the kit such that each component forms a part of the kit. Also, more than one nucleic acid may be comprised in a first component as part of the kit, whereas one or more other (second, third etc.) components (providing one or more other parts of the kit) may either contain one or more than one inventive nucleic acids, which may be identical or partially identical or different from the first component. The kit or kit of parts may furthermore contain technical instructions with information on the administration and dosage of the inventive nucleic acid sequence, the inventive pharmaceutical composition or of any of its components or parts, e.g. if the kit is prepared as a kit of parts.

Taken together, the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, may be a therapeutic protein,
preferably a therapeutic protein for use in the treatment of metabolic or endocrine disorders, for use in the treatment of blood disorders, diseases of the circulatory system, diseases of the respiratory system, cancer or tumour diseases, infectious diseases or immunedeficiencies, for use in hormone replacement therapy or for use in reprogramming of somatic cells
or a therapeutic protein selected from from adjuvant or immunostimulating proteins, human adjuvant proteins, bacterial (adjuvant) proteins, protozoan (adjuvant) proteins, viral (adjuvant) proteins, fungal (adjuvant) proteins
or an antibody, preferably an antibody selected from antibodies used for the treatment of cancer or tumour diseases, antibodies used for the treatment of immune disorders, antibodies used for the treatment of infectious diseases, antibodies used for the treatment of infectious diseases, antibodies used for the treatment of blood disorders, antibodies used for immunoregulation, antibodies used for the treatment of diabetes, antibodies used for the treatment of the Alzheimer's disease, antibodies used for the treatment of asthma or antibodies for the treatment of diverse disorders.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably, the invention provides a nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, may be a therapeutic protein
for use in the treatment of metabolic or endocrine disorders,
for use in the treatment of blood disorders, diseases of the circulatory system, diseases of the respiratory system, cancer or tumour diseases, infectious diseases or immunedeficiencies,
for use in hormone replacement therapy or
for use in reprogramming of somatic cells.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Further preferably, the invention provides a nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein selected from adjuvant or immunostimulating proteins, more preferably selected from human adjuvant proteins, bacterial (adjuvant) proteins, protozoan (adjuvant) proteins, viral (adjuvant) proteins, fungal (adjuvant) proteins.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or the composition to a cell-free expression system, a cell, a tissue or an organism.

Further preferably, the invention provides a nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein or a fragment, variant or derivative thereof which is a therapeutic antibody, more preferably an antibody selected from antibodies used for the treatment of cancer or tumour diseases, antibodies used for the treatment of immune disorders, antibodies used for the treatment of infectious diseases, antibodies used for the treatment of infectious diseases, antibodies used for the treatment of blood disorders, antibodies used for immunoregulation, antibodies used for the treatment of diabetes, antibodies used for the treatment of the Alzheimer's disease, antibodies used for the treatment of asthma or antibodies for the treatment of diverse disorders.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides a nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein for use in the treatment of metabolic or endocrine disorders,
more preferably a peptide or protein selected from Acid sphingomyelinase, Adipotide, Agalsidase-beta, Alglucosidase, alpha-galactosidase A, alpha-glucosidase, alpha-L-iduronidase, alpha-N-acetylglucosaminidase, Amphiregulin, Angiopoietins (Ang1, Ang2, Ang3, Ang4, ANGPTL2, ANGPTL3, ANGPTL4, ANGPTL5, ANGPTL6, ANGPTL7), Betacellulin, Beta-glucuronidase, Bone morphogenetic proteins BMPs (BMP1, BMP2, BMP3, BMP4, BMP5, BMP6, BMP7, BMP8a, BMP8b, BMP10, BMP15), CLN6 protein, Epidermal growth factor (EGF), Epigen, Epiregulin, Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23), Galsulphase, Ghrelin, Glucocerebrosidase, GM-CSF, Heparin-binding EGF-like growth factor (HB-EGF), Hepatocyte growth factor HGF, Hepcidin, Human albumin, increased loss of albumin, Idursulphase (Iduronate-2-sulphatase), Integrins $\alpha V\beta 3$, $\alpha V\beta 5$ and $\alpha 5\beta 1$, Iuduronate sulfatase, Laronidase, N-acetylgalactosamine-4-sulfatase (rhASB; galsulfase, Arylsulfatase A (ARSA), Arylsulfatase B (ARSB)), N-acetylglucosamine-6-sulfatase, Nerve growth factor (NGF, Brain-Derived Neurotrophic Factor (BDNF), Neurotrophin-3 (NT-3), and Neurotrophin 4/5 (NT-4/5), Neuregulin (NRG1, NRG2, NRG3, NRG4), Neuropilin (NRP-1, NRP-2), Obestatin, Platelet Derived Growth factor (PDGF (PDFF-A, PDGF-B, PDGF-C, PDGF-D), TGF beta receptors (endoglin, TGF-beta 1 receptor, TGF-beta 2 receptor, TGF-beta 3 receptor), Thrombopoietin (THPO) (Megakaryocyte growth and development factor (MGDF)), Transforming Growth factor (TGF (TGF-a, TGF-beta (TGFbeta1, TGFbeta2, and TGF-beta3))), VEGF (VEGF-A, VEGF-B, VEGF-C, VEGF-D, VEGF-E, VEGF-F and PlGF), Nesiritide, Trypsin, adrenocorticotrophic hormone (ACTH), Atrial-natriuretic peptide (ANP), Cholecystokinin, Gastrin, Leptin, Oxytocin, Somatostatin, Vasopressin (antidiuretic hormone), Calcitonin, Exenatide, Growth hormone (GH), somatotropin, Insulin, Insulin-like growth factor 1 IGF-1, Mecasermin rinfabate, IGF-1 analog, Mecasermin, IGF-1 analog, Pegvisomant, Pramlintide, Teriparatide (human parathyroid hormone residues 1-34), Becaplermin, Dibotermin-alpha (Bone morphogenetic protein 2), Histrelin acetate (gonadotropin releasing hormone; GnRH), Octreotide, and Palifermin (keratinocyte growth factor; KGF).

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or the composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein for use in the treatment of blood disorders, diseases of the circulatory system, diseases of the respiratory system, cancer or tumour diseases, infectious diseases or immunedeficiencies, more preferably a peptide or protein selected from Alteplase (tissue plasminogen activator; tPA), Anistreplase, Antithrombin III (AT-III), Bivalirudin, Darbepoetin-alpha, Drotrecogin-alpha (activated protein C, Erythropoietin, Epoetin-alpha, erythropoetin, erthropoyetin, Factor IX, Factor VIIa, Factor VIII, Lepirudin, Protein C concentrate, Reteplase (deletion mutein of tPA), Streptokinase, Tenecteplase, Urokinase, Angiostatin, Anti-CD22 immunotoxin, Denileukin diftitox, Immunocyanin, MPS (Metallopanstimulin), Aflibercept, Endostatin, Collagenase, Human deoxyribonuclease I, dornase, Hyaluronidase, Papain, L-Asparaginase, Peg-asparaginase, Rasburicase, Human chorionic gonadotropin (HCG), Human follicle-stimulating hormone (FSH), Lutropin-alpha, Prolactin, alpha-1-Proteinase inhibitor, Lactase, Pancreatic enzymes (lipase, amylase, protease), Adenosine deaminase (pegademase bovine, PEG-ADA), Abatacept, Alefacept, Anakinra, Etanercept, Interleukin-1 (IL-1) receptor antagonist, Anakinra, Thymulin, TNF-alpha antagonist, Enfuvirtide, and Thymosin al.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic protein used for hormone replacement therapy, more preferably a peptide or protein selected from oestrogens, progesterone or progestins, and testosterone.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism. Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic protein used for reprogramming of somatic cells into pluri- or omnipotent stem cells, more preferably a peptide or protein selected from Oct-3/4, Sox gene family (Sox1, Sox2, Sox3, and Sox15), Klf family (Klf1, Klf2, Klf4, and Klf5), Myc family (c-myc, L-myc, and N-myc), Nanog, and LIN28.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism. Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic protein selected from adjuvant or immunostimulating proteins, human adjuvant proteins, bacterial (adjuvant) proteins, protozoan (adjuvant) proteins, viral (adjuvant) proteins, fungal (adjuvant) proteins.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic protein selected from adjuvant or immunostimulating proteins, human adjuvant proteins, bacterial (adjuvant) proteins, protozoan (adjuvant) proteins, viral (adjuvant) proteins, fungal (adjuvant) proteins, more preferably selected from human adjuvant proteins, most preferably selected from pattern recognition receptors TLR1, TLR2, TLR3, TLR4, TLR5, TLR6, TLR7, TLR8, TLR9, TLR10, TLR11; NOD1, NOD2, NOD3, NOD4, NOD5, NALP1, NALP2, NALP3, NALP4, NALP5, NALP6, NALP6, NALP7, NALP7, NALP8, NALP9, NALP10, NALP11, NALP12, NALP13, NALP14, 1 IPAF, NAIP, CIITA, RIG-I, MDA5 and LGP2, the signal transducers of TLR signaling including adaptor proteins including e.g. Trif and Cardif; components of the Small-GTPases signalling (RhoA, Ras, Rac1, Cdc42, Rab etc.), components of the PIP signalling (PI3K, Src-Kinases, etc.), components of the MyD88-dependent signalling (MyD88, IRAK1, IRAK2, IRAK4, TIRAP, TRAF6 etc.), components of the MyD88-independent signalling (TICAM1, TICAM2, TRAF6, TBK1, IRF3, TAK1, IRAK1 etc.); the activated kinases including e.g. Akt, MEKK1, MKK1, MKK3, MKK4, MKK6, MKK7, ERK1, ERK2, GSK3, PKC kinases, PKD kinases, GSK3 kinases, JNK, p38MAPK, TAK1, IKK, and TAK1; the activated transcription factors including e.g. NF-κB, c-Fos, c-Jun, c-Myc, CREB, AP-1, Elk-1, ATF2, IRF-3, IRF-7, heat shock proteins, such as HSP10, HSP60, HSP65, HSP70, HSP75 and HSP90, gp96, Fibrinogen, TypIII repeat extra domain A of fibronectin; or components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4 bp, MCP, DAF, H, I, P and CD59, or induced target genes including e.g. Beta-Defensin, cell surface proteins; or human adjuvant proteins including trif, flt-3 ligand, Gp96 or fibronectin, cytokines which induce or enhance an innate immune response, including IL-1 alpha, IL1 beta, IL-2, IL-6, IL-7, IL-8, IL-9, IL-12, IL-13, IL-15, IL-16, IL-17, IL-18, IL-21, IL-23, TNFalpha, IFNalpha, IFNbeta, IFNgamma, GM-CSF, G-CSF, M-CSF; chemokines including IL-8, IP-10, MCP-1, MIP-1alpha, RANTES, Eotaxin, CCL21; cytokines which are released from macrophages, including IL-1, IL-6, IL-8, IL-12 and TNF-alpha; as well as IL-1R1 and IL-1 alpha.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein selected from adjuvant or immunostimulating proteins, human adjuvant proteins, bacterial (adjuvant) proteins, protozoan (adjuvant) proteins, viral (adjuvant) proteins, fungal (adjuvant) proteins, more preferably selected from bacterial (adjuvant) proteins, most preferably selected from bacterial heat shock proteins or chaperons, including Hsp60, Hsp70, Hsp90, Hsp100; OmpA (Outer membrane protein) from gram-negative bacteria; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from pertussis toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori*; Surfactant protein D; Outer surface protein A lipoprotein from *Borrelia burgdorferi*, Ag38 (38 kDa antigen) from *Mycobacterium tuberculosis*; proteins from bacterial fimbriae; Enterotoxin CT of *Vibrio cholerae*, Pilin from pili from gram negative bacteria, and Surfactant protein A and bacterial flagellins.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein selected from adjuvant or immunostimulating proteins, human adjuvant proteins, bacterial (adjuvant) proteins, protozoan (adjuvant) proteins, viral (adjuvant) proteins, fungal (adjuvant) proteins, more preferably selected from protozoan (adjuvant) proteins, most preferably selected from Tc52 from *Trypanosoma cruzi*, PFTG from *Trypanosoma gondii*, Protozoan heat shock proteins, LeIF from *Leishmania* spp., profiling-like protein from *Toxoplasma gondii*.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein selected from adjuvant or immunostimulating proteins, human adjuvant proteins, bacterial (adjuvant) proteins, protozoan (adjuvant) proteins, viral (adjuvant) proteins, fungal (adjuvant) proteins, more preferably selected from viral (adjuvant) proteins, most preferably selected from Respiratory Syncytial Virus fusion glycoprotein (F-protein), envelope protein from MMT virus, mouse leukemia virus protein, Hemagglutinin protein of wild-type measles virus.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein selected from adjuvant or immunostimulating proteins, human adjuvant proteins, bacterial (adjuvant) proteins, protozoan (adjuvant) proteins, viral (adjuvant) proteins, fungal (adjuvant) proteins, more preferably selected from fungal (adjuvant) proteins, most preferably selected from fungal immunomodulatory protein (FIP; LZ-8); and Keyhole limpet hemocyanin (KLH), OspA.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism. Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic antibody selected from antibodies used for the treatment of cancer or tumour diseases, preferably 131I-tositumomab, 3F8, 8H9, Abagovomab, Adecatumumab, Afutuzumab, Alacizumab pegol, Alemtuzumab, Amatuximab, AME-133v, AMG 102, Anatumomab mafenatox, Apolizumab, Bavituximab, Bectumomab, Belimumab, Bevacizumab, Bivatuzumab mertansine, Blinatumomab, Brentuximab vedotin, Cantuzumab, Cantuzumab mertansine, Cantuzumab ravtansine, Capromab pendetide, Carlumab, Catumaxomab, Cetuximab, Citatuzumab bogatox, Cixutumumab, Clivatuzumab tetraxetan, CNTO 328, CNTO 95, Conatumumab, Dacetuzumab, Dalotuzumab, Denosumab, Detumomab, Drozitumab, Ecromeximab, Edrecolomab, Elotuzumab, Elsilimomab, Enavatuzumab, Ensituximab, Epratuzumab, Ertumaxomab, Ertumaxomab, Etaracizumab, Farletuzumab, FBTA05, Ficlatuzumab, Figitumumab, Flanvotumab, Galiximab, Galiximab, Ganitumab, GC1008, Gemtuzumab, Gemtuzumab ozogamicin, Girentuximab, Glembatumumab vedotin, GS6624, HuC242-DM4, HuHMFG1, HuN901-DM1, Ibritumomab, Icrucumab, ID09C3, Indatuximab ravtansine, Inotuzumab ozogamicin, Intetumumab, Ipilimumab, Iratumumab, Labetuzumab, Lexatumumab, Lintuzumab, Lorvotuzumab mertansine, Lucatumumab, Lumiliximab, Mapatumumab, Matuzumab, MDX-060, MEDI 522, Mitumomab, Mogamulizumab, MORab-003, MORab-009, Moxetumomab pasudotox, MT103, Nacolomab tafenatox, Naptumomab estafenatox, Narnatumab, Necitumumab, Nimotuzumab, Nimotuzumab, Olaratumab, Onartuzumab, Oportuzumab monatox, Oregovomab, Oregovomab, PAM4, Panitumumab, Patritumab, Pemtumomab, Pertuzumab, Pritumumab, Racotumomab, Radretumab, Ramucirumab, Rilotumumab, Rituximab, Robatumumab, Samalizumab, SGN-30, SGN-40, Sibrotuzumab, Siltuximab, Tabalumab, Tacatuzumab tetraxetan, Taplitumomab paptox, Tenatumomab, Teprotumumab, TGN1412, Ticilimumab (=tremelimumab), Tigatuzumab, TNX-650, Tositumomab, Trastuzumab, TRBS07, Tremelimumab, TRU-016, TRU-016, Tucotuzumab celmoleukin, Ublituximab, Urelumab, Veltuzumab, Veltuzumab (IMMU-106), Volociximab, Votumumab, WX-G250, Zalutumumab, and Zanolimumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic antibody selected from antibodies used for the treatment of immune disorders, preferably selected from Efalizumab, Epratuzumab, Etrolizumab, Fontolizumab, Ixekizumab, Mepolizumab, Milatuzumab, Pooled immunoglobulins, Priliximab, Rituximab, Rontalizumab, Ruplizumab, Sarilumab, Vedolizumab, Visilizumab, Reslizumab, Adalimumab, Aselizumab, Atinumab, Atlizumab, Bertilimumab, Besilesomab, BMS-945429, Briakinumab, Brodalumab, Canakinumab, Canakinumab, Certolizumab pegol, Erlizumab, Fezakinumab, Golimumab, Gomiliximab, Infliximab, Mavrilimumab, Natalizumab, Ocrelizumab, Odulimomab, Ofatumumab, Ozoralizumab, Pexelizumab, Rovelizumab, SBI-087, SBI-087, Secukinumab, Sirukumab, Talizumab, Tocilizumab, Toralizumab, TRU-015, TRU-016, Ustekinumab, Ustekinumab, Vepalimomab, Zolimomab aritox, Sifalimumab, Lumiliximab, and Rho(D) Immune Globulin.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic antibody selected from antibodies used for the treatment of cancer or tumour diseases, preferably antibodies used for the treatment of infectious diseases, particularly Afelimomab, CR6261, Edobacomab, Efungumab, Exbivirumab, Felvizumab, Foravirumab, Ibalizumab, Libivirumab, Motavizumab, Nebacumab, Tuvirumab, Urtoxazumab, Bavituximab, Pagibaximab, Palivizumab, Panobacumab, PRO 140, Rafivirumab, Raxibacumab, Regavirumab, Sevirumab, Suvizumab, and Tefibazumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic antibody selected from antibodies used for the treatment of cancer or tumour diseases, preferably antibodies used for the treatment of blood disorders, particularly Abciximab, Atorolimumab, Eculizumab, Mepolizumab, and Milatuzumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic antibody selected from antibodies used for the treatment of cancer or tumour diseases, preferably antibodies used for immunoregulation, particularly Antithymocyte globulin, Basiliximab, Cedelizumab, Daclizumab, Gavilimomab, Inolimomab, Muromonab-CD3, Muromonab-CD3, Odulimomab, and Siplizumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic antibody selected from antibodies used for the treatment of cancer or tumour diseases, preferably antibodies used for the treatment of diabetes, particularly Gevokizumab, Otelixizumab, and Teplizumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
  a) a coding region, encoding at least one peptide or protein;
  b) at least one histone stem-loop, and
  c) a poly(A) sequence or a polyadenylation signal;
  wherein said peptide or protein comprises a therapeutic protein or a fragment, variant or derivative thereof, preferably a therapeutic antibody selected from antibodies used for the treatment of cancer or tumour diseases, preferably antibodies used for the treatment of the Alzheimer's disease, particularly Bapineuzumab, Crenezumab, Gantenerumab, Ponezumab, R1450, and Solanezumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic antibody selected from antibodies used for the treatment of cancer or tumour diseases, preferably antibodies used for the treatment of asthma, particularly Benralizumab, Enokizumab, Keliximab, Lebrikizumab, Omalizumab, Oxelumab, Pascolizumab, and Tralokinumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic antibody selected from antibodies used for the treatment of cancer or tumour diseases, preferably antibodies for the treatment of diverse disorders, particularly Blosozumab, CaroRx, Fresolimumab, Fulranumab, Romosozumab, Stamulumab, Tanezumab, and Ranibizumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably, the invention provides a nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, may be a therapeutic protein
for use in the treatment of metabolic or endocrine disorders,
for use in the treatment of blood disorders, diseases of the circulatory system, diseases of the respiratory system, cancer or tumour diseases, infectious diseases or immunedeficiencies,
for use in hormone replacement therapy or
for use in reprogramming of somatic cells
more preferably a therapeutic protein selected from Acid sphingomyelinase, Adipotide, Agalsidase-beta, Alglucosidase, alpha-galactosidase A, alpha-glucosidase, alpha-L-iduronidase, alpha-N-acetylglucosaminidase, Amphiregulin, Angiopoietins (Ang1, Ang2, Ang3, Ang4, ANGPTL2, ANGPTL3, ANGPTL4, ANGPTL5, ANGPTL6, ANGPTL7), Betacellulin, Beta-glucuronidase, Bone morphogenetic proteins BMPs (BMP1, BMP2, BMP3, BMP4, BMP5, BMP6, BMP7, BMP8a, BMP8b, BMP10, BMP15), CLN6 protein, Epidermal growth factor (EGF), Epigen, Epiregulin, Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23), Galsulphase, Ghrelin, Glucocerebrosidase, GM-CSF, Heparin-binding EGF-like growth factor (HB-EGF), Hepatocyte growth factor HGF, Hepcidin, Human albumin, increased loss of albumin, Idursulphase (Iduronate-2-sulphatase), Integrins $\alpha V\beta 3$, $\alpha V\beta 5$ and $\alpha 5\beta 1$, Iuduronate sulfatase, Laronidase, N-acetylgalactosamine-4-sulfatase (rhASB; galsulfase, Arylsulfatase A (ARSA), Arylsulfatase B (ARSB)), N-acetylglucosamine-6-sulfatase, Nerve growth factor (NGF, Brain-Derived Neurotrophic Factor (BDNF), Neurotrophin-3 (NT-3), and Neurotrophin 4/5 (NT-4/5), Neuregulin (NRG1, NRG2, NRG3, NRG4), Neuropilin (NRP-1, NRP-2), Obestatin, Platelet Derived Growth factor (PDGF (PDFF-A, PDGF-B, PDGF-C, PDGF-D), TGF beta receptors (endoglin, TGF-beta 1 receptor, TGF-beta 2 receptor, TGF-beta 3 receptor), Thrombopoietin (THPO) (Megakaryocyte growth and development factor (MGDF)), Transforming Growth factor (TGF (TGF-a, TGF-beta (TGFbeta1, TGFbeta2, and TGF-beta3))), VEGF (VEGF-A, VEGF-B, VEGF-C, VEGF-D, VEGF-E, VEGF-F and PlGF), Nesiritide, Trypsin, adrenocorticotrophic hormone (ACTH), Atrial-natriuretic peptide (ANP), Cholecystokinin, Gastrin, Leptin, Oxytocin, Somatostatin, Vasopressin (antidiuretic hormone), Calcitonin, Exenatide, Growth hormone (GH), somatotropin, Insulin, Insulin-like growth factor 1 IGF-1, Mecasermin rinfabate, IGF-1 analog, Mecasermin, IGF-1 analog, Pegvisomant, Pramlintide, Teriparatide (human parathyroid hormone residues 1-34), Becaplermin, Dibotermin-alpha (Bone morphogenetic protein 2), Histrelin acetate (gonadotropin releasing hormone; GnRH), Octreotide, and Palifermin (keratinocyte growth factor; KGF), Alteplase (tissue plasminogen activator; tPA), Anistreplase, Antithrombin III (AT-III), Bivalirudin, Darbepoetin-alpha, Drotrecogin-alpha (activated protein C, Erythropoietin, Epoetin-alpha, erythropoetin, erthropoyetin, Factor IX, Factor VIIa, Factor VIII, Lepirudin, Protein C concentrate, Reteplase (deletion mutein of tPA), Streptokinase, Tenecteplase, Urokinase, Angiostatin, Anti-CD22 immunotoxin, Denileukin diftitox, Immunocyanin, MPS (Metallopanstimulin), Aflibercept, Endostatin, Collagenase, Human deoxy-ribonuclease I, dornase, Hyaluronidase, Papain, L-Asparaginase, Peg-asparaginase, Rasburicase, Human chorionic gonadotropin (HCG), Human follicle-stimulating hormone (FSH), Lutropin-alpha, Prolactin, alpha-1-Proteinase inhibitor, Lactase, Pancreatic enzymes (lipase, amylase, protease), Adenosine deaminase (pegademase bovine, PEG-ADA), Abatacept, Alefacept, Anakinra, Etanercept, Interleukin-1 (IL-1) receptor antagonist, Anakinra, Thymulin, TNF-alpha antagonist, Enfuvirtide, Thymosin a1, oestrogens, progesterone or progestins, testosterone, Oct-3/4, Sox gene family (Sox1, Sox2, Sox3, and Sox15), Klf family (Klf1, Klf2, Klf4, and Klf5), Myc family (c-myc, L-myc, and N-myc), Nanog, and LIN28.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
 a) a coding region, encoding at least one peptide or protein;
 b) at least one histone stem-loop, and
 c) a poly(A) sequence or a polyadenylation signal;
 wherein said peptide or protein comprises a therapeutic protein or a fragment, variant or derivative thereof, preferably a therapeutic protein selected from adjuvant or immunostimulating proteins, human adjuvant proteins, bacterial (adjuvant) proteins, protozoan (adjuvant) proteins, viral (adjuvant) proteins, fungal (adjuvant) proteins, more preferably selected from human adjuvant proteins, most preferably selected from pattern recognition receptors TLR1, TLR2, TLR3, TLR4, TLR5, TLR6, TLR7, TLR8, TLR9, TLR10, TLR11; NOD1, NOD2, NOD3, NOD4, NOD5, NALP1, NALP2, NALP3, NALP4, NALP5, NALP6, NALP6, NALP7, NALP7, NALP8, NALP9, NALP10, NALP11, NALP12, NALP13, NALP14, 1 IPAF, NAIP, CIITA, RIG-I, MDA5 and LGP2, the signal transducers of TLR signaling including adaptor proteins including e.g. Trif and Cardif; components of the Small-GTPases signalling (RhoA, Ras, Rac1, Cdc42, Rab etc.), components of the PIP signalling (PI3K, Src-Kinases, etc.), components of the MyD88-dependent signalling (MyD88, IRAK1, IRAK2, IRAK4, TIRAP, TRAF6 etc.), components of the MyD88-independent signalling (TICAM1, TICAM2, TRAF6, TBK1, IRF3, TAK1, IRAK1 etc.); the activated kinases including e.g. Akt, MEKK1, MKK1, MKK3, MKK4, MKK6, MKK7, ERK1, ERK2, GSK3, PKC kinases, PKD kinases, GSK3 kinases, JNK, p38MAPK, TAK1, IKK, and TAK1; the activated transcription factors including e.g. NF-κB, c-Fos, c-Jun, c-Myc, CREB, AP-1, Elk-1, ATF2, IRF-3, IRF-7, heat shock proteins, such as HSP10, HSP60, HSP65, HSP70, HSP75 and HSP90, gp96, Fibrinogen, TypIII repeat extra domain A of fibronectin; or components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4 bp, MCP, DAF, H, I, P and CD59, or induced target genes including e.g. Beta-Defensin, cell surface proteins; or human adjuvant proteins including trif, flt-3 ligand, Gp96 or fibronectin, cytokines which induce or enhance an innate immune response, including IL-1 alpha, IL1 beta, IL-2, IL-6, IL-7, IL-8, IL-9, IL-12, IL-13, IL-15, IL-16, IL-17, IL-18, IL-21, IL-23, TNFalpha, IFNalpha, IFNbeta, IFNgamma, GM-CSF, G-CSF, M-CSF; chemokines including IL-8, IP-10, MCP-1, MIP-1alpha, RANTES, Eotaxin, CCL21; cytokines which are released from macrophages, including IL-1, IL-6, IL-8, IL-12 and TNF-alpha; as well as IL-1R1 and IL-1 alpha, bacterial heat shock proteins or chaperons, including Hsp60, Hsp70, Hsp90, Hsp100; OmpA (Outer membrane protein) from gram-negative bacteria; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from pertussis toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori*; Surfactant protein D; Outer surface protein A lipoprotein from *Borrelia burgdorferi*, Ag38 (38 kDa antigen) from *Mycobacterium tuberculosis*; proteins from bacterial fimbriae; Enterotoxin CT of *Vibrio cholerae*, Pilin from pili from gram negative bacteria, and Surfactant protein A and bacterial flagellins, Tc52 from *Trypanosoma cruzi*, PFTG from *Trypanosoma gondii*, Protozoan heat shock proteins, LeIF from *Leishmania* spp., profiling-like protein from *Toxoplasma gondii*, Respiratory Syncytial Virus fusion glycoprotein (F-protein), envelope protein from MMT virus, mouse leukemia virus protein, Hemagglutinin protein of wild-type measles virus, fungal immunomodulatory protein (FIP; LZ-8); and Keyhole limpet hemocyanin (KLH), OspA.

Preferably the invention provides nucleic acid sequence comprising or coding for
 a) a coding region, encoding at least one peptide or protein;
 b) at least one histone stem-loop, and
 c) a poly(A) sequence or a polyadenylation signal;
 wherein said peptide or protein comprises a therapeutic protein or a fragment, variant or derivative thereof, preferably a therapeutic antibody selected from antibodies used for the treatment of cancer or tumour diseases, preferably 131I-tositumomab, 3F8, 8H9, Abagovomab, Adecatumumab, Afutuzumab, Alacizumab pegol, Alemtuzumab, Amatuximab, AME-133v, AMG 102, Anatumomab mafenatox, Apolizumab, Bavituximab, Bectumomab, Belimumab, Bevacizumab, Bivatuzumab mertansine, Blinatumomab, Brentuximab vedotin, Cantuzumab, Cantuzumab mertansine, Cantuzumab ravtansine, Capromab pendetide, Carlumab, Catumaxomab, Cetuximab, Citatuzumab bogatox, Cixutumumab, Clivatuzumab tetraxetan, CNTO 328, CNTO 95, Conatumumab, Dacetuzumab, Dalotuzumab, Denosumab, Detumomab, Drozitumab, Ecromeximab, Edrecolomab, Elotuzumab, Elsilimomab, Enavatuzumab, Ensituximab, Epratuzumab, Ertumaxomab, Ertumaxomab, Etaracizumab, Farletuzumab, FBTA05, Ficlatuzumab, Figitumumab, Flanvotumab, Galiximab, Galiximab, Ganitumab, GC1008, Gemtuzumab, Gemtuzumab ozogamicin, Girentuximab, Glembatumumab vedotin, GS6624, HuC242-DM4, HuHMFG1, HuN901-DM1, Ibritumomab, Icrucumab, ID09C3, Indatuximab ravtansine, Inotuzumab ozogamicin, Intetumumab, Ipilimumab, Iratumumab, Labetuzumab, Lexatumumab, Lintuzumab, Lorvotuzumab mertansine, Lucatumumab, Lumiliximab, Mapatumumab, Matuzumab, MDX-060, MEDI 522, Mitumomab, Mogamulizumab, MORab-003, MORab-009, Moxetumomab pasudotox, MT103, Nacolomab tafenatox, Naptumomab estafenatox, Narnatumab, Necitumumab, Nimotuzumab, Nimotuzumab, Olaratumab, Onartuzumab, Oportuzumab monatox, Oregovomab, Oregovomab, PAM4, Panitumumab, Patritumab, Pemtumomab, Pertuzumab, Pritumumab, Racotumomab, Radretumab, Ramucirumab, Rilotumumab, Rituximab, Robatumumab, Samalizumab, SGN-30, SGN-40, Sibrotuzumab, Siltuximab, Tabalumab, Tacatuzumab tetraxetan, Taplitumomab paptox, Tenatumomab, Teprotumumab, TGN1412, Ticilimumab, Tigatuzumab, TNX-650, Tositumomab, Trastuzumab, TRBS07, Tremelimumab, TRU-016, TRU-016, Tucotuzumab celmoleukin, Ublituximab, Urelumab, Veltuzumab, Veltuzumab (IMMU-106), Volociximab, Votumumab, WX-G250, Zalutumumab, Zanolimumab, Efalizumab, Epratuzumab, Etrolizumab, Fontolizumab, Ixekizumab, Mepolizumab, Milatuzumab, Pooled immunoglobulins, Priliximab, Rituximab, Rontalizumab, Ruplizumab, Sarilumab, Vedolizumab, Visilizumab, Reslizumab, Adalimumab, Aselizumab, Atinumab, Atlizumab, Bertilimumab, Besilesomab, BMS-945429, Briakinumab, Brodalumab, Canakinumab, Canakinumab, Certolizumab pegol, Erlizumab, Fezakinumab, Golimumab, Gomiliximab, Infliximab, Mavrilimumab, Natalizumab, Ocrelizumab, Odulimomab, Ofatumumab, Ozoralizumab, Pexelizumab, Rovelizumab, SBI-087, SBI-087, Secukinumab, Sirukumab, Talizumab, Tocilizumab, Toralizumab, TRU-015, TRU-016, Ustekinumab, Ustekinumab, Vepalimomab, Zolimomab aritox, Sifalimumab, Lumiliximab, and Rho(D) Immune Globulin, Afelimomab, CR6261, Edobacomab, Efungumab, Exbivirumab, Felvizumab, Foravirumab, Ibalizumab, Libivirumab, Motavizumab, Nebacumab, Tuvirumab, Urtoxazumab, Bavituximab, Pagibaximab, Palivizumab, Panobacumab, PRO 140, Rafivirumab, Raxibacumab, Regavirumab, Sevirumab, Suvizumab, Tefibazumab, Abciximab, Atorolimumab, Eculizumab, Mepolizumab, Milatuzumab, Antithymocyte globulin, Basiliximab, Cedelizumab, Daclizumab, Gavilimomab, Inolimomab, Muromonab-CD3, Muromonab-CD3, Odulimomab, Siplizumab, Gevokizumab, Otelixizumab, Teplizumab, Bapineuzumab, Crenezumab, Gantenerumab, Ponezumab, R1450, Solanezumab, Benralizumab, Enokizumab, Keliximab, Lebrikizumab, Omalizumab, Oxelumab, Pascolizumab, Tralokinumab, Blosozumab, CaroRx, Fresolimumab, Fulranumab, Romosozumab, Stamulumab, Tanezumab, and Ranibizumab.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein which is a protein hormone.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

Preferably the invention provides nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a therapeutic protein or a fragment, variant or derivative thereof, preferably a therapeutic protein which is a protein hormone.

The invention further provides the use of such a nucleic acid sequence in gene therapy as defined herein. The invention further provides a kit or kit of parts comprising such a nucleic acid sequence. Further, the invention provides a pharmaceutical composition comprising such a nucleic acid sequence. Further, the invention provides a method for increasing the expression fo an encoded peptide or protein comprising the steps of providing such a nucleic acid sequence or a composition containing such a nucleic acid sequence and applying or administering the nucleic acid sequence or othe composition to a cell-free expression system, a cell, a tissue or an organism.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

BRIEF DESCRIPTION OF THE FIGURES

The following Figures are intended to illustrate the invention further and shall not be construed to limit the present invention thereto.

FIG. 1: shows the histone stem-loop consensus sequence generated from metazoan and protozoan stem loop sequences (as reported by Dávila López, M., & Samuelsson, T. (2008), RNA (New York, N.Y.), 14(1), 1-10. doi:10.1261/rna.782308). 4001 histone stem-loop sequences from metazoa and protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 2: shows the histone stem-loop consensus sequence generated from protozoan stem loop sequences (as reported by Dávila López, M., & Samuelsson, T. (2008), *RNA* (New York, N.Y.), 14(1), 1-10. doi:10.1261/rna.782308). 131 histone stem-loop sequences from protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 4: shows the histone stem-loop consensus sequence generated from vertebrate stem loop sequences (as reported by Dávila López, M., & Samuelsson, T. (2008), *RNA* (New York, N.Y.), 14(1), 1-10. doi:10.1261/rna.782308). 1333 histone stem-loop sequences from vertebrates were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 5: shows the histone stem-loop consensus sequence generated from human (*Homo sapiens*) stem loop sequences (as reported by Dávila López, M., & Samuelsson, T. (2008), *RNA* (New York, N.Y.), 14(1), 1-10. doi:10.1261/rna.782308). 84 histone stem-loop sequences from humans were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIGS. 6 to 19: show mRNAs from in vitro transcription. Given are the designation and the sequence of mRNAs obtained by in vitro transcription. The following abbreviations are used:

Figure 3:
FIG. 3: shows the histone stem-loop consensus sequence generated from metazoan stem loop sequences (as reported by Dávila López, M., & Samuelsson, T. (2008), *RNA* (New York, N.Y.), 14(1), 1-10. doi:10.1261/rna.782308). 3870 histone stem-loop sequences from metazoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

| | |
|---|---|
| ppLuc (GC): | GC-enriched mRNA sequence coding for *Photinus pyralis* luciferase |
| ag: | 3' untranslated region (UTR) of the alpha globin gene |
| A64: | poly(A)-sequence with 64 adenylates |
| A120: | poly(A)-sequence with 120 adenylates |
| histoneSL: | histone stem-loop |
| aCPSL: | stem loop which has been selected from a library for its specific binding of the αCP-2KL protein |
| PolioCL: | 5' clover leaf from Polio virus genomic RNA |
| G30: | poly(G) sequence with 30 guanylates |
| U30: | poly(U) sequence with 30 uridylates |
| SL: | unspecific/artificial stem-loop |
| N32: | unspecific sequence of 32 nucleotides |
| MmEPO (GC): | GC-enriched mRNA sequence coding for murine EPO |

FIG. 6: shows the mRNA sequence of ppLuc(GC)-ag (SEQ ID NO: 43).
By linearization of the original vector at the restriction site immediately following the alpha-globin 3'-UTR (ag), mRNA is obtained lacking a poly(A) sequence.

FIG. 7: shows the mRNA sequence of ppLuc(GC)-ag-A64 (SEQ ID NO: 44).
By linearization of the original vector at the restriction site immediately following the A64 poly(A)-sequence, mRNA is obtained ending with an A64 poly(A) sequence.

FIG. 8: shows the mRNA sequence of ppLuc(GC)-ag-histoneSL (SEQ ID NO: 45).
The A64 poly(A) sequence was replaced by a histoneSL. The histone stem-loop sequence used in the examples was obtained from Cakmakci et al. (2008). *Molecular and Cellular Biology*, 28(3), 1182-1194.

FIG. 9: shows the mRNA sequence of ppLuc(GC)-ag-A64-histoneSL (SEQ ID NO: 46).
The histoneSL was appended 3' of A64 poly(A).

FIG. 10: shows the mRNA sequence of ppLuc(GC)-ag-A120 (SEQ ID NO: 47).
The A64 poly(A) sequence was replaced by an A120 poly(A) sequence.

FIG. 11: shows the mRNA sequence of ppLuc(GC)-ag-A64-ag (SEQ ID NO: 48). A second alpha-globin 3'-UTR was appended 3' of A64 poly(A).

FIG. 12: shows the mRNA sequence of ppLuc(GC)-ag-A64-aCPSL (SEQ ID NO: 49).
A stem loop was appended 3' of A64 poly(A). The stem loop has been selected from a library for its specific binding of the αCP-2KL protein (Thisted et al., (2001), The Journal of Biological Chemistry, 276(20), 17484-17496). αCP-2KL is an isoform of αCP-2, the most strongly expressed αCP protein (alpha-globin mRNA poly(C) binding protein) (Makeyev et al., (2000), Genomics, 67(3), 301-316), a group of RNA binding proteins, which bind to the alpha-globin 3'-UTR (Chkheidze et al., (1999), Molecular and Cellular Biology, 19(7), 4572-4581).

FIG. 13: shows the mRNA sequence of ppLuc(GC)-ag-A64-PolioCL (SEQ ID NO: 50).
The 5' clover leaf from Polio virus genomic *RNA* was appended 3' of A64 poly(A).

FIG. 14: shows the mRNA sequence of ppLuc(GC)-ag-A64-G30 (SEQ ID NO: 51)
A stretch of 30 guanylates was appended 3' of A64 poly(A).

FIG. 15: shows the mRNA sequence of ppLuc(GC)-ag-A64-U30 (SEQ ID NO: 52)
A stretch of 30 uridylates was appended 3' of A64 poly(A).

FIG. 16: shows the mRNA sequence of ppLuc(GC)-ag-A64-SL (SEQ ID NO: 53)
A stem loop was appended 3' of A64 poly(A). The upper part of the stem and the loop were taken from (Babendure et al., (2006), *RNA* (New York, N.Y.), 12(5), 851-861). The stem loop consists of a 17 base pair long, CG-rich stem and a 6 base long loop.

FIG. 17: shows ppLuc(GC)-ag-A64-N32 (SEQ ID NO: 54)

By linearization of the original vector at an alternative restriction site, mRNA is obtained with 32 additional nucleotides following poly(A).

FIG. 18: shows the mRNA sequence of MmEPO (GC)-ag-A64-C30 (SEQ ID NO: 55)

FIG. 19: shows the mRNA sequence of MmEPO (GC)-ag-A64-C30-histoneSL (SEQ ID NO: 56)

Figure 20:
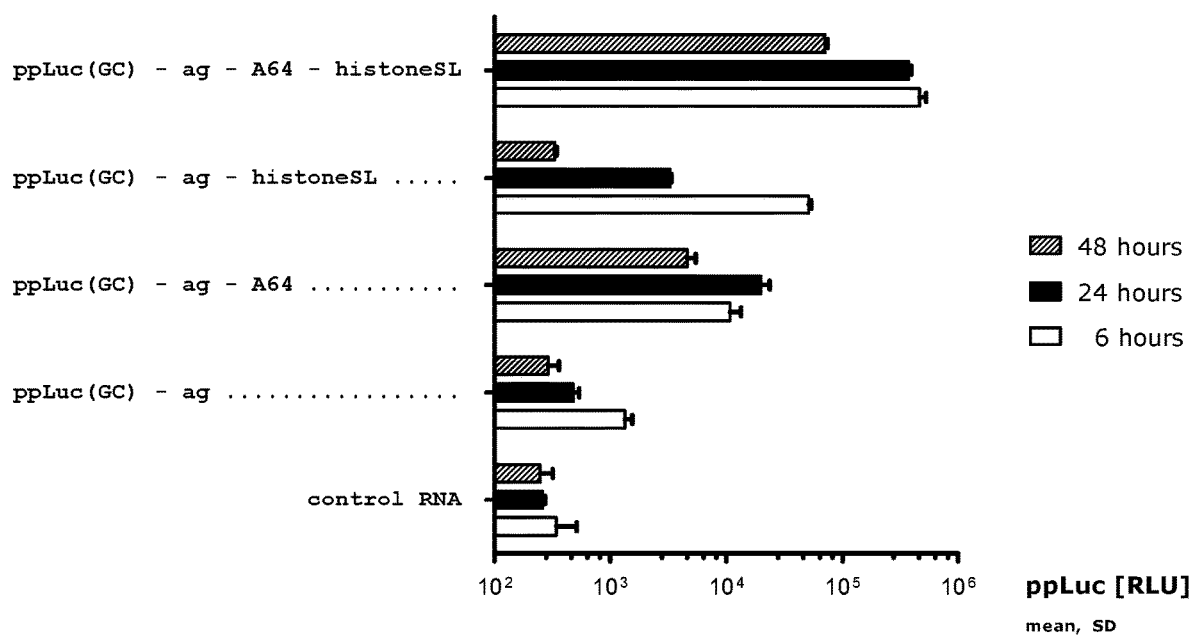

FIG. 20: shows that the combination of poly(A) and histoneSL increases protein expression from mRNA in a synergistic manner.

The effect of poly(A) sequence, histoneSL, and the combination of poly(A) and histoneSL on luciferase expression from mRNA was examined. Therefore different mRNAs were electroporated into HeLa cells. Luciferase levels were measured at 6, 24, and 48 hours after transfection. Little luciferase is expressed from mRNA having neither poly(A) sequence nor histoneSL. Both a poly(A) sequence or the histoneSL increase the luciferase level. Strikingly however, the combination of poly(A) and histoneSL further strongly increases the luciferase level, manifold above the level observed with either of the individual elements, thus acting synergistically. Data are graphed as mean RLU±SD (relative light units±standard deviation) for triplicate transfections. Specific RLU are summarized in Example 10.2.

Figure 21:
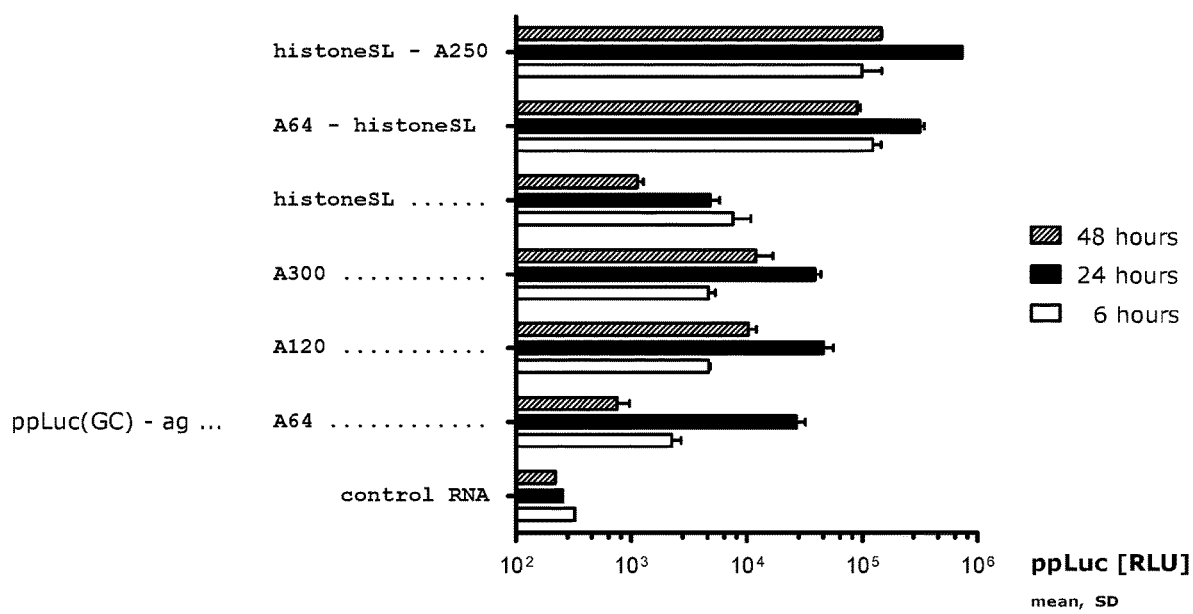

FIG. 21: shows that the combination of poly(A) and histoneSL increases protein expression from mRNA irrespective of their order.

The effect of poly(A) sequence, histoneSL, the combination of poly(A) and histoneSL, and their order on luciferase expression from mRNA was examined. Therefore different mRNAs were lipofected into HeLa cells. Luciferase levels were measured at 6, 24, and 48 hours after the start of transfection. Both an A64 poly(A) sequence or the histoneSL give rise to comparable luciferase levels. Increasing the length of the poly(A) sequence from A64 to A120 or to A300 increases the luciferase level moderately. In contrast, the combination of poly(A) and histoneSL increases the luciferase level much further than lengthening of the poly(A) sequence. The combination of poly(A) and histoneSL acts synergistically as it increases the luciferase level manifold above the level observed with either of the individual elements. The synergistic effect of the combination of poly(A) and histoneSL is seen irrespective of the order of poly(A) and histoneSL and irrespective of the length of poly(A) with A64-histoneSL or histoneSL-A250 mRNA. Data are graphed as mean RLU±SD for triplicate transfections. Specific RLU are summarized in Example 10.3.

Figure 22:
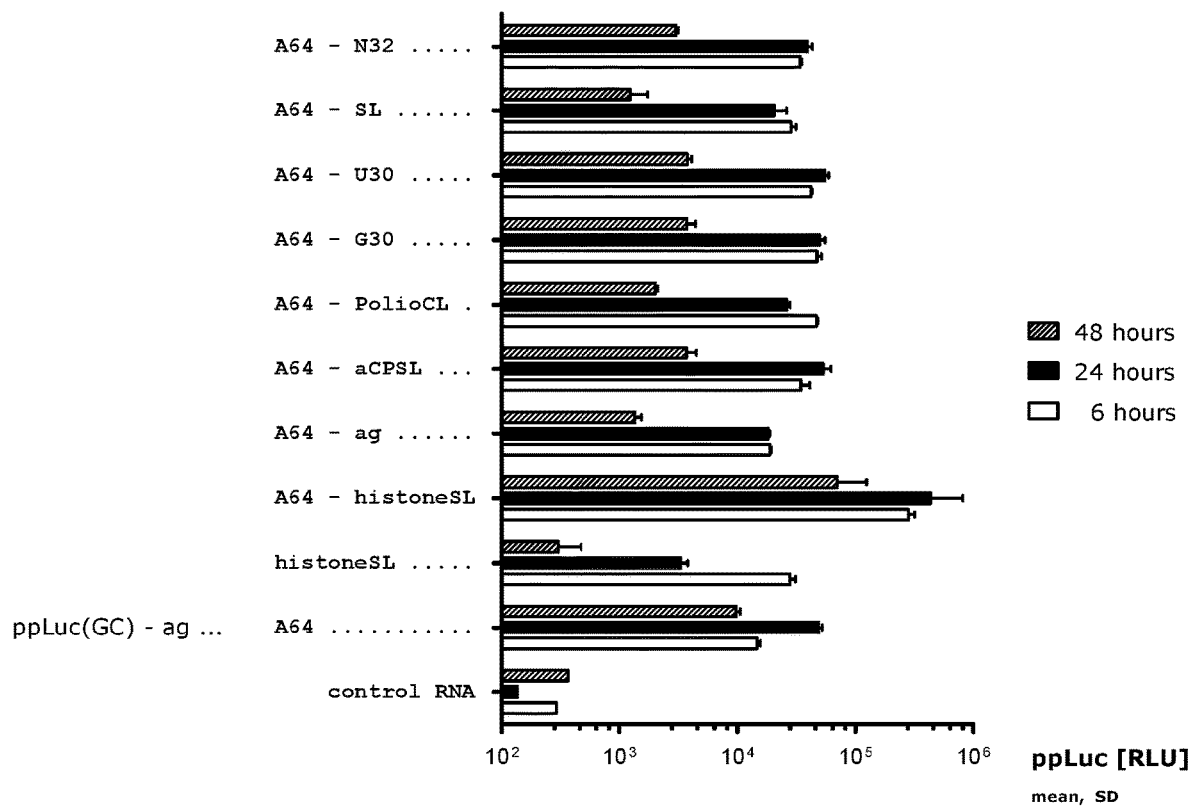

FIG. 22: shows that the rise in protein expression by the combination of poly(A) and histoneSL is specific.

The effect of combining poly(A) and histoneSL or poly(A) and alternative sequences on luciferase expression from mRNA was examined. Therefore different mRNAs were electroporated into HeLa cells. Luciferase levels were measured at 6, 24, and 48 hours after transfection. Both a poly(A) sequence or the histoneSL give rise to comparable luciferase levels. The combination of poly(A) and histoneSL strongly increases the luciferase level, manifold above the level observed with either of the individual elements, thus acting synergistically. In contrast, combining poly(A) with any of the other sequences is without effect on the luciferase level compared to mRNA containing only a poly(A) sequence. Thus, the combination of poly(A) and histoneSL acts specifically and synergistically. Data are graphed as mean RLU±SD for triplicate transfections. Specific RLU are summarized in Example 10.4.

Figure 23:
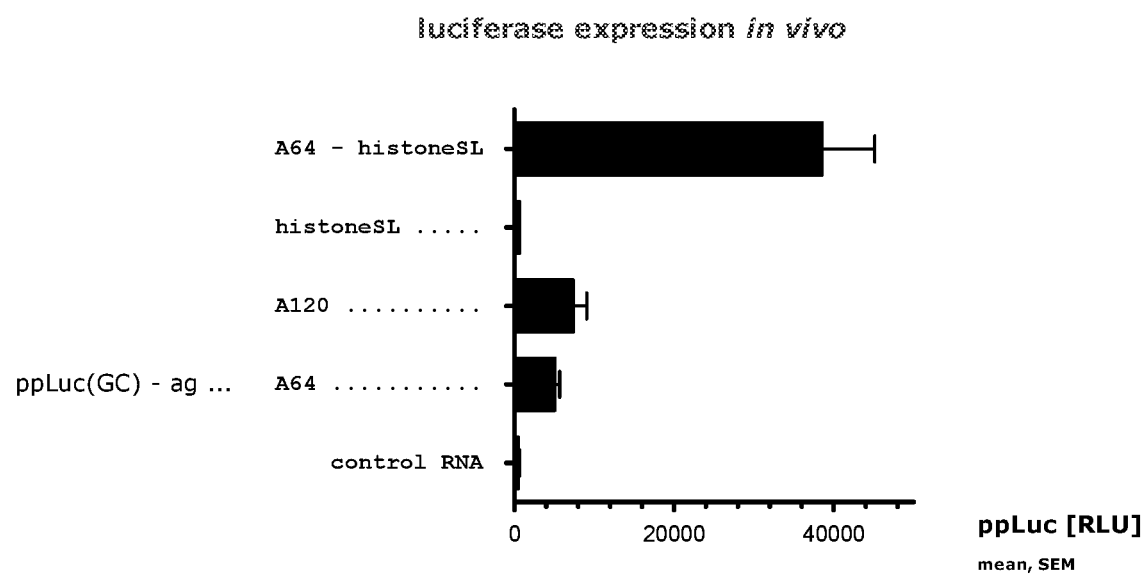

FIG. 23: shows that the combination of poly(A) and histoneSL increases protein expression from mRNA in a synergistic manner in vivo.

The effect of poly(A) sequence, histoneSL, and the combination of poly(A) and histoneSL on luciferase expression from mRNA in vivo was examined. Therefore different mRNAs were injected intradermally into mice. Mice were sacrificed 16 hours after injection and Luciferase levels at the injection sites were measured. Luciferase is expressed from mRNA having either a histoneSL or a poly(A) sequence. Strikingly however, the combination of poly(A) and histoneSL strongly increases the luciferase level, manifold above the level observed with either of the individual elements, thus acting synergistically. Data are graphed as mean RLU SEM (relative light units±standard error of mean). Specific RLU are summarized in Example 10.5.

FIG. 24: shows the mRNA sequence of Trastuzumab (GC)-ag-A64-C30 (SEQ ID NO: 57). This sequence encodes the antibody Trastuzumab (Herceptin) comprising the light and heavy chains as described in WO2008/083949.

FIG. 25: shows the mRNA sequence of Trastuzumab (GC)-ag-A64-C30-histoneSL (SEQ ID NO: 58). This sequence encodes the antibody Trastuzumab (Herceptin) comprising the light and heavy chains as described in WO2008/083949.

EXAMPLES

The following Examples are intended to illustrate the invention further and shall not be construed to limit the present invention thereto.

1. Generation of Histone-Stem-Loop Consensus Sequences

Prior to the experiments, histone stem-loop consensus sequences were determined on the basis of metazoan and protozoan histone stem-loop sequences. Sequences were taken from the supplement provided by Lopez et al. (Dávila López, M., & Samuelsson, T. (2008), RNA (New York, N.Y.), 14(1), 1-10. doi:10.1261/rna.782308), who identified a large number of natural histone stem-loop sequences by searching genomic sequences and expressed sequence tags. First, all sequences from metazoa and protozoa (4001 sequences), or all sequences from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. In addition, more restrictive consensus sequences were also obtained, increasingly emphasizing conserved nucleotides 2. Preparation of DNA-Templates A vector for in vitro transcription was constructed containing a T7 promoter followed by a GC-enriched sequence coding for *Photinus pyralis* luciferase (ppLuc (GC)), the center part of the 3' untranslated region (UTR) of alpha-globin (ag), and a poly(A) sequence. The poly(A) sequence was immediately followed by a restriction site used for linearization of the vector before in vitro transcription in order to obtain mRNA ending in an A64 poly(A) sequence. mRNA obtained from this vector accordingly by in vitro transcription is designated as "ppLuc(GC)-ag-A64".

Linearization of this vector at alternative restriction sites before in vitro transcription allowed to obtain mRNA either extended by additional nucleotides 3' of A64 or lacking A64. In addition, the original vector was modified to include alternative sequences. In summary, the following mRNAs were obtained from these vectors by in vitro transcription (mRNA sequences are given in FIGS. 6 to 17):

ppLuc(GC)-ag (SEQ ID NO: 43)

ppLuc(GC)-ag-A64 (SEQ ID NO: 44)

ppLuc(GC)-ag-histoneSL (SEQ ID NO: 45)

ppLuc(GC)-ag-A64-histoneSL (SEQ ID NO: 46)

ppLuc(GC)-ag-A120 (SEQ ID NO: 47)

ppLuc(GC)-ag-A64-ag (SEQ ID NO: 48)

ppLuc(GC)-ag-A64-aCPSL (SEQ ID NO: 49)

ppLuc(GC)-ag-A64-PolioCL (SEQ ID NO: 50)

ppLuc(GC)-ag-A64-G30 (SEQ ID NO: 51)

ppLuc(GC)-ag-A64-U30 (SEQ ID NO: 52)

ppLuc(GC)-ag-A64-SL (SEQ ID NO: 53)

ppLuc(GC)-ag-A64-N32 (SEQ ID NO: 54)

Furthermore DNA plasmid sequences coding for the therapeutic protein EPO was prepared accordingly as described above.

In summary, the following mRNAs were obtained from these vectors by in vitro transcription (mRNA sequences are given in FIGS. 18 to 19):

MmEPO(GC)-ag-A64-C30 (SEQ ID NO: 55)

MmEPO(GC)-ag-A64-C30-histoneSL (SEQ ID NO: 56)

Furthermore DNA plasmid sequences coding for the antibody Trastuzumab can be prepared accordingly as described above.

The following mRNAs are obtained from these vectors by in vitro transcription (mRNA sequences are given in FIGS. 24 and 25):

Trastuzumab(GC)-ag-A64-C30 (SEQ ID NO: 57)

Trastuzumab(GC)-ag-A64-C30-histoneSL (SEQ ID NO: 58)

3. In Vitro Transcription

The DNA-template according to Example 2 was linearized and transcribed in vitro using T7-Polymerase. The DNA-template was then digested by DNase-treatment. All mRNA-transcripts contained a 5'-CAP structure obtained by adding an excess of N7-Methyl-Guanosine-5'-Triphosphate-5'-Guanosine to the transcription reaction. mRNA thus obtained was purified and resuspended in water.

4. Enzymatic Adenylation of mRNA

Two mRNAs were enzymatically adenylated: ppLuc(GC)-ag-A64 and ppLuc(GC)-ag-histoneSL.

To this end, RNA was incubated with *E. coli* Poly(A)-polymerase and ATP (Poly(A) Polymerase Tailing Kit, Epicentre, Madison, USA) following the manufacturer's instructions. mRNA with extended poly(A) sequence was purified and resuspended in water. The length of the poly(A) sequence was determined via agarose gel electrophoresis. Starting mRNAs were extended by approximately 250 adenylates, the mRNAs obtained are designated as ppLuc(GC)-ag-A300 and ppLuc(GC)-ag-histoneSL-A250, respectively.

5. Luciferase Expression by mRNA Electroporation

HeLa cells were trypsinized and washed in OPTI-MEM®. $1 \times 10^5$ cells in 200 µl of opti-MEM each were electroporated with 0.5 µg of ppLuc-encoding mRNA. As a control, mRNA not coding for ppLuc was electroporated separately. Electroporated cells were seeded in 24-well plates in 1 ml of RPMI 1640 medium. 6, 24, or 48 hours after transfection, medium was aspirated and cells were lysed in 200 µl of lysis buffer (25 mM Tris, pH 7.5 (HCl), 2 mM EDTA, 10% glycerol, 1% Triton X-100, 2 mM DTT, 1 mM PMSF). Lysates were stored at −20° C. until ppLuc activity was measured.

6. Luciferase Expression by mRNA Lipofection

HeLa cells were seeded in 96 well plates at a density of $2 \times 10^4$ cells per well. The following day, cells were washed in OPTI-MEM® and then transfected with 0.25 µg of Lipofectin-complexed ppLuc-encoding mRNA in 150 µl of OPTI-MEM®. As a control, mRNA not coding for ppLuc was lipofected separately. In some wells, OPTI-MEM® was aspirated and cells were lysed in 200 µl of lysis buffer 6 hours after the start of transfection. In the remaining wells, OPTI-MEM® was exchanged for RPMI 1640 medium at that time. In these wells, medium was aspirated and cells were lysed in 200 µl of lysis buffer 24 or 48 hours after the start of transfection. Lysates were stored at −20° C. until ppLuc activity was measured.

7. Luciferase Measurement ppLuc activity was measured as relative light units (RLU) in a BioTek SYNERGY™HT plate reader at 5 seconds measuring time using 50 µl of lysate and 200 µl of luciferin buffer (25 mM Glycylglycin, pH 7.8 (NaOH), 15 mM MgSO$_4$, 2 mM ATP, 75 µM luciferin). Specific RLU were calculated by subtracting RLU of the control RNA from total RLU.

8. Luciferase Expression by Intradermal mRNA Injection (Luciferase Expression In Vivo)

Mice were anaesthetized with a mixture of ROMPUN™ and KETAVET™. Each ppLuc-encoding mRNA was injected intradermally (0.5 µg of mRNA in 50 µl per injection). As a control, mRNA not coding for ppLuc was injected separately. 16 hours after injection, mice were sacrificed and tissue collected. Tissue samples were flash frozen in liquid nitrogen and lysed in a tissue lyser (Qiagen) in 800 µl of lysis buffer (25 mM Tris, pH 7.5 (HCl), 2 mM EDTA, 10% glycerol, 1% Triton X-100, 2 mM DTT, 1 mM PMSF). Subsequently samples were centrifuged at 13500 rpm at 4° C. for 10 minutes. Lysates were stored at −80° C. until ppLuc activity was measured (see 7. luciferase measurement).

9. MmEPO Expression in HeLa Cells

HeLa cells are trypsinized and washed in OPTI-MEM®. 1×10$^5$ cells in 200 µl of OPTI-MEM® each are electroporated with 0.5 µg of MmEPO-encoding mRNA. As a control, irrelevant mRNA is electroporated separately. Electroporated cells are seeded in 24-well plates in 1 ml of RPMI 1640 medium. 6, 24, or 48 hours after transfection, supernatants are taken and harvested from the cells. The content of EPO in the supernatants is measured with the Mouse/Rat Erythropoietin QUANTIKINE® ELISA Kit (R&D Systems) according to the manufacturer's instructions.

10. Results 10.1 Histone Stem-Loop Sequences:

In order to characterize histone stem-loop sequences, sequences from metazoa and protozoa (4001 sequences), or from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. Within the consensus sequence of metazoa and protozoa combined, 3 nucleotides are conserved, a T/U in the loop and a G and a C in the stem, forming a base pair. Structurally, typically a 6 base-pair stem and a loop of 4 nucleotides is formed. However, deviating structures are common: Of 84 human histone stem-loops, two contain a stem of only 5 nucleotides comprising 4 base-pairs and one mismatch. Another human histone stem-loop contains a stem of only 5 base-pairs. Four more human histone stem-loops contain a 6 nucleotide long stem, but include one mismatch at three different positions, respectively. Furthermore, four human histone stem-loops contain one wobble base-pair at two different positions, respectively. Concerning the loop, a length of 4 nucleotides seems not to be strictly required, as a loop of 5 nucleotides has been identified in D. discoideum.

In addition to the consensus sequences representing all nucleotides present in the sequences analyzed, more restrictive consensus sequences were also obtained, increasingly emphasizing conserved nucleotides. In summary, the following sequences were obtained:

(Cons): represents all nucleotides present
(99%): represents at least 99% of all nucleotides present
(95%): represents at least 95% of all nucleotides present
(90%): represents at least 90% of all nucleotides present The results of the analysis of histone stem-loop sequences are summarized in the following Tables 1 to 5 (see also FIGS. 1 to 5):

TABLE 1

Metzoan and protozoan histone stem-loop consensus sequence: (based on an alignment of 4001 metazoan and protozoan histone stem-loop sequences) (see also FIG. 1)

|   |   |   |   |   |   | < | < | < | < | < | < | • | • |
|---|---|---|---|---|---|---|---|---|---|---|---|---|---|
| # A | 2224 | 1586 | 3075 | 2872 | 1284 | 184 | 0 | 13 | 12 | 9 | 1 | 47 | 59 |
| # T | 172 | 188 | 47 | 205 | 19 | 6 | 0 | 569 | 1620 | 199 | 3947 | 3830 | 3704 |
| # C | 1557 | 2211 | 875 | 918 | 2675 | 270 | 0 | 3394 | 2342 | 3783 | 51 | 119 | 227 |
| # G | 25 | 16 | 4 | 6 | 23 | 3541 | 4001 | 25 | 27 | 10 | 2 | 5 | 11 |
| Cons | N* | N* | N | N | N | N | G | N | N | N | N | N | N |
| 99% | H* | H* | H | H | V | V | G | Y | Y | Y | Y | H | H |
| 95% | M* | M* | M | H | M | S | G | Y | Y | Y | T | T | Y |
| 90% | M* | M* | M | M | M | S | G | Y | Y | C | T | T | T |

|   | • | • | > | > | > | > | > | > |   |   |   |   |   |
|---|---|---|---|---|---|---|---|---|---|---|---|---|---|
| # A | 0 | 675 | 3818 | 195 | 1596 | 523 | 0 | 14 | 3727 | 61 | 771 | 2012 | 2499 |
| # T | 4001 | 182 | 1 | 21 | 15 | 11 | 0 | 179 | 8 | 64 | 557 | 201 | 690 |
| # C | 0 | 3140 | 7 | 50 | 31 | 16 | 4001 | 3543 | 154 | 3870 | 2636 | 1744 | 674 |
| # G | 0 | 4 | 175 | 3735 | 2359 | 3451 | 0 | 265 | 112 | 4 | 37 | 43 | 138 |
| Cons | T | N | N | N | N | N | C | N | N | N | N* | N* | N* |
| 99% | T | H | R | V | V | R | C | B | V | H | H* | N* | N* |
| 95% | T | M | A | R | R | R | C | S | M | C | H* | H* | H* |
| 90% | T | M | A | G | R | R | C | S | A | C | H* | M* | H* |

TABLE 2

Protozoan histone stem-loop consensus sequence: (based on an alignment of 131 protozoan histone stem-loop sequences) (see also FIG. 2)

|   |   |   |   |   |   | < | < | < | < | < | • | • | • | • | • | > | > | > | > | > | > |
|---|---|---|---|---|---|---|---|---|---|---|---|---|---|---|---|---|---|---|---|---|---|
| # A | 52 | 32 | 71 | 82 | 76 | 13 | 0 | 12 | 12 | 9 | 1 | 46 | 3 | 0 | 75 | 82 | 53 | 79 | 20 | 0 | 4 | 94 | 17 | 35 | 74 | 56 |
| # T | 20 | 32 | 37 | 21 | 8 | 3 | 0 | 21 | 85 | 58 | 86 | 70 | 65 | 131 | 28 | 1 | 17 | 13 | 10 | 0 | 15 | 7 | 31 | 32 | 20 | 28 |
| # C | 45 | 59 | 20 | 25 | 38 | 0 | 0 | 86 | 8 | 54 | 42 | 13 | 58 | 0 | 27 | 2 | 6 | 31 | 10 | 131 | 112 | 5 | 82 | 58 | 30 | 40 |

TABLE 2-continued

Protozoan histone stem-loop consensus sequence: (based on an alignment of 131 protozoan histone stem-loop sequences) (see also FIG. 2)

|  | < | < | < | < | < | < | • | • | • | • | • | > | > | > | > | > | > |  |  |  |  |  |  |
|---|---|---|---|---|---|---|---|---|---|---|---|---|---|---|---|---|---|---|---|---|---|---|---|
| # G | 14 | 8 | 3 | 3 | 9 | 115 | 131 | 12 | 26 | 10 | 2 | 2 | 5 | 0 | 1 | 46 | 55 | 8 | 91 | 0 | 0 | 25 | 1 | 6 | 7 | 7 |
| Cons | N* | N* | N | N | N | D | G | N | N | N | N | N | N | T | N | N | N | N | N | C | H | N | N | N* | N* | N* |
| 99% | N* | N* | N | N | N | D | G | N | N | N | B | N | N | T | H | V | N | N | N | C | H | N | H | N* | N* | N* |
| 95% | N* | N* | H | H | N | R | G | N | N | N | Y | H | B | T | H | R | D | N | N | C | Y | D | H | H* | N* | N* |
| 90% | N* | H* | H | H | V | R | G | N | D | B | Y | H | Y | T | H | R | D | H | N | C | Y | R | H | H* | H* | H* |

TABLE 3

Metazoan histone stem-loop consensus sequence: (based on an alignment of 3870 (including 1333 vertebrate sequences) metazoan histone stem-loop sequences) (see also FIG. 3)

|  | < | < | < | < | < | < | • | • |
|---|---|---|---|---|---|---|---|---|
| # A | 2172 | 1554 | 3004 | 2790 | 1208 | 171 | 0 | 1 | 0 | 0 | 0 | 1 | 56 |
| # T | 152 | 156 | 10 | 184 | 11 | 3 | 0 | 548 | 1535 | 141 | 3861 | 3760 | 3639 |
| # C | 1512 | 2152 | 855 | 893 | 2637 | 270 | 0 | 3308 | 2334 | 3729 | 9 | 106 | 169 |
| # G | 11 | 8 | 1 | 3 | 14 | 3426 | 3870 | 13 | 1 | 0 | 0 | 3 | 6 |
| Cons | N* | N* | N | N | N | N | G | N | B | Y | Y | N | N |
| 99% | H* | H* | M | H | M | V | G | Y | Y | Y | T | Y | H |
| 95% | M* | M* | M | M | M | S | G | Y | Y | C | T | T | Y |
| 90% | M* | M* | M | M | M | S | G | Y | Y | C | T | T | T |

|  | • | • | > | > | > | > | > | > |
|---|---|---|---|---|---|---|---|---|
| # A | 0 | 600 | 3736 | 142 | 1517 | 503 | 0 | 10 | 3633 | 44 | 736 | 1938 | 2443 |
| # T | 3870 | 154 | 0 | 4 | 2 | 1 | 0 | 164 | 1 | 33 | 525 | 181 | 662 |
| # C | 0 | 3113 | 5 | 44 | 0 | 6 | 3870 | 3431 | 149 | 3788 | 2578 | 1714 | 634 |
| # G | 0 | 3 | 129 | 3680 | 2351 | 3360 | 0 | 265 | 87 | 3 | 31 | 36 | 131 |
| Cons | T | N | V | N | D | N | C | N | N | N | N* | N* | N* |
| 99% | T | H | R | V | R | R | C | B | V | M | H* | H* | N* |
| 95% | T | M | A | G | R | R | C | S | M | C | H* | H* | H* |
| 90% | T | M | A | G | R | R | C | S | A | C | H* | M* | H* |

TABLE 4

Vertebrate historic stem-loop consensus sequence: (based on an alignment of 1333 vertebrate histone stem-loop sequences) (see also FIG. 4)

|  | < | < | < | < | < | < | • | • |
|---|---|---|---|---|---|---|---|---|
| # A | 661 | 146 | 1315 | 1323 | 920 | 8 | 0 | 1 | 0 | 0 | 0 | 1 | 4 |
| # T | 63 | 121 | 2 | 2 | 6 | 2 | 0 | 39 | 1217 | 2 | 1331 | 1329 | 1207 |
| # C | 601 | 1062 | 16 | 6 | 403 | 1 | 0 | 1293 | 116 | 1331 | 2 | 0 | 121 |
| # G | 8 | 4 | 0 | 2 | 4 | 1322 | 1333 | 0 | 0 | 0 | 0 | 3 | 1 |
| Cons | N* | N* | H | N | N | N | G | H | Y | Y | Y | D | N |
| 99% | H* | H* | M | A | M | G | G | Y | Y | C | T | T | Y |
| 95% | H* | H* | A | A | M | G | G | C | Y | C | T | T | Y |
| 90% | M* | M* | A | A | M | G | G | C | T | C | T | T | T |

|  | • | • | > | > | > | > | > | > |
|---|---|---|---|---|---|---|---|---|
| # A | 0 | 441 | 1333 | 0 | 1199 | 21 | 0 | 1 | 1126 | 26 | 81 | 380 | 960 |
| # T | 1333 | 30 | 0 | 1 | 0 | 1 | 0 | 2 | 1 | 22 | 91 | 91 | 12 |
| # C | 0 | 862 | 0 | 2 | 0 | 0 | 1333 | 1328 | 128 | 1284 | 1143 | 834 | 361 |
| # G | 0 | 0 | 0 | 1330 | 134 | 1311 | 0 | 2 | 78 | 1 | 18 | 28 | 0 |
| Cons | T | H | A | B | R | D | C | N | N | N | N* | N* | H* |
| 99% | T | H | A | G | R | R | C | C | V | H | N* | N* | M* |
| 95% | T | M | A | G | R | G | C | C | V | C | H* | H* | M* |
| 90% | T | M | A | G | R | G | C | C | M | C | Y* | M* | M* |

TABLE 5

*Homo sapiens* histone stem-loop consensus sequence: (based on an alignment of 84 human histone stem-loop sequences) (see also FIG. 5)

|  | < | < | < | < | < | < | • | • | • | • | > | > | > | > | > | > |
|---|---|---|---|---|---|---|---|---|---|---|---|---|---|---|---|---|
| # A | 10 | 17 | 84 | 84 | 76 | 1 | 0 | 1 | 0 | 0 | 0 | 1 | 0 | 0 | 12 | 84 | 0 | 65 | 3 | 0 | 0 | 69 | 5 | 0 | 10 | 64 |
| # T | 8 | 6 | 0 | 0 | 2 | 2 | 0 | 1 | 67 | 0 | 84 | 80 | 81 | 84 | 5 | 0 | 0 | 0 | 0 | 0 | 0 | 4 | 25 | 24 | 3 |

TABLE 5-continued

Homo sapiens histone stem-loop consensus sequence: (based on an alignment of 84 human histone stem-loop sequences) (see also FIG. 5)

|  |  | < | < | < | < | < | < | • | • | • | • | > | > | > | > | > | > |  |  |  |  |  |  |
|---|---|---|---|---|---|---|---|---|---|---|---|---|---|---|---|---|---|---|---|---|---|---|---|
| # C | 62 | 61 | 0 | 0 | 6 | 0 | 0 | 82 | 17 | 84 | 0 | 0 | 3 | 0 | 67 | 0 | 1 | 0 | 0 | 84 | 84 | 5 | 75 | 57 | 44 | 17 |
| # G | 4 | 0 | 0 | 0 | 0 | 81 | 84 | 0 | 0 | 0 | 0 | 3 | 0 | 0 | 0 | 0 | 83 | 19 | 81 | 0 | 0 | 10 | 0 | 2 | 6 | 0 |
| Cons | N* | H* | A | A | H | D | G | H | Y | C | T | D | Y | T | H | A | S | R | R | C | C | V | H | B* | N* | H* |
| 99% | N* | H* | A | A | H | D | G | H | Y | C | T | D | Y | T | H | A | S | R | R | C | C | V | H | B* | N* | H* |
| 95% | H* | H* | A | A | M | G | G | C | Y | C | T | T | T | T | H | A | G | R | G | C | C | V | M | Y* | N* | M* |
| 90% | H* | M* | A | A | A | G | G | C | Y | C | T | T | T | T | M | A | G | R | G | C | C | R | M | Y* | H* | M* |

Wherein the used abbreviations were defined as followed:

| abbreviation | Nucleotide bases | remark |
|---|---|---|
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | present or not | Base may be present or not |

10.2 the Combination of Poly(A) and histoneSL Increases Protein Expression from mRNA in a Synergistic Manner.

To investigate the effect of the combination of poly(A) and histoneSL on protein expression from mRNA, mRNAs with different sequences 3' of the alpha-globin 3'-UTR were synthesized: mRNAs either ended just 3' of the 3'-UTR, thus lacking both poly(A) sequence and histoneSL, or contained either an A64 poly(A) sequence or a histoneSL instead, or both A64 poly(A) and histoneSL 3' of the 3'-UTR. Luciferase-encoding mRNAs or control mRNA were electroporated into HeLa cells. Luciferase levels were measured at 6, 24, and 48 hours after transfection (see following Table 6 and FIG. 20).

TABLE 6

| mRNA | RLU at 6 hours | RLU at 24 hours | RLU at 48 hours |
|---|---|---|---|
| ppLuc(GC)-ag-A64-histoneSL | 466553 | 375169 | 70735 |
| ppLuc(GC)-ag-histoneSL | 50947 | 3022 | 84 |
| ppLuc(GC)-ag-A64 | 10471 | 19529 | 4364 |
| ppLuc(GC)-ag | 997 | 217 | 42 |

Little luciferase was expressed from mRNA having neither poly(A) sequence nor histoneSL. Both a poly(A) sequence or the histoneSL increased the luciferase level to a similar extent. Either mRNA gave rise to a luciferase level much higher than did mRNA lacking both poly(A) and histoneSL. Strikingly however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 7).

TABLE 7

|  | A64 | histoneSL | RLU at 6 hours | RLU at 24 hours | RLU at 48 hours |
|---|---|---|---|---|---|
|  | + | + | 466553 | 375169 | 70735 |
|  | − | + | 50947 | 3022 | 84 |
|  | + | − | 10471 | 19529 | 4364 |
| Synergy |  |  | 7.6 | 16.6 | 15.9 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was up to 16.6 times higher than if their effects were purely additive. This result confirms that the combination of poly(A) and histoneSL effects a markedly synergistic increase in protein expression.

10.3 the Combination of Poly(A) and histoneSL Increases Protein Expression from mRNA Irrespective of their Order.

The effect of the combination of poly(A) and histoneSL might depend on the length of the poly(A) sequence and the order of poly(A) and histoneSL. Thus, mRNAs with increasing poly(A) sequence length and mRNA with poly(A) and histoneSL in reversed order were synthesized: Two mRNAs contained 3' of the 3'-UTR either an A120 or an A300 poly(A) sequence. One further mRNA contained 3' of the 3'-UTR first a histoneSL followed by an A250 poly(A) sequence. Luciferase-encoding mRNAs or control mRNA were lipofected into HeLa cells. Luciferase levels were measured at 6, 24, and 48 hours after the start of transfection (see following Table 8 and FIG. 21).

TABLE 8

| mRNA | RLU at 6 hours | RLU at 24 hours | RLU at 48 hours |
|---|---|---|---|
| ppLuc(GC)-ag-histoneSL-A250 | 98472 | 734222 | 146479 |
| ppLuc(GC)-ag-A64-histoneSL | 123674 | 317343 | 89579 |
| ppLuc(GC)-ag-histoneSL | 7291 | 4565 | 916 |
| ppLuc(GC)-ag-A300 | 4357 | 38560 | 11829 |
| ppLuc(GC)-ag-A120 | 4371 | 45929 | 10142 |
| ppLuc(GC)-ag-A64 | 1928 | 26781 | 537 |

Both an A64 poly(A) sequence or the histoneSL gave rise to comparable luciferase levels. In agreement with the previous experiment did the combination of A64 and histoneSL strongly increase the luciferase level, manifold above the level observed with either of the individual elements. The magnitude of the rise in luciferase level due to combining poly(A) and histoneSL in the same mRNA demonstrates that they are acting synergistically. The synergy between A64 and histoneSL was quantified as before based on the luciferase levels of A64-histoneSL, A64, and histoneSL mRNA (see following Table 9). The luciferase level from mRNA combining A64 and histoneSL was up to 61.7 times higher than if the effects of poly(A) and histoneSL were purely additive.

TABLE 9

|  | A64 | histoneSL | RLU at 6 hours | RLU at 24 hours | RLU at 48 hours |
|---|---|---|---|---|---|
|  | + | + | 123674 | 317343 | 89579 |
|  | − | + | 7291 | 4565 | 916 |
|  | + | − | 1928 | 26781 | 537 |
| Synergy |  |  | 13.4 | 10.1 | 61.7 |

In contrast, increasing the length of the poly(A) sequence from A64 to A120 or to A300 increased the luciferase level only moderately (see Table 8 and FIG. 19). mRNA with the longest poly(A) sequence, A300, was also compared to mRNA in which a poly(A) sequence of similar length was combined with the histoneSL, histoneSL-A250. In addition to having a long poly(A) sequence, the order of histoneSL and poly(A) is reversed in this mRNA relative to A64-histoneSL mRNA. The combination of A250 and histoneSL strongly increased the luciferase level, manifold above the level observed with either histoneSL or A300. Again, the synergy between A250 and histoneSL was quantified as before comparing RLU from histoneSL-A250 mRNA to RLU from A300 mRNA plus histoneSL mRNA (see following Table 10). The luciferase level from mRNA combining A250 and histoneSL was up to 17.0 times higher than if the effects of poly(A) and histoneSL were purely additive.

TABLE 10

|  | histoneSL | A250/A300 | RLU at 6 hours | RLU at 24 hours | RLU at 48 hours |
|---|---|---|---|---|---|
|  | + | + | 98472 | 734222 | 146479 |
|  | + | − | 7291 | 4565 | 916 |
|  | − | + | 4357 | 38560 | 11829 |
| Synergy |  |  | 8.5 | 17.0 | 11.5 |

In summary, a highly synergistic effect of the combination of histoneSL and poly(A) on protein expression from mRNA has been demonstrated for substantially different lengths of poly(A) and irrespective of the order of poly(A) and histoneSL.

10.4 the Rise in Protein Expression by the Combination of Poly(A) and histoneSL is Specific To investigate whether the effect of the combination of poly(A) and histoneSL on protein expression from mRNA is specific, mRNAs with alternative sequences in combination with poly(A) were synthesized: These mRNAs contained 3' of A64 one of seven distinct sequences, respectively. Luciferase-encoding mRNAs or control mRNA were electroporated into HeLa cells. Luciferase levels were measured at 6, 24, and 48 hours after transfection (see following Table 11 and FIG. 22).

TABLE 11

| mRNA | RLU at 6 hours | RLU at 24 hours | RLU at 48 hours |
|---|---|---|---|
| ppLuc(GC)-ag-A64-N32 | 33501 | 38979 | 2641 |
| ppLuc(GC)-ag-A64-SL | 28176 | 20364 | 874 |
| ppLuc(GC)-ag-A64-U30 | 41632 | 54676 | 3408 |
| ppLuc(GC)-ag-A64-G30 | 46763 | 49210 | 3382 |
| ppLuc(GC)-ag-A64-PolioCL | 46428 | 26090 | 1655 |
| ppLuc(GC)-ag-A64-aCPSL | 34176 | 53090 | 3338 |
| ppLuc(GC)-ag-A64-ag | 18534 | 18194 | 989 |
| ppLuc(GC)-ag-A64-histoneSL | 282677 | 437543 | 69292 |
| ppLuc(GC)-ag-histoneSL | 27597 | 3171 | 0 |
| ppLuc(GC)-ag-A64 | 14339 | 48414 | 9357 |

Both a poly(A) sequence or the histoneSL gave rise to comparable luciferase levels. Again, the combination of poly(A) and histoneSL strongly increased the luciferase level, manifold above the level observed with either of the individual elements, thus acting synergistically. In contrast, combining poly(A) with any of the alternative sequences was without effect on the luciferase level compared to mRNA containing only a poly(A) sequence. Thus, the combination of poly(A) and histoneSL increases protein expression from mRNA in a synergistic manner, and this effect is specific.

10.5 the Combination of Poly(A) and histoneSL Increases Protein Expression from mRNA in a Synergistic Manner In Vivo.

To investigate the effect of the combination of poly(A) and histoneSL on protein expression from mRNA in vivo, Luciferase-encoding mRNAs with different sequences 3' of the alpha-globin 3'-UTR or control mRNA were injected intradermally into mice: mRNAs contained either an A64 poly(A) sequence or a histoneSL instead, or both A64 poly(A) and histoneSL 3' of the 3'-UTR. Luciferase levels were measured at 16 hours after injection (see following Table 12 and FIG. 23).

TABLE 12

| mRNA | RLU at 16 hours |
|---|---|
| ppLuc(GC)-ag-A64-histoneSL | 38081 |
| ppLuc(GC)-ag-histoneSL | 137 |
| ppLuc(GC)-ag-A64 | 4607 |

Luciferase was expressed from mRNA having either a histoneSL or a poly(A) sequence. Strikingly, however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 13).

TABLE 13

| | A64 | histoneSL | RLU at 16 hours |
|---|---|---|---|
| | + | + | 38081 |
| | − | + | 137 |
| | + | − | 4607 |
| Synergy | | | 8.0 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was 8 times higher than if their effects were purely additive. This result confirms that the combination of poly(A) and histoneSL effects a markedly synergistic increase in protein expression in vivo.

11. Antibody Expression and Characterization

Cell Lines

RNA-based expression of humanised antibodies is done in either CHO-K1 or BHK-21 (Syrian hamster kidney, HER2-negative) cells. The tumour cell line BT-474 strongly expresses HER2 and is used to record antibody levels by FACS analysis. All cell lines except CHO are maintained in RPMI medium supplemented with FCS and glutamine according to the supplier's information. CHO cells are grown in Ham's F12 supplemented with 10% FCS. All cell lines can be obtained from the German collection of cell cultures (DSMZ, Braunschweig, Germany).

Antibody Expression

Various amounts of mRNA (G/C enriched as defined by the FIGS. 24 and 25) encoding the humanised antibody Herceptin (Trastuzumab) is transfected into either CHO or BHK cells by electroporation (300 V, 450 μF for CHO and 300 V, 150 μF for BHK). After transfection, cells are seeded onto 24-well cell culture plates at a density of 200.000 to 400.000 cells per well. For collection of secreted protein, medium is replaced by 250 μl of fresh medium after cell attachment to the plastic surface. Secreted protein is collected for 24-96 hours and stored at 4° C. In addition, cells are harvested into 50 μl of phosphate buffered saline (1×PBS buffer) containing 0.5% BSA and are disrupted by three freeze-thaw cycles. Cell lysates are cleared by centrifugation and stored at −80° C.

Western Blot Analysis

In order to detect translation of transfected RNA, proteins from either cell culture supernatants or cell lysates are separated by a 12% SDS-PAGE and blotted onto a nitrocellulose membrane. The humanised antibody Herceptin (Roche) can be used as a control. After blotting is completed, membranes are consecutively incubated with a biotinylated goat anti-human IgG antibody (Dianova), streptavidin coupled to horseradish peroxidase (BD), and a chemiluminescent substrate (SuperSignal West Pico, Pierce). Staining is detected with a Fuji LAS-1000 chemiluminescence camera.

FACS Analysis

Functional antibody formation can be demonstrated by FACS staining of antigen-expressing target cells. In order to examine the production of functional antibodies, cell culture supernatants of RNA-transfected cells are collected after 48 to 96 hours. Approximately 200.000 target BT-474 cells expressing HER2 are incubated with either control antibodies (Herceptin, Roche) or cell culture supernatants. For detection of bound antibodies, cells are stained with biotinylated goat anti-human IgG (Dianova) and PE-labelled streptavidin (Invitrogen). Cells are analysed on a FACSCanto II (BD).

The invention claimed is:

1. A method of treatment, comprising administering to a subject having a cancer a therapeutically effective amount of a composition comprising mRNA encoding Ipilimumab antibody, wherein said cancer is melanoma, renal cell carcinoma, sarcoma, lung cancer, ovarian cancer, leukemia, lymphoma, brain and central nervous system tumors, testicular cancer, prostate cancer, pancreatic cancer, or breast cancer, and wherein the mRNA further comprises at least one histone stem-loop sequence.

2. The method of claim 1, wherein the mRNA further comprises a histone stem-loop portion of SEQ ID NO: 58.

3. The method of claim 1, wherein the G/C content of the polypeptide encoding sequence of the mRNA is increased compared with the G/C content of a polypeptide encoding sequence of a wild-type nucleic acid encoding the Ipilimumab antibody.

4. The method of claim 1, wherein the composition comprises a first mRNA that encodes the Ipilimumab antibody light chain and a second mRNA that encodes the Ipilimumab antibody heavy chain.

5. The method of claim 1, wherein the composition comprises a mRNA that encodes the Ipilimumab antibody light chain and the Ipilimumab antibody heavy chain, wherein the Ipilimumab antibody light chain and Ipilimumab antibody heavy chain coding sequences are linked by an internal ribosomal entry site (IRES).

6. The method of claim 1, wherein the mRNA comprises a 5' cap structure.

7. The method of claim 1, wherein the mRNA comprises a poly(A) sequence of about 25 to about 400 adenosine nucleotides.

8. The method of claim 1, wherein the mRNA comprises a poly(C) sequence of 10 to 200 cytosine nucleotides.

9. The method of claim 1, wherein the mRNA further comprises a stabilizing sequence from an alpha globin 3' UTR.

10. The method of claim 1, wherein the mRNA is modified by introduction of a non-native nucleotide compared with a native mRNA sequence or by covalent coupling of the mRNA with a further chemical moiety.

11. The method of claim 10, wherein the mRNA is coupled to a lipid.

12. The method of claim 10, wherein the mRNA comprises a chemical modification relative to a naturally occurring mRNA.

13. The method of claim 10, wherein the non-native nucleotide is selected from the group consisting of 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, and xanthosine-5'-triphosphate.

14. The method of claim 1, wherein the mRNA is complexed with a cationic or polycationic compound.

15. The method of claim 1, wherein the cancer is a sarcoma, melanoma, lung cancer, ovarian cancer, leukemia, lymphoma, brain and central nervous system tumors, testicular cancer, prostate cancer, pancreatic cancer, or breast cancer.

16. The method of claim 1, wherein the composition is administered by injection.

17. The method of claim 1, wherein the composition is administered by intralesional administration.

* * * * *

SEQUENCE LISTING

```
<160> NUMBER OF SEQ ID NOS: 60

<210> SEQ ID NO 1
<211> LENGTH: 16
<212> TYPE: RNA
<213> ORGANISM: artificial
<220> FEATURE:
<223> OTHER INFORMATION: histone stem-loop sequence according to formula
      (Ic): metazoan and protozoan histone stem-loop consensus sequence
      without stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof
```

<400> SEQUENCE: 1
ngnnnnnnun nnnncn                                                   16

<210> SEQ ID NO 2
<211> LENGTH: 26
<212> TYPE: RNA
<213> ORGANISM: artificial
<220> FEATURE:
<223> OTHER INFORMATION: histone stem-loop sequence according to formula
      (IIc): metazoan and protozoan histone stem-loop consensus sequence
      with stem bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 2
nnnnnngnnn nnnunnnnnc nnnnnn                                        26

<210> SEQ ID NO 3
<211> LENGTH: 16
<212> TYPE: RNA
<213> ORGANISM: artificial
<220> FEATURE:
<223> OTHER INFORMATION: histone stem-loop sequence according to formula
      (Id): without stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 3
ncnnnnnnun nnnngn                                                   16

<210> SEQ ID NO 4
<211> LENGTH: 26
<212> TYPE: RNA
<213> ORGANISM: artificial
<220> FEATURE:
<223> OTHER INFORMATION: histone stem-loop sequence according to formula
      (IId): with stem bordering elements

```
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 4
nnnnnncnnn nnnunnnnng nnnnnn                                            26

<210> SEQ ID NO 5
<211> LENGTH: 16
<212> TYPE: RNA
<213> ORGANISM: artificial
<220> FEATURE:
<223> OTHER INFORMATION: histone stem-loop sequence according to formula
      (Ie): protozoan histone stem-loop consensus sequence without stem
      bordering elements
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof

<400> SEQUENCE: 5
dgnnnnnnun nnnnch                                                       16

<210> SEQ ID NO 6
<211> LENGTH: 26
<212> TYPE: RNA
<213> ORGANISM: artificial
<220> FEATURE:
<223> OTHER INFORMATION: histone stem-loop sequence according to formula
      (IIe): protozoan histone stem-loop consensus sequence with stem
      bordering elements
<220> FEATURE:
<221> NAME/KEY: misc_feature
<222> LOCATION: (1)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (22)..(26)
<223> OTHER INFORMATION: n is selected from a nucleotide selected from
      A, U, T, G and C, or a nucleotide analogue thereof
```

<400> SEQUENCE: 6
nnnnndgnnn nnnunnnnnc hnnnnn                                              26

<210> SEQ ID NO 7
<211> LENGTH: 16
<212> TYPE: RNA
<213> ORGANISM: artificial
<220> FEATURE:
<223> OTHER INFORMATION: histone stem-loop sequence according to formula
      (If): metazoan histone stem-loop consensus sequence without stem
      bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(3)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (7)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(12)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (14)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 7
ngnbyynnun vndncn                                                         16

<210> SEQ ID NO 8
<211> LENGTH: 26
<212> TYPE: RNA
<213> ORGANISM: artificial
<220> FEATURE:
<223> OTHER INFORMATION: histone stem-loop sequence according to formula
      (IIf): metazoan histone stem-loop consensus sequence with stem
      bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(13)
<223> OTHER INFORMATION: n is selected from a nucleotide selected from
      A, U, T, G and C, or a nucleotide analogue thereof

```
<220> FEATURE:
<221> NAME/KEY: misc_feature
<222> LOCATION: (15)..(15)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (17)..(17)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (19)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 8
nnnnnngnby ynnunvndnc nnnnnn                                          26

<210> SEQ ID NO 9
<211> LENGTH: 16
<212> TYPE: RNA
<213> ORGANISM: artificial
<220> FEATURE:
<223> OTHER INFORMATION: histone stem-loop sequence according to formula
      (Ig): vertebrate histone stem-loop consensus sequence without stem
      bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 9
nghyyydnuh abrdcn                                                     16

<210> SEQ ID NO 10
<211> LENGTH: 26
<212> TYPE: RNA
<213> ORGANISM: artificial
<220> FEATURE:
<223> OTHER INFORMATION: histone stem-loop sequence according to formula
      (IIg): vertebrate histone stem-loop consensus sequence with stem
      bordering elements
<220> FEATURE:
<221> NAME/KEY: misc_feature
<222> LOCATION: (1)..(2)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (4)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (13)..(13)
<223> OTHER INFORMATION: n is selected from a nucleotide selected from
      A, U, T, G and C, or a nucleotide analogue thereof
```

```
<220> FEATURE:
<221> NAME/KEY: misc_feature
<222> LOCATION: (21)..(25)
<223> OTHER INFORMATION: n is selected from a nucleotide selected from
      A, U, T, G and C, or a nucleotide analogue thereof

<400> SEQUENCE: 10
nnhnnnghyy ydnuhabrdc nnnnnh                                              26

<210> SEQ ID NO 11
<211> LENGTH: 16
<212> TYPE: RNA
<213> ORGANISM: artificial
<220> FEATURE:
<223> OTHER INFORMATION: histone stem-loop sequence according to formula
      (Ih): humane histone stem-loop consensus sequence (Homo sapiens)
      without stem bordering elements

<400> SEQUENCE: 11
dghycudyuh asrrcc                                                          16

<210> SEQ ID NO 12
<211> LENGTH: 26
<212> TYPE: RNA
<213> ORGANISM: artificial
<220> FEATURE:
<223> OTHER INFORMATION: histone stem-loop sequence according to formula
      (IIh): human histone stem-loop consensus sequence (Homo sapiens)
      with stem
      bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 12
nhaahdghyc udyuhasrrc cvhbnh                                              26

<210> SEQ ID NO 13
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 13
vgyyyyhhth rvvrcb                                                          16

<210> SEQ ID NO 14
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 14
sgyyyttytm arrrcs                                                          16
```

```
<210> SEQ ID NO 15
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 15
sgyycttttm agrrcs                                                           16

<210> SEQ ID NO 16
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (7)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(14)
<223> OTHER INFORMATION: n is selected from a nucleotide selected from
      A, U, T, G and C, or a nucleotide analogue thereof

<400> SEQUENCE: 16
dgnnnbnnth vnnnch                                                           16

<210> SEQ ID NO 17
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (13)..(14)
<223> OTHER INFORMATION: n is selected from a nucleotide selected from
      A, U, T, G and C, or a nucleotide analogue thereof

<400> SEQUENCE: 17
rgnnnyhbth rdnncy                                                           16

<210> SEQ ID NO 18
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(3)
<223> OTHER INFORMATION: n is selected from a nucleotide selected from
      A, U, T, G and C, or a nucleotide analogue thereof
```

-continued

```
<220> FEATURE:
<221> NAME/KEY: misc_feature
<222> LOCATION: (14)..(14)
<223> OTHER INFORMATION: n is selected from a nucleotide selected from
      A, U, T, G and C, or a nucleotide analogue thereof

<400> SEQUENCE: 18
rgndbyhyth rdhncy                                                    16

<210> SEQ ID NO 19
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 19
vgyyytyhth rvrrcb                                                    16

<210> SEQ ID NO 20
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 20
sgyycttytm agrrcs                                                    16

<210> SEQ ID NO 21
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 21
sgyycttttm agrrcs                                                    16

<210> SEQ ID NO 22
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 22
ggyycttyth agrrcc                                                    16

<210> SEQ ID NO 23
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 23
ggcycttytm agrgcc                                                    16
```

-continued

```
<210> SEQ ID NO 24
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 24
ggctcttttm agrgcc                                                       16

<210> SEQ ID NO 25
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 25
dghyctdyth asrrcc                                                       16

<210> SEQ ID NO 26
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 26
ggcyctttth agrgcc                                                       16

<210> SEQ ID NO 27
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 27
ggcycttttm agrgcc                                                       16

<210> SEQ ID NO 28
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)
<220> FEATURE:
<221> NAME/KEY: misc_feature
<222> LOCATION: (25)..(26)
<223> OTHER INFORMATION: n is selected from a nucleotide selected from
      A, U, T, G and C, or a nucleotide analogue thereof

<400> SEQUENCE: 28
hhhhvvgyyy yhhthrvvrc bvhhnn                                            26

<210> SEQ ID NO 29
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)
```

```
<400> SEQUENCE: 29
mhmhmsgyyy ttytmarrrc smchhh                                              26

<210> SEQ ID NO 30
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)

<400> SEQUENCE: 30
mmmmmsgyyc ttttmagrrc sachmh                                              26

<210> SEQ ID NO 31
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (17)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (22)..(22)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (24)..(26)
<223> OTHER INFORMATION: n is selected from a nucleotide selected from
      A, U, T, G and C, or a nucleotide analogue thereof

<400> SEQUENCE: 31
nnnnndgnnn bnnthvnnnc hnhnnn                                              26

<210> SEQ ID NO 32
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(2)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (5)..(5)
<223> OTHER INFORMATION: n is selected from a nucleotide selected from
      A, U, T, G and C, or a nucleotide analogue thereof
```

-continued

```
<220> FEATURE:
<221> NAME/KEY: misc_feature
<222> LOCATION: (8)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (18)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(26)
<223> OTHER INFORMATION: n is selected from a nucleotide selected from
      A, U, T, G and C, or a nucleotide analogue thereof

<400> SEQUENCE: 32
nnhhnrgnnn yhbthrdnnc ydhhnn                                          26

<210> SEQ ID NO 33
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (19)..(19)
<223> OTHER INFORMATION: n is selected from a nucleotide selected from
      A, U, T, G and C, or a nucleotide analogue thereof

<400> SEQUENCE: 33
nhhhvrgndb yhythrdhnc yrhhhh                                          26

<210> SEQ ID NO 34
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)
<220> FEATURE:
<221> NAME/KEY: misc_feature
<222> LOCATION: (26)..(26)
<223> OTHER INFORMATION: n is selected from a nucleotide selected from
      A, U, T, G and C, or a nucleotide analogue thereof

<400> SEQUENCE: 34
hhmhmvgyyy tyhthrvrrc bvmhhn                                          26

<210> SEQ ID NO 35
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)

<400> SEQUENCE: 35
mmmmmsgyyc ttytmagrrc smchhh                                          26
```

```
<210> SEQ ID NO 36
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)

<400> SEQUENCE: 36
mmmmmsgyyc ttttmagrrc sachmh                                              26

<210> SEQ ID NO 37
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)
<220> FEATURE:
<221> NAME/KEY: misc_feature
<222> LOCATION: (24)..(25)
<223> OTHER INFORMATION: n is selected from a nucleotide selected from
      A, U, T, G and C, or a nucleotide analogue thereof

<400> SEQUENCE: 37
hhmamggyyc ttythagrrc cvhnnm                                              26

<210> SEQ ID NO 38
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)

<400> SEQUENCE: 38
hhaamggcyc ttytmagrgc cvchhm                                              26

<210> SEQ ID NO 39
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)

<400> SEQUENCE: 39
mmaamggctc ttttmagrgc cmcymm                                              26

<210> SEQ ID NO 40
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 40
nhaahdghyc tdythasrrc cvhbnh                                              26
```

```
<210> SEQ ID NO 41
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 41
hhaamggcyc tttthagrgc cvmynm                                          26

<210> SEQ ID NO 42
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)

<400> SEQUENCE: 42
hmaaaggcyc ttttmagrgc crmyhm                                          26

<210> SEQ ID NO 43
<211> LENGTH: 1747
<212> TYPE: RNA
<213> ORGANISM: artificial
<220> FEATURE:
<223> OTHER INFORMATION: mRNA sequence of ppLuc(GC)-ag

<400> SEQUENCE: 43
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc guggugugcu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu gguguucgug agcaagaagg ccugcagaa      420 gauccugaac gugcagaaga gcugcccau caccagaag aucaucauca uggacagcaa      480
gaccgacuac cagggcuucc agucgaugua cacguucgug accagccacc ucccgccggg     540
cuucaacgag uacgacuucg ucccggagag cuucgaccgg acaagacca ucgcccugau      600 caugaacagc agcggcagca ccggccugcc gaaggggug gcccugccgc accgaccgc       660 cugcgugcgc uucucgcacg cccgggaccc caucuucggc aaccagauca ucccggacac     720
cgccauccug agcguggugc cguuccacca cggcuucggc auguucacga cccugggcua     780
ccucaucugc ggcuuccggg ugguccugau guaccguuc gaggaggagc uguuccugcg      840
gagccugcag gacuacaaga uccagagcgc gcugcucgug ccgacccugu ucagcuucuu     900
cgccaagagc acccugaucg acaaguacga ccugucgaac cugcacgaga ucgccagcgg     960
gggcgccccg cugagcaagg agggggcga ggccguggcc aagcgguucc accucccggg    1020
cauccgccag ggcuacggcc ugaccgagac cacgagcgcg auccugauca ccccgaggg    1080 ggacgacaag ccgggcgccg ugggcaaggu gguccgguuc uucgaggcca aggugggga    1140 ccuggacacc ggcaagaccc ugggcgugaa ccagcggggc gagcugugcg ugcgggggcc    1200
```

| | |
|---|---:|
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggucuuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggccccuccu cccuccuugc accgagauua | 1740 |
| auagauc | 1747 |

<210> SEQ ID NO 44
<211> LENGTH: 1806
<212> TYPE: RNA
<213> ORGANISM: artificial
<220> FEATURE:
<223> OTHER INFORMATION: mRNA sequence of ppLuc(GC)-ag-A64

<400> SEQUENCE: 44

| | |
|---|---:|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc gugguggugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug ggaucagcc agccgaccgu ggucuucgug agcaagaagg ccugcagaa | 420 |
| gauccugaac gugcagaaga gcugcccau cauccgaag aucaucauca uggacagcaa | 480 |
| gaccgacuac cagggcuucc agucgaugua cacguucgug accagccacc uccgccggg | 540 |
| cuucaacgag uacgacuucg uccggagag cuucgaccgg acaagacca ucgcccugau | 600 |
| caugaacagc agcggcagca ccggccugcc gaagggggug gcccugccgc accggaccgc | 660 |
| cugcgugcgc uucucgcacg cccgggaccc caucuucgc aaccagauca ucccggacac | 720 |
| cgccauccug agcgugguc cguuccacca cggcuucggc auguucacga cccugggcua | 780 |
| ccucaucugc ggcuuccggg uggccugau guaccggguuc gaggaggagc uguuccugcg | 840 |
| gagccugcag gacuacaaga uccagagcgc gcugcucgug ccgacccugu cagcuucuu | 900 |
| cgccaagagc acccugaucg acaaguacga ccugucgaac cugcacgaga ucgccagcgg | 960 |
| gggcgccccg cugagcaagg agguggggcga ggccgguggcc aagcgguucc accucccggg | 1020 |
| cauccgccag ggcuacggcc ugaccgagac cacgagcgcg auccugauca cccccgaggg | 1080 |
| ggacgacaag ccgggcgccg ugggcaaggu gguccgguuc uucgaggcca gguggugga | 1140 |
| ccuggacacc ggcaagaccc ugggcgugaa ccagcggggc gagcugugcg ucgggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |

| | |
|---|---|
| gaaggagauc gucgacuacg uggccagcca ggugaccacc gccaagaagc ugcggggcgg | 1560 |
| cguggguguuc uggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccugc accgagauua | 1740 |
| auaaaaaaaa aaaaaaaaaa aaaaaaaaaa aaaaaaaaaa aaaaaaaaaa aaaaaaaaaa | 1800 |
| aaaaaa | 1806 |

<210> SEQ ID NO 45
<211> LENGTH: 1772
<212> TYPE: RNA
<213> ORGANISM: artificial
<220> FEATURE:
<223> OTHER INFORMATION: mRNA sequence of ppLuc(GC)-ag-histoneSL

<400> SEQUENCE: 45

| | |
|---|---|
| gggagaaagc uugaggaugg aggacgccaa gaacaucaag aagggcccgg cgcccuucua | 60 |
| cccgcuggag gacgggaccg ccggcagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc gugguugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggugcugug agcaagaagg ccugcagaa | 420 |
| gauccugaac gugcagaaga agcugcccau cauccagaag aucaucauca uggacagcaa | 480 |
| gaccgacuac caggggcuucc agucgaugua cacguucgug accagccacc ucccgccggg | 540 |
| cuucaacgag uacgacuucg ucccggagag cuucgaccgg gacaagacca ucgcccugau | 600 |
| caugaacagc agcggcagca ccggccugcc gaagggggug gcccgccgc accgaccgc | 660 |
| cugcgugcgc uucucgcacg cccgggaccc caucuucggc aaccagauca ucccggacac | 720 |
| cgccauccug agcguggugc cguuccacca cggcuucggc auguucacga cccugggcua | 780 |
| ccucaucugc ggcuuccggg ugguccugau guaccgguuc gaggaggagc uguuccugcg | 840 |
| gagcccugcag gacuacaaga uccagagcgc gcugcucgug ccgacccugu ucagcuucuu | 900 |
| cgccaagagc acccugaucg acaaguacga ccugucgaac cugcacgaga ucgccagcgg | 960 |
| gggcgccccg cugagcaagg ggugggcga ggccguggcc aagcgguucc accucccggg | 1020 |
| cauccgccag ggcuacgggcc ugaccgagac cacgagcgcg auccugauca cccccgaggg | 1080 |
| ggacgacaag ccgggcgccg ugggcaaggu ggucccguuc uucgaggcca aggugguugga | 1140 |
| ccuggacacc ggcaagaccc ugggcgugaa ccagcggggc gagcugugcg ugcggggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggguguuc uggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |

```
agacugacua gcccgauggg ccucccaacg ggcccuccuc cccuccuugc accgagauua    1740
auagaucuca aaggcucuuu ucagagccac ca                                 1772
```

<210> SEQ ID NO 46
<211> LENGTH: 1835
<212> TYPE: RNA
<213> ORGANISM: artificial
<220> FEATURE:
<223> OTHER INFORMATION: mRNA sequence of ppLuc(GC)-ag-A64-histoneSL

<400> SEQUENCE: 46

```
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu ggauuccgug agcaagaagg ccugcagaa    420 gauccugaac gugcagaaga gcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg acaagaccca ucgcccugau    600
caugaacagc agcggcagca ccggccugcc gaaggggggug gcccugccgc accggaccgc    660
cugcgugcgc uucucgcacg cccgggaccc caucuucggc aaccagauca uccccggacac    720 cgccauccug agcgugguc cguuccacca cggcuucggc auguucacga cccugggcua    780
ccucaucugc ggcuuccggg uggccugau guaccggugc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg agguggcga ggccguggcc aagcgguucc accuccccggg    1020 cauccgccag ggcuacggcc ugaccgagac cacgagcgcg auccugauca cccccgaggg    1080
ggacgacaag ccgggcgccg ugggccaaggu gguccccguuc uucgaggcca aggugguga    1140 ccuggacacc ggcaagaccc ugggcgugaa ccagcggggc gagcugugcg ugcgggggcc    1200
gaugaucaug agcggcuacg ugaacaaccc ggaggccacc aacgcccuca ucgacaagga    1260
cggcuggcug cacagcggcg acaucgccua cuggacgag gacgagcacu ucuucaucgu    1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcggugu ggugcuggag cacggcaaga ccaugacgga    1500
gaaggagauc gucgacuacg uggccagcca ggugaccacc gccaagaagc ugcggggcgg    1560
cguggugurc guggacgagg ucccgaaggg cccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccuugc accgagauua    1740
auaaaaaaaa aaaaaaaaaa aaaaaaaaa aaaaaaaaa aaaaaaaaaa aaaaaaaaaa    1800
aaaaaaugca ucaaaggcuc uuuucagagc cacca                              1835
```

```
<210> SEQ ID NO 47
<211> LENGTH: 1869
<212> TYPE: RNA
<213> ORGANISM: artificial
<220> FEATURE:
<223> OTHER INFORMATION: mRNA sequence of ppLuc(GC)-ag-A120

<400> SEQUENCE: 47
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc gugguguscu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu ggcguucgug agcaagaagg ccugcagaa      420
gauccugaac gugcagaaga gcugcccau cauccgaaag aucaucauca uggacagcaa     480
gaccgacuac cagggcuucc agucgaugua cacguucgug accagccacc ucccgccggg     540
cuucaacgag uacgacuucg ucccggagag cuucgaccgg acaagacca ucgcccugau     600
caugaacagc agcggcagca ccggccugcc gaaggggug gcccugccgc accggaccgc      660
cugcgugcgc uucucgcacg cccgggaccc caucuucggc aaccagauca ucccggacac     720
cgccauccug agcgguguc cguuccacca cggcuucggc auguucacga cccugggcua     780
ccucaucugc ggcuuccggg ugguccugau guaccgguuc gaggaggagc uguuccugcg     840
gagccugcag gacuacaaga uccagagcgc gcugcucgug ccgacccugu cagcuucuu     900
cgccaagagc acccugaucg acaaguacga ccugucgaac cugcacgaga ucgccagcgg     960
gggcgccccg cugagcaagg ggugggcga ggccguggcc aagcgguucc accuccgg     1020
cauccgccag ggcuacggcc ugaccgagac cacgagcgcg auccgauca cccccgaggg    1080
ggacgacaag ccggcgccg ugggcaaggu ggucccguuc uucgaggcca ggugguga      1140
ccuggacacc ggcaagaccc ugggcgugaa ccagcggggc gagcugugcg ugcggggcc     1200
gaugaucaug agcggcacug ugaacaaccc ggaggccacc aacgcccuca ucgacaagga     1260
cggcuggcug cacagcggcg acaucgccua cuggacgag gacgagcacu ucuucaucgu     1320
cgaccggcug aagucgcuga ucaaguacaa gggcuaccag guggcgccgg ccgagcugga     1380
gagcauccug cuccagcacc ccaacaucu cgacgccggg guggccgggc ugccggacga     1440
cgacgccggc gagcugccgg ccgcgguggu ggugcuggag cacggcaaga ccaugacgga     1500
gaaggagauc gucgacuacg uggccagcca ggugaccacc gccaagaagc ugcggggcgg     1560
cguggguuc guggacgagg ucccgaaggg ccugaccggg aagcucgacg cccggaagau     1620
ccgcgagauc cugaucaagg ccaagaaggg cggcaagauc gccguguaag acuaguuaua     1680
agacugacua gcccgauggg ccucccaacg ggccccuccu cccuccuugc accgagauua     1740
auagaucuaa aaaaaaaaaa aaaaaaaaaa aaaaaaaaaa aaaaaaaaaa aaaaaaaaa      1800
aaaaaaaaaa aaaaaaaaaa aaaaaaaaaa aaaaaaaaaa aaaaaaaaaa aaaaaaaaa      1860
aaaaaaaaa                                                            1869

<210> SEQ ID NO 48
<211> LENGTH: 1858
<212> TYPE: RNA
<213> ORGANISM: artificial
```

```
<220> FEATURE:
<223> OTHER INFORMATION: mRNA sequence of ppLuc(GC)-ag-A64-ag

<400> SEQUENCE: 48
gggagaaagc uugaggaugg aggacgccaa gaacaucaag aagggcccgg cgcccuucua       60
cccgcuggag acgggaccg ccggcgagca gcuccacaag gccaugaagc gguacgcccu      120
ggugccgggc acgaucgccu ucaccgacgc ccacaucgag gucgacauca ccuacgcgga      180
guacuucgag augagcgugc gccuggccga ggccaugaag cgguacggcc ugaacaccaa      240
ccaccggauc guggugugcu cggagaacag ccugcaguuc uucaugccgg ugcugggcgc      300
ccucuucauc ggcguggccg ucgccccggc gaacgacauc uacaacgagc gggagcugcu      360
gaacagcaug gggaucagcc agccgaccgu ggguucgug agcaagaagg ccugcagaa       420 gauccugaac gugcagaaga gcugcccau cauccgaaag aucaucauca uggacagcaa      480
gaccgacuac cagggcuucc agucgaugua cacguucgug accagccacc ucccgccggg      540
cuucaacgag uacgacuucg ucccggagag cuucgaccgg acaagacca ucgcccugau      600 caugaacagc agcggcagca ccggccugcc gaaggggug gccugccgc accggaccgc       660 cugcgugcgc uucucgcacg cccgggaccc caucuucggc aaccagauca ucccggacac      720
cgccauccug agcguggugc cguuccacca cggcuucggc auguuacga cccugggcua       780 ccucaucugc ggcuuccggg uggccugau guaccgguuc gaggaggagc uguuccugcg      840
gagccugcag gacuacaaga uccagagcgc gcugcucgug ccgacccugu ucagcuucuu      900
cgccaagagc acccugaucg acaaguacga ccugucgaac cugcacgaga ucgccagcgg      960
gggcgccccg cugagcaagg agguggggcga ggccguggcc aagcgguucc accucccggg     1020
cauccgccag ggcuacggcc ugaccgagac cacgagcgcg auccugauca ccccgagg        1080 ggacgacaag ccgggcgccg ugggcaaggu ggucccguuc uucgaggcca aggugguga      1140 ccuggacacc ggcaagaccc ugggcgugaa ccagcggggc gagcugugcg ugcggggcc      1200 gauaaucaug agcggcuacg ugaacaaccc ggaggccacc aacgcccuca ucgacaagga     1260
cggcuggcug cacagcggcg acaucgccua cugggacgag gacgagcacu ucuucaucgu     1320
cgaccggcug aagucgcuga ucaaguacaa gggcuaccag guggcgccgg ccgagcugga     1380
gagcauccug cuccagcacc ccaacaucuu cgacgccggc guggccgggc ugccggacga     1440
cgacgccggc gagcugccgg ccgcgguggu ggugcuggag cacggcaaga ccaugacgga     1500
gaaggagauc gucgacuacg uggccagcca ggugaccacc gccaagaagc ugcggggcgg     1560
cguggugguu guggacgagg ucccgaaggg ccugaccggg aagcucgacg cccggaagau     1620
ccgcgagauc cugaucaagg ccaagaaggg cggcaagauc gccguguaag acuaguuaua     1680
agacugacua gcccgauggg ccucccaacg ggcccuccuc cccuccuugc accgagauua     1740
auaaaaaaaa aaaaaaaaaa aaaaaaaaaa aaaaaaaaaa aaaaaaaaaa aaaaaaaaaa     1800
aaaaaaugca uccugcccga ugggccuccc aacgggcccu ccuccccucc uugcaccg       1858

<210> SEQ ID NO 49
<211> LENGTH: 1894
<212> TYPE: RNA
<213> ORGANISM: artificial
<220> FEATURE:
<223> OTHER INFORMATION: mRNA sequence of ppLuc(GC)-ag-A64-aCPSL
```

<400> SEQUENCE: 49

```
gggagaaagc uugaggaugg aggacgccaa gaacaucaag aagggcccgg cgcccuucua        60
cccgcuggag gacgggaccg ccggcgagca gcuccacaag gccaugaagc gguacgcccu       120
ggugccgggc acgaucgccu ucaccgacgc ccacaucgag gucgacauca ccuacgcgga       180
guacuucgag augagcgugc gccuggccga ggccaugaag cgguacggcc ugaacaccaa       240
ccaccggauc gugugugcu cggagaacag ccugcaguuc uucaugccgg ugcugggcgc       300
ccucuucauc ggcgugcc cgccccggc gaacgacauc uacaacgagc gggagcugcu       360
gaacagcaug gggaucagcc agccgaccgu ggug uucgug agcaagaagg gccugcagaa    420
gauccugaac gugcagaaga gcugcccau cauccagaag aucaucauca uggacagcaa       480
gaccgacuac cagggcuucc agucgaugua cacguucgug accagccacc ucccgccggg       540
cuucaacgag uacgacuucg ucccggagag cuucgaccgg gacaagacca ucgcccugau       600
caugaacagc agcggcagca ccggccugcc gaagggggug gcccugcgc accggaccgc       660
cugcgugcgc uucucgcacg cccgggaccc caucuucggc aaccagauca ucccggacac       720
cgccauccug agcgugguc cguuccacca cggcuucggc auguucacga cccugggcua       780
ccucaucugc ggcuuccggg uggccugau guaccgguuc gaggaggagc uguuccugcg       840
gagccugcag gacuacaaga uccagagcgc gcugcucgug ccgacccugu cagcuucuu       900
cgccaagagc acccugaucg acaaguacga ccugucgaac cugcacgaga ucgccagcgg       960
gggcgccccg cugagcaagg aggugggcga ggccgggcc aagcgguucc accucccggg      1020
cauccgccag ggcuacggcc ugaccgagac cacgagcgcg auccugauca cccccgaggg      1080
ggacgacaag ccgggcgccg ugggcaaggu ggucccguuc uucgaggcca aggugg ugga      1140
ccuggacacc ggcaagaccc ugggcgugaa ccagcgggcc gagcugugcg ugcggggccc      1200
gaugaucaug agcggcuacg ugaacaaccc ggaggccacc aacgcccuca ucgacaagga      1260
cggcuggcuu cacagcggcg acaucgccua cuggacgag gacgagcacu ucuucaucgu      1320
cgaccggcug aagucgcuga ucaaguacaa gggcuaccag guggcgccgg ccgagcugga      1380
gagcauccug cuccagcacc ccaacaucuu cgacgccggc guggccgggc ugccggacga      1440
cgacgccggc gagcugccgg ccgcgguggu ggugcuggag cacggcaaga ccaugacgga      1500
gaaggagauc gucgacacg uggccagcca ggugaccacc gccaagaagc ugcggggcgg      1560
cguggugu uc guggacgagg ucccgaaggg cc ugaccggg aagcucgacg cccggaagau      1620
ccgcgagauc cugaucaagg ccaagaaggg cggcaagauc gccguguaag acuaguuaua      1680
agacugacua gcccgauggg ccucccaacg ggccccuccu cccuccuugc accgagauua      1740
auaaaaaaaa aaaaaaaaaa aaaaaaaaaa aaaaaaaaaa aaaaaaaaaa aaaaaaaaaa      1800
aaaaaaugca ucaauuccua cacgugaggc gcugugauuc ccuaucccc uucauucccu       1860
auacauuagc acagcgccau ugcauguagg aauu                                   1894
```

<210> SEQ ID NO 50
<211> LENGTH: 1909
<212> TYPE: RNA
<213> ORGANISM: artificial
<220> FEATURE:
<223> OTHER INFORMATION: mRNA sequence of ppLuc(GC)-ag-A64-PolioCL

<400> SEQUENCE: 50

```
gggagaaagc uugaggaugg aggacgccaa gaacaucaag aagggcccgg cgcccuucua        60
cccgcuggag gacgggaccg ccggcgagca gcuccacaag gccaugaagc gguacgcccu       120
```

```
ggugccgggc acgaucgccu ucaccgacgc ccacaucgag gucgacauca ccuacgcgga    180
guacuucgag augagcgugc gccuggccga ggccaugaag cgguacgccc ugaacaccaa    240
ccaccggauc gugugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu ggguucgug agcaagaagg ccugcagaa    420 gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg acaagacca ucgcccugau    600 caugaacagc agcggcagca ccggccugcc gaagggggug gcccugccgc accggaccgc    660
cugcgugcgc uucucgcacg cccgggaccc caucuucggc aaccagauca ucccggacac    720
cgccauccug agcguggugc cguuccacca cggcuucggc auguucacga cccugggcua    780
ccucaucugc ggcuuccggg uggucccgau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg agguggggcga ggccguggcc aagcgguucc accucccggg    1020
cauccgccag ggcuacggcc ugaccgagac cacgagcgcg auccugauca ccccgagggg    1080
ggacgacaag ccgggcgccg ugggcaaggu ggucccguuc uucgaggcca agguggugga    1140
ccuggacacc ggcaagaccc uggggcgugaa ccagcggggc gagcugugcg ugcggggggcc    1200 gaugaucaug agcggcuacg ugaacaaccc ggaggccacc aacgcccuca ucgacaagga    1260
cggcuggcug cacagcggcg acaucgccua cugggacgag gacgagcacu ucuucaucgu    1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcggugg ggugcuggag cacggcaaga ccaugacgga    1500
gaaggagauc gucgacuacg uggccagcca ggugaccacc gccaagaagc ugcggggcgg    1560 cguggguuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgaugg ccucccaacg ggcccuccuc cccuccuugc accgagauua    1740
auaaaaaaaa aaaaaaaaa aaaaaaaaaa aaaaaaaaaa aaaaaaaaaa aaaaaaaaaa    1800
aaaaaaugca ucaauucuaa aacagcucug ggguuguacc cacccagag gcccacgugg    1860 cggcuaguac uccgguauug cgguacccuu guacgccugu uuuagaauu              1909
```

```
<210> SEQ ID NO 51
<211> LENGTH: 1841
<212> TYPE: RNA
<213> ORGANISM: artificial
<220> FEATURE:
<223> OTHER INFORMATION: mRNA sequence of ppLuc(GC)-ag-A64-G30

<400> SEQUENCE: 51
```

```
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacgccc ugaacaccaa    240
ccaccggauc gugugugcu cggagaacag ccugcaguuc uucaugccgg ugcugggcgc    300
```

| | |
|---|---|
| ccucuucauc ggcguggccg ucgccccggc gaacgacauc uacaacgagc gggagcugcu | 360 |
| gaacagcaug gggaucagcc agccgaccgu gguguucgug agcaagaagg gccugcagaa | 420 |
| gauccugaac gugcagaaga agcugcccau cauccagaag aucaucauca uggacagcaa | 480 |
| gaccgacuac cagggcuucc agucgaugua cacguucgug accagccacc ucccgccggg | 540 |
| cuucaacgag uacgacuucg ucccggagag cuucgaccgg acaagacca ucgcccugau | 600 |
| caugaacagc agcggcagca ccggccugcc gaagggggug gcccugccgc accgaccgc | 660 |
| cugcgugcgc uucucgcacg cccgggaccc caucuucggc aaccagauca ucccggacac | 720 |
| cgccauccug agcguggugc cguuccacca cggcuucggc auguucacga cccugggcua | 780 |
| ccucaucugc ggcuuccggg ugguccugau guaccgguuc gaggaggagc uguuccugcg | 840 |
| gagccugcag gacuacaaga uccagagcgc gcucucgug ccgacccugu ucagcuucuu | 900 |
| cgccaagagc acccugaucg acaaguacga ccugucgaac cugcacgaga ucgccagcgg | 960 |
| gggcgccccg cugagcaagg aggugggcga ggccgguggcc aagcgguucc accucccggg | 1020 |
| caucgccag ggcuacggcc ugaccgagac cacgagcgcg auccgauca cccccgaggg | 1080 |
| ggacgacaag ccgggcgccg ugggcaaggu gguccccguuc uucgaggcca agguggugga | 1140 |
| ccuggacacc ggcaagaccc uggcugaa ccagcgggc gagcugugcg ugcgggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggguuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uggggggggg gggggggggg gggggggggg g | 1841 |

<210> SEQ ID NO 52
<211> LENGTH: 1841
<212> TYPE: RNA
<213> ORGANISM: artificial
<220> FEATURE:
<223> OTHER INFORMATION: mRNA sequence of ppLuc(GC)-ag-A64-U30

<400> SEQUENCE: 52

| | |
|---|---|
| gggagaaagc uugaggaugg aggacgccaa gaacaucaag aagggccgg cgccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu gguguucgug agcaagaagg gccugcagaa | 420 |
| gauccugaac gugcagaaga agcugcccau cauccagaag aucaucauca uggacagcaa | 480 |
| gaccgacuac cagggcuucc agucgaugua cacguucgug accagccacc ucccgccggg | 540 |

| | |
|---|---:|
| cuucaacgag uacgacuucg ucccggagag cuucgaccgg acaagacca ucgcccugau | 600 |
| caugaacagc agcggcagca ccggccugcc aagggggug gcccugccgc accggaccgc | 660 |
| cugcgugcgc uucucgcacg cccgggaccc caucuucggc aaccagauca ucccggacac | 720 |
| cgccauccug agcguggugc cguuccacca cggcuucggc auguucacga cccugggcua | 780 |
| ccucaucugc ggcuuccggg ugguccugau guaccgguuc gaggaggagc uguuccugcg | 840 |
| gagccugcag gacuacaaga uccagagcgc gcugcucgug ccgacccugu ucagcuucuu | 900 |
| cgccaagagc acccugaucg acaaguacga ccugucgaac cugcacgaga ucgccagcgg | 960 |
| gggcgccccg cugagcaagg agugggcga ggccgguggcc aagcgguucc accucccggg | 1020 |
| cauccgccag ggcuacggcc ugaccgagac cacgagcgcg auccugauca cccccgaggg | 1080 |
| ggacgacaag ccgggcgccg ugggcaaggu gguccccguuc uucgaggcca aggugguga | 1140 |
| ccuggacacc ggcaagaccc ugggcgugaa ccagcggggc gagcugugcg ugcgggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag acggcaagaa ccaugacgga | 1500 |
| gaaggagauc gucgacuacg uggccagcca ggugaccacc gccaagaagc ugcggggcgg | 1560 |
| cguggucuuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccuugc accgagauua | 1740 |
| auaaaaaaaa aaaaaaaaa aaaaaaaaa aaaaaaaaa aaaaaaaaa aaaaaaaaa | 1800 |
| aaaaaaugca uuuuuuuuu uuuuuuuuu uuuuuuuuu u | 1841 |

<210> SEQ ID NO 53
<211> LENGTH: 1857
<212> TYPE: RNA
<213> ORGANISM: artificial
<220> FEATURE:
<223> OTHER INFORMATION: mRNA sequence of ppLuc(GC)-ag-A64-SL

<400> SEQUENCE: 53

| | |
|---|---:|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacgccc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggguguucgug agcaagaagg gccugcagaa | 420 |
| gauccugaac gugcagaaga agcugcccau cauccagaag aucaucauca uggacagcaa | 480 |
| gaccgacuac cagggcuucc agucgaugua cacguucgug accagccacc uccgcccggg | 540 |
| cuucaacgag uacgacuucg ucccggagag cuucgaccgg acaagacca ucgcccugau | 600 |
| caugaacagc agcggcagca ccggccugcc aagggggug gcccugccgc accggaccgc | 660 |
| cugcgugcgc uucucgcacg cccgggaccc caucuucggc aaccagauca ucccggacac | 720 |
| cgccauccug agcguggugc cguuccacca cggcuucggc auguucacga cccugggcua | 780 |

| | |
|---|---:|
| ccucaucugc ggcuuccggg ugguccugau guaccgguuc gaggaggagc uguuccugcg | 840 |
| gagccugcag gacuacaaga uccagagcgc gcugcucgug ccgacccugu cagcuucuu | 900 |
| cgccaagagc acccugaucg acaaguacga ccugucgaac cugcacgaga ucgccagcgg | 960 |
| gggcgccccg cugagcaagg aggugggcga ggccguggcc aagcgguucc accucccggg | 1020 |
| cauccgccag ggcuacggcc ugaccgagac cacgagcgcg auccugauca cccccgaggg | 1080 |
| ggacgacaag ccgggcgccg ugggcaaggu ggucccguuc uucgaggcca agguggugga | 1140 |
| ccuggacacc ggcaagaccc ugggcgugaa ccagcggggc gagcugugcg ugcgggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cgugguguuc guggacgagg ucccgaaggg ccugaccggg aagcucgacg cccggaagau | 1620 |
| ccgcgagauc cugaucaagg ccaagaaggg cggcaagauc ccguguaag acuaguuaua | 1680 |
| agacugacua gcccgauggg ccucccaacg ggcccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uuauggcggc cguguccacc acggauauca ccguggugga cgcggcc | 1857 |

<210> SEQ ID NO 54
<211> LENGTH: 1838
<212> TYPE: RNA
<213> ORGANISM: artificial
<220> FEATURE:
<223> OTHER INFORMATION: ppLuc(GC)-ag-A64-N32

<400> SEQUENCE: 54

| | |
|---|---:|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacgcc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggguucgug agcaagaagg ccugcagaa | 420 |
| gauccugaac gugcagaaga agcugcccau cauccgaaag aucaucauca uggacagcaa | 480 |
| gaccgacuac cagggcuucc agucgaugua cacguucgug accagccacc uccgccgggg | 540 |
| cuucaacgag uacgacuucg ucccggagag cuucgaccgg acaagacca ucgcccugau | 600 |
| caugaacagc agcggcagca ccggccugcc gaaggggug gcccugccgc accgaccgc | 660 |
| cugcgugcgc uucucgcacg cccgggaccc caucuucggc aaccagauca ucccggacac | 720 |
| cgccauccug agcgugggc cguuccacca cggcuucggc auguucacga cccugggcua | 780 |
| ccucaucugc ggcuuccggg ugguccugau guaccgguuc gaggaggagc uguuccugcg | 840 |
| gagccugcag gacuacaaga uccagagcgc gcugcucgug ccgacccugu cagcuucuu | 900 |
| cgccaagagc acccugaucg acaaguacga ccugucgaac cugcacgaga ucgccagcgg | 960 |
| gggcgccccg cugagcaagg aggugggcga ggccguggcc aagcgguucc accucccggg | 1020 |

| | |
|---|---|
| cauccgccag ggcuacggcc ugaccgagac cacgagcgcg auccugauca cccccgaggg | 1080 |
| ggacgacaag ccgggcgccg ugggcaaggu ggucccguuc uucgaggcca aggugguga | 1140 |
| ccuggacacc ggcaagaccc ugggcgugaa ccagcggggc gagcugugcg ugcgggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugcggga | 1500 |
| gaaggagauc gucgacuacg uggccagcca ggugaccacc gccaagaagc ugcggggcgg | 1560 |
| cguggugunc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccuugc accgagauua | 1740 |
| auaaaaaaaa aaaaaaaaa aaaaaaaaa aaaaaaaaa aaaaaaaaa aaaaaaaaa | 1800 |
| aaaaaaugca uccccucua gacaauugga auuccaua | 1838 |

<210> SEQ ID NO 55
<211> LENGTH: 771
<212> TYPE: RNA
<213> ORGANISM: artificial
<220> FEATURE:
<223> OTHER INFORMATION: mRNA sequence of MmEPO (GC) -ag-A64-C30

<400> SEQUENCE: 55

| | |
|---|---|
| gggagaaagc uuaccauggg cgugcccgag cggccgaccc ugcuccugcu gcucagccug | 60 |
| cugcucaucc cccuggggcu gcccguccuc ugcgcccccc cgcgccugau cugcgacucc | 120 |
| cgggugcugg agcgcuacau ccucgaggcc aaggaggcgg agaacgugac caugggcugc | 180 |
| gccgaggggc cccggcugag cgagaacauc acgucccccg acaccaaggu gaacuucuac | 240 |
| gccuggaagc gcauggaggu ggaggagcag gccaucgagg ucuggcaggg ccuguccuc | 300 |
| cugagcgagg ccauccugca ggcgcaggcc uccuggccca cuccagcca gccccggag | 360 |
| acacugcagc uccacaucga caaggccauc uccgggcugc ggagccugac cuccuccug | 420 |
| cgcgugcugg gcgcgcagaa ggagcucaug agcccgcccg acacgacccc cccggccccg | 480 |
| cugcggaccc ugaccgugga cacguucugc aagcucuucc gcgucuacgc caacuuccug | 540 |
| cggggcaagc ugaagcucua caccggggag gugugccgcc ggggcgaccg cugaccacua | 600 |
| guuauaagac ugacuagccc gaugggccuc ccaacgggcc cuccccccu ccuugcaccg | 660 |
| agauuaauaa aaaaaaaaa aaaaaaaaa aaaaaaaaa aaaaaaaaa aaaaaaaaa | 720 |
| aaaaaaaaaa aauauuccccc cccccccc ccccccccc cccccucua g | 771 |

<210> SEQ ID NO 56
<211> LENGTH: 796
<212> TYPE: RNA
<213> ORGANISM: artificial
<220> FEATURE:
<223> OTHER INFORMATION: mRNA sequence of MmEPO (GC) - ag - A64 -C30 -
      histoneSL

<400> SEQUENCE: 56

| | |
|---|---|
| gggagaaagc uuaccauggg cgugcccgag cggccgaccc ugcuccugcu gcucagccug | 60 |
| cugcucaucc cccuggggcu gcccguccuc ugcgcccccc cgcgccugau cugcgacucc | 120 |

| | |
|---|---:|
| cgggugcugg agcgcuacau ccucgaggcc aaggaggcgg agaacgugac caugggcugc | 180 |
| gccgaggggc cccggcugag cgagaacauc acgguccccg acaccaaggu gaacuucuac | 240 |
| gccuggaagc gcauggaggu ggaggagcag gccaucgagg ucuggcaggg ccugucccuc | 300 |
| cugagcgagg ccauccugca ggcgcaggcc uccuggcca acuccagcca gcccccggag | 360 |
| acacugcagc uccacaucga caaggccauc uccgggcugc ggagccugac ucccuccug | 420 |
| cgcgugcugg gcgcgcagaa ggagcucaug agcccgcccg acacgacccc ccggccccg | 480 |
| cugcggaccc ugaccgugga cacguucugc aagcucuucc gcgucuacgc caacuuccug | 540 |
| cggggcaagc ugaagcucua caccggggag gugugccgcc ggggcgaccg cugaccacua | 600 |
| guuauaagac ugacuagccc gaugggccuc ccaacgggcc uccuccccu ccuugcaccg | 660 |
| agauuaauaa aaaaaaaaaa aaaaaaaaaa aaaaaaaaaa aaaaaaaaaa aaaaaaaaaa | 720 |
| aaaaaaaaaa aaugcauccc cccccccccc cccccccccc ccccccccaa aggcucuuuu | 780 |
| cagagccacc agaauu | 796 |

<210> SEQ ID NO 57
<211> LENGTH: 3040
<212> TYPE: RNA
<213> ORGANISM: Artificial Sequence
<220> FEATURE:
<223> OTHER INFORMATION: Trastuzumab(GC) ag A64 C30

<400> SEQUENCE: 57

| | |
|---|---:|
| gggagaaagc uuaccauggc cgugaugcg ccgcggaccc uguccuccu gcugagcggc | 60 |
| gcccucgccc ugacgcagac cugggccggg gaggugcagc uggucgagag cggcgggggc | 120 |
| cucgugcagc cgggcggguc gcugcggcug agcugcgccg cgagcggguu caacaucaag | 180 |
| gacaccuaca uccacugggu gcgccaggcc cccggcaagg gccucgagug ggucgcccgg | 240 |
| aucuaccccca cgaacgggua caccgcuac gccgacagcg ugaagggccg guucaccauc | 300 |
| agcgcggaca ccucgaagaa cacggccuac cugcagauga acagccugcg cgccgaggac | 360 |
| accgccgugu acuacugcag ccgguggggc ggcgacgggu ucuacgccau ggacuacugg | 420 |
| gggcagggca cccucgucac cgugagcagc gcgucgacga aggggcccag cguguucccg | 480 |
| cuggccccca gcagcaagag caccagcggc gggaccgccg cccugggcug ccucgucaag | 540 |
| gacuacuucc ccgagcccgu gaccgugucg uggaacagcg gcgcgcugac gagcggguc | 600 |
| cacaccuucc cggccgugcu gcagagcagc ggccucuacu cgcugagcag cguggucacc | 660 |
| gugcccagca gcagccuggg gacccagacg uacaucugca acgugaacca caagcccucg | 720 |
| aacaccaagg ucgacaagaa ggugagcccc cgaagagcu gcgacaagac ccacaccugc | 780 |
| ccgcccugcc ccgcccccga gcuccuggc gggcccagcg uguucuguu cccgcccaag | 840 |
| cccaaggaca cgcucaugau cagccgcacc cccgaggca ccugcguggu ggucgacgug | 900 |
| agccacgagg accccgaggu gaaguucaac ugguacgucg acggcgugga ggugcacaac | 960 |
| gccaagacca gccgcggga ggagcaguac aacucgacgu accgcgucgu gagcgugcug | 1020 |
| accguccugc accaggacug gcucaacggc aaggaguaca gugcaaggu gagcaacaag | 1080 |
| gcccugcccg cgcccaucga aagaccauc agcaaggcca aggggcagcc ccgggagccg | 1140 |
| cagguguaca cccugccccc cagccgcgac gagcucacga agaaccaggu cagccugacc | 1200 |
| ugccuggug agggcuucua ccccucggac aucgccgugg aguggagag caacgggcag | 1260 |
| ccggagaaca acuacaagac cacccgcccc guccucgaca gcgacggcag cuucuuccug | 1320 |
| uacagcaagc ugacggugga caagucgcgg uggcagcagg gcaacguguu cagcugcagc | 1380 |

| | |
|---|---|
| gucaugcacg aggcccucca caaccacuac acccagaaga gccugagccu gagccccggg | 1440 |
| aagcaucauc aucaucauca uugaccaugc auuugaaagc cggggguggg agauccggau | 1500 |
| ugccagucug cucgauaucg caggcugggu ccgugacuac ccacucccccc uuuaauuccg | 1560 |
| ccccucuccc ucccccccccc cuaacguuac uggccgaagc cgcuuggaau aaggccggug | 1620 |
| ugcguuuguc uauauguuau uuccaccau auugccgucu uuuggcaaug ugagggcccg | 1680 |
| gaaaccuggc ccugucuucu ugacgagcau uccuaggggu cuucccccuc ucgccaaagg | 1740 |
| aaugcaaggu cuguugaaug ucgugaagga agcaguuccu cuggaagcuu cuugaagaca | 1800 |
| aacaacgucu guagcgaccc uuugcaggca gcggaacccc ccaccuggcg acaggugccu | 1860 |
| cugcggccaa aagccacgug uauaagauac accugcaaag gcggcacaac cccagugcca | 1920 |
| cguugugagu uggauaguug uggaaagagu caaauggcuc uccucaagcg auucaacaa | 1980 |
| ggggcugaag gaugcccaga agguaccccca uuguauggga ucgaucugg ggccucggug | 2040 |
| cacaugcuuu acgugugu uu agucgagguu aaaaaacguc uaggcccccc gaaccacggg | 2100 |
| gacgugguu uccuuugaaa aacacgauga uaauagaucu accauggccg ugauggcgcc | 2160 |
| gcggacccug guccuccugc ugagcggcgc ccucgcccug acgcagaccu gggccgggga | 2220 |
| cauccagaug acccagagcc cgucgagccu gagcgccagc gugggcgacc gggucacgau | 2280 |
| caccugccgc gcgagccagg acgugaacac cgccguggcc ugguaccagc agaagcccgg | 2340 |
| gaaggccccc aagcuccuga ucuacucggc gagcuuccua cagcggcg uccccagccg | 2400 |
| guucagcggg ucgcgcagcg gcaccgacuu cacgcucacc aucagcagcc ugcagccgga | 2460 |
| ggacuucgcc accacuacu gccagcagca cuacaccacg ccccccaccu ucgggcaggg | 2520 |
| caccaaggug gagaucaagc ggaccgugcc cgccccccagc gucuucaucu ucccgcccag | 2580 |
| cgacgagcag cugaagucgg gcacggccag cguggugugc cuccugaaca acuucuaccc | 2640 |
| ccgcgaggcg aagguccagu ggaaggugga caacgcccug cagagcggga acagccagga | 2700 |
| gagcgugacc gagcaggacu cgaaggacag caccuacagc cucagcagca cccugacgcu | 2760 |
| gagcaaggcc gacuacgaga agcacaaggu cuacgccugc gaggugaccc accagggggcu | 2820 |
| cucgagcccc gugaccaaga gcuucaaccg gggcgagugc ugaccacuag uuauaagacu | 2880 |
| gacuagcccg auggggccucc aacgggccc uccucccccuc cuugcaccga gauuaauaaa | 2940 |
| aaaaaaaaaa aaaaaaaaaa aaaaaaaaaa aaaaaaaaaa aaaaaaaaaa aaaaaaaaaa | 3000 |
| auauucccccc cccccccccc cccccccccc ccccucuag | 3040 |

<210> SEQ ID NO 58
<211> LENGTH: 3065
<212> TYPE: RNA
<213> ORGANISM: Artificial Sequence
<220> FEATURE:
<223> OTHER INFORMATION: Trastuzumab(GC) ag A64 C30 histoneSL

<400> SEQUENCE: 58

| | |
|---|---|
| gggagaaagc uuaccauggc cgugauggcg ccgcggaccc ugguccuccu gcugagcggc | 60 |
| gcccucgccc ugacgcagac cugggccggg gaggugcagc uggucgagag cggcggggggc | 120 |
| cucgugcagc cgggcgggguc gcucgggcug agcugcgccg cgagcgggguu caacaucaag | 180 |
| gacaccuaca uccacugggu gcgccaggcc cccggcaagg gccucgagug ggucgcccgg | 240 |
| aucuaccccca cgaacgggua caccccgcuac gccgacagcg ugaagggccg guucaccauc | 300 |
| agcgcggaca ccucgaagaa cacggccuac cugcagauga caagccugcg cgccgaggac | 360 |
| accgccgugu acuacugcag ccggugggg ggcgacgggu ucuacgccau ggacuacugg | 420 |

| | |
|---|---|
| gggcagggca cccucgucac cgugagcagc gcgucgacga agggggcccag cguguucccg | 480 |
| cuggccccca gcagcaagag caccagcggc gggaccgccg cccugggcug ccucgucaag | 540 |
| gacuacuucc ccgagcccgu gaccgugucg uggaacagcg gcgcgcugac gagcggggguc | 600 |
| cacaccuucc cggccgugcu gcagagcagc ggcucucuacu cgcugagcag cguggucacc | 660 |
| gugcccagca gcagccuggg gacccagacg uacaucugca acgugaacca caagcccucg | 720 |
| aacaccaagg ucgacaagaa gguggagccc cgaagagcu gcgacaagac ccacaccugc | 780 |
| ccgcccugcc ccgcccccga gcuccugggc gggcccagcg uguuccuguu cccgcccaag | 840 |
| cccaaggaca cgcucaugau cagccgcacc cccgagguca ccugcguggu ggucgacgug | 900 |
| agccacgagg accccgaggu gaaguucaac ugguacgucg acggcgugga ggugcacaac | 960 |
| gccaagacca gccgcgggga ggagcaguac aacucgacgu accgcgucgu gagcgugcug | 1020 |
| accguccugc accaggacug gcucaacggc aaggaguaca gugcaaggu gagcaacaag | 1080 |
| gcccugcccg cgcccaucga gaagaccauc agcaaggcca aggggcagcc ccgggagccg | 1140 |
| cagguguaca cccugccccc cagccgcgac gagcucacga agaaccaggu cagccugacc | 1200 |
| ugccugguga agggcuucua ccccucggac aucgccgugg agugggagag caacgggcag | 1260 |
| ccggagaaca acuacaagac caccccgccc guccucgaca cgacggcag cuucuuccug | 1320 |
| uacagcaagc ugacggugga caagucgcgg uggcagcagg gcaacguguu cagcugcagc | 1380 |
| gucaugcacg aggcccucca caaccacuac acccagaaga gccugagccu gagccccggg | 1440 |
| aagcaucauc aucaucauca uugaccaugc auuugaaagc cggggggugg agauccggau | 1500 |
| ugccagucug cucgauaucg caggcugggu ccgugacuac ccacuccccc uuuaauuccg | 1560 |
| ccccucuccc uccccccccc cuaacguuac uggccgaagc cgcuuggaau aaggccggug | 1620 |
| ugcguuugc uauauguuau uuccaccau auugccgucu uuuggcaaug ugagggcccg | 1680 |
| gaaaccuggc ccugucuucu ugacgagcau ccuaggggu cuuccccuc ucgccaaagg | 1740 |
| aaugcaaggu cuguugaaug ucgugaagga agcaguuccu cuggaagcuu cuugaagaca | 1800 |
| aacaacgucu guagcgaccc uuugcaggca gcggaacccc ccaccuggcg acaggugccu | 1860 |
| cugcggccaa aagccacgug uauaagauac accugcaaag gcggcacaac cccagugcca | 1920 |
| cguugugagu uggauaguug uggaaagagu caaauggcuc uccucaagcg uauucaacaa | 1980 |
| ggggcugaag gaugcccaga agguacccca uuguauggga ucugaucugg ggccucggug | 2040 |
| cacaugcuuu acgugugu uu agucgagguu aaaaaacguc uaggccccc gaaccacggg | 2100 |
| gacgugguuu uccuuugaaa aacacgauga uaauagaucu accauggccg ugauggcgcc | 2160 |
| gcggacccug guccuccugc ugagcggcgc ccucgcccug acgcagaccu gggccgggga | 2220 |
| cauccagaug acccagagcc cgucgagccu gagcgcagc gugggcgacc gggucacgau | 2280 |
| caccugccgc gcgagccagg acgugaacac cgccguggcc ugguaccagc agaagcccgg | 2340 |
| gaaggccccc aagcuccuga ucuacucggc gagcuuccug uacagcggcg ucccagccg | 2400 |
| guucagcggg ucgcgcagcg gcaccgacuu cacgcucacc aucagcagcc ugcagccgga | 2460 |
| ggacuucgcc accuacuacu gccagcagca cuacaccacg cccccaccu ucgggcaggg | 2520 |
| caccaaggug gagaucaagc ggaccguggc cgccccccagc gucuucaucu cccgcccag | 2580 |
| cgacgagcag cugaagucgg gcacggccag cguggugugc cuccugaaca acuucuaccc | 2640 |
| ccgcgagggcg aagguccagu ggaagguga caacgcccug cagagcggga acagccagga | 2700 |
| gagcgugacc gagcaggacu cgaaggacag caccuacagc cucagcagca cccugacgcu | 2760 |
| gagcaaggcc gacuacgaga agcacaaggu cuacgccugc gaggugaccc accaggggcu | 2820 |

```
cucgagcccc gugaccaaga gcuucaaccg gggcgagugc ugaccacuag uuauaagacu    2880
gacuagcccg augggccucc caacgggccc uccucccuc cuugcaccga gauuaauaaa     2940
aaaaaaaaaa aaaaaaaaaa aaaaaaaaaa aaaaaaaaaa aaaaaaaaaa aaaaaaaaaa    3000
augcaucccc cccccccccc cccccccccc ccccccaaa ggcucuuuuc agagccacca     3060
gaauu                                                                3065

<210> SEQ ID NO 59
<211> LENGTH: 11
<212> TYPE: RNA
<213> ORGANISM: Artificial Sequence
<220> FEATURE:
<223> OTHER INFORMATION: Synthetic oligonucleotide

<400> SEQUENCE: 59
accuuucucc a                                                         11

<210> SEQ ID NO 60
<211> LENGTH: 11
<212> TYPE: RNA
<213> ORGANISM: Artificial Sequence
<220> FEATURE:
<223> OTHER INFORMATION: Synthetic oligonucleotide

<400> SEQUENCE: 60
uggagaaagg u                                                         11
```